(12) United States Patent
Van Dijk et al.

(10) Patent No.: US 10,450,373 B2
(45) Date of Patent: *Oct. 22, 2019

(54) ANTI-PD-1 ANTIBODIES AND METHODS OF USE THEREOF

(71) Applicants: AGENUS INC., Lexington, MA (US); LUDWIG INSTITUTE FOR CANCER RESEARCH LTD, Zurich (CH); MEMORIAL SLOAN KETTERING CANCER CENTER, New York, NY (US)

(72) Inventors: Marc Van Dijk, Bilthoven (NL); Cornelia Anne Mundt, Lorrach (DE); Gerd Ritter, New York, NY (US); Jedd David Wolchok, New York, NY (US); Taha Merghoub, Jersey City, NJ (US); Roberta Zappasodi, New York, NY (US); Rikke Baek Holmgaard, New York, NY (US); David Schaer, Mamaroneck, NY (US); David Adam Savitsky, Boxford, MA (US); Nicholas Stuart Wilson, Somerville, MA (US)

(73) Assignees: AGENUS INC., Lexington, MA (US); LUDWIG INSTITUTE FOR CANCER RESEARCH LTD, Zurich (CH); MEMORIAL SLOAN KETTERING CANCER CENTER, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/399,262

(22) Filed: Apr. 30, 2019

(65) Prior Publication Data
US 2019/0256601 A1 Aug. 22, 2019

Related U.S. Application Data

(63) Continuation of application No. 15/254,315, filed on Sep. 1, 2016, now Pat. No. 10,323,091.

(60) Provisional application No. 62/257,195, filed on Nov. 18, 2015, provisional application No. 62/216,043, filed on Sep. 9, 2015, provisional application No. 62/212,851, filed on Sep. 1, 2015.

(51) Int. Cl.
*C07K 16/28* (2006.01)
*A61K 39/395* (2006.01)
*A61K 39/00* (2006.01)

(52) U.S. Cl.
CPC ...... *C07K 16/2818* (2013.01); *C07K 16/2803* (2013.01); *A61K 2039/507* (2013.01); *C07K 2317/21* (2013.01); *C07K 2317/33* (2013.01); *C07K 2317/34* (2013.01); *C07K 2317/52* (2013.01); *C07K 2317/565* (2013.01); *C07K 2317/71* (2013.01); *C07K 2317/72* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,897,862 A | 4/1999 | Hardy et al. |
| 6,808,710 B1 | 10/2004 | Wood et al. |
| 7,029,674 B2 | 4/2006 | Carreno et al. |
| 7,332,582 B2 | 2/2008 | Hardy et al. |
| 7,521,051 B2 | 4/2009 | Collins et al. |
| 7,595,048 B2 | 9/2009 | Honjo et al. |
| 7,851,598 B2 | 12/2010 | Davis |
| 7,858,746 B2 | 12/2010 | Honjo et al. |
| 8,008,449 B2 | 8/2011 | Korman et al. |
| 8,168,757 B2 | 5/2012 | Finnefrock et al. |
| 8,354,509 B2 | 1/2013 | Carven et al. |
| 8,617,546 B2 | 12/2013 | Kang et al. |
| 8,735,553 B1 | 5/2014 | Li et al. |
| 8,741,295 B2 | 6/2014 | Olive |
| 8,927,697 B2 | 1/2015 | Davis et al. |
| 8,993,731 B2 | 3/2015 | Tyson |
| 9,067,998 B1 | 6/2015 | Clube et al. |
| 9,084,776 B2 | 7/2015 | Korman et al. |
| 9,102,727 B2 | 8/2015 | Freeman et al. |
| 9,132,281 B2 | 9/2015 | Zeng et al. |
| 9,163,087 B2 | 10/2015 | Huchroo et al. |
| 9,181,342 B2 | 11/2015 | Davis |
| 9,220,776 B2 | 12/2015 | Sharma et al. |
| 9,243,052 B2 | 1/2016 | Olive et al. |
| 9,358,289 B2 | 6/2016 | Korman et al. |

(Continued)

FOREIGN PATENT DOCUMENTS

| | | |
|---|---|---|
| EP | 1165616 B1 | 11/2004 |
| EP | 2133365 B1 | 12/2009 |

(Continued)

OTHER PUBLICATIONS

Feb. 28, 2016 Q4 2015 Results—Earnings Call Transcript.
(Continued)

*Primary Examiner* — Ilia I Ouspenski
(74) *Attorney, Agent, or Firm* — Lathrop Gage LLP; Andrew T. Wilkins

(57) ABSTRACT

The instant disclosure provides antibodies that specifically bind to human PD-1 and antagonize PD-1 function. Also provided are pharmaceutical compositions comprising these antibodies, nucleic acids encoding these antibodies, expression vectors and host cells for making these antibodies, and methods of treating a subject using these antibodies.

30 Claims, 17 Drawing Sheets

Figure 1A:
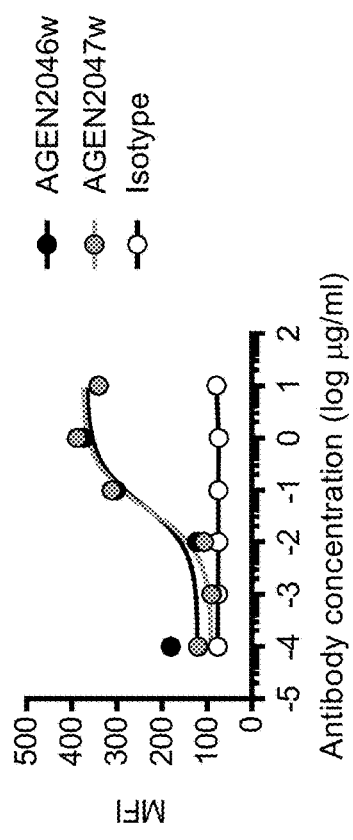

Specification includes a Sequence Listing.

(56) References Cited

U.S. PATENT DOCUMENTS

| | | |
|---|---|---|
| 9,381,244 B2 | 7/2016 | Noelle |
| 9,394,365 B1 | 7/2016 | Eisenbach-Schwartz et al. |
| 9,499,603 B2 | 11/2016 | Tyson |
| 9,580,504 B1 | 2/2017 | Rotem-Yehudar et al. |
| 9,605,070 B2 | 3/2017 | Sabatos-Peyton et al. |
| 9,676,853 B2 | 6/2017 | Zhou et al. |
| 9,683,048 B2 | 6/2017 | Freeman et al. |
| 9,701,749 B2 | 7/2017 | Shibayama et al. |
| 9,771,425 B2 | 9/2017 | Wang et al. |
| 9,815,898 B2 | 11/2017 | Freeman et al. |
| 10,323,091 B2 * | 6/2019 | van Dijk ............ C07K 16/2818 |
| 2003/0059937 A1 | 3/2003 | Ruben et al. |
| 2006/0246071 A1 | 11/2006 | Green et al. |
| 2008/0152587 A1 | 6/2008 | Zhou et al. |
| 2009/0155164 A1 | 5/2009 | Brasel et al. |
| 2011/0110956 A1 | 5/2011 | Rothe et al. |
| 2011/0177070 A1 | 7/2011 | Lofquist et al. |
| 2012/0121591 A1 | 5/2012 | Sullivan et al. |
| 2012/0195879 A1 | 8/2012 | Walker et al. |
| 2014/0234331 A1 | 8/2014 | Korman et al. |
| 2014/0302070 A1 | 10/2014 | Chen et al. |
| 2014/0356363 A1 | 12/2014 | Zhou et al. |
| 2015/0125463 A1 | 5/2015 | Cogswell et al. |
| 2015/0190506 A1 | 7/2015 | Cheung et al. |
| 2015/0202291 A1 | 7/2015 | Bosch et al. |
| 2015/0203579 A1 | 7/2015 | Papadopoulos et al. |
| 2015/0210769 A1 | 7/2015 | Freeman et al. |
| 2015/0216970 A1 | 8/2015 | Grogan et al. |
| 2015/0344577 A1 | 12/2015 | Fu |
| 2016/0032014 A1 | 2/2016 | Michaels et al. |
| 2016/0051672 A1 | 2/2016 | Stewart et al. |
| 2016/0075783 A1 | 3/2016 | King et al. |
| 2016/0090417 A1 | 3/2016 | Cogswell et al. |
| 2016/0108123 A1 | 4/2016 | Freeman et al. |
| 2016/0130345 A1 | 5/2016 | Fotin-Mleczek et al. |
| 2016/0130348 A1 | 5/2016 | Langermann et al. |
| 2016/0159905 A1 | 6/2016 | Abdiche et al. |
| 2016/0176963 A1 | 6/2016 | Maurer et al. |
| 2016/0208000 A1 | 7/2016 | Smythe |
| 2016/0222113 A1 | 8/2016 | Buchanan et al. |
| 2016/0222121 A1 | 8/2016 | Johnson et al. |
| 2016/0264667 A1 | 9/2016 | Chen et al. |
| 2016/0272708 A1 | 9/2016 | Chen |
| 2016/0280786 A1 | 9/2016 | Harmans et al. |
| 2016/0311904 A1 | 10/2016 | Haas et al. |
| 2016/0319018 A1 | 11/2016 | Morsey et al. |
| 2016/0319019 A1 | 11/2016 | Amirina et al. |
| 2016/0339090 A1 | 11/2016 | Hacohen et al. |
| 2016/0340428 A1 | 11/2016 | Yang |
| 2016/0347836 A1 | 12/2016 | Grosso |
| 2016/0355589 A1 | 12/2016 | Williams et al. |
| 2016/0362489 A1 | 12/2016 | Yang |
| 2016/0362492 A1 | 12/2016 | Freeman et al. |
| 2016/0376367 A1 | 12/2016 | Yuan et al. |
| 2017/0007693 A1 | 1/2017 | Weiner et al. |
| 2017/0037127 A1 | 2/2017 | Grogan et al. |
| 2017/0037132 A1 | 2/2017 | Manekas et al. |
| 2017/0044256 A1 | 2/2017 | Grogan et al. |
| 2017/0044259 A1 | 2/2017 | Tipton et al. |
| 2017/0044260 A1 | 2/2017 | Baruah et al. |
| 2017/0088613 A1 | 3/2017 | Grogan et al. |
| 2017/0088618 A1 | 3/2017 | Bennett et al. |
| 2017/0088626 A1 | 3/2017 | Jure-Kunkel et al. |
| 2017/0130271 A1 | 5/2017 | Wong |
| 2017/0158776 A1 | 6/2017 | Feltquate et al. |
| 2017/0165325 A1 | 6/2017 | Sharpe et al. |
| 2017/0166637 A1 | 6/2017 | Ben-Moshe et al. |
| 2017/0166642 A1 | 6/2017 | Pantaleo et al. |
| 2017/0174774 A1 | 6/2017 | Coric et al. |
| 2017/0210806 A1 | 6/2017 | Liu |
| 2017/0198039 A1 | 7/2017 | Wong |
| 2017/0209574 A1 | 7/2017 | Cao et al. |
| 2017/0218068 A1 | 8/2017 | Lesterhuis et al. |
| 2017/0239351 A1 | 8/2017 | Hamdy et al. |
| 2017/0240644 A1 | 8/2017 | Zhou et al. |
| 2017/0247454 A1 | 8/2017 | Benz et al. |
| 2017/0247455 A1 | 8/2017 | Jure-Kunkel et al. |
| 2017/0267760 A1 | 9/2017 | Diaz et al. |
| 2017/0267762 A1 | 9/2017 | Qiu et al. |

FOREIGN PATENT DOCUMENTS

| | | |
|---|---|---|
| EP | 2905030 A1 | 8/2015 |
| EP | 2906241 A1 | 8/2015 |
| EP | 2911669 A1 | 9/2015 |
| EP | 2931738 A1 | 10/2015 |
| EP | 2958588 B1 | 12/2015 |
| EP | 3036256 A1 | 6/2016 |
| EP | 3064220 A2 | 9/2016 |
| EP | 3160505 A1 | 5/2017 |
| WO | WO 2004072286 A1 | 1/2003 |
| WO | WO 2006121168 A1 | 11/2006 |
| WO | WO 2008156712 A1 | 12/2008 |
| WO | WO 2014179664 A2 | 11/2014 |
| WO | WO 2015181331 A1 | 12/2015 |
| WO | WO 2016077397 A2 | 5/2016 |
| WO | WO 2016120561 A2 | 6/2016 |
| WO | WO 2016127179 A2 | 8/2016 |
| WO | WO 2016137850 A1 | 9/2016 |
| WO | WO 2016137985 A1 | 9/2016 |
| WO | WO 2016149387 A1 | 9/2016 |
| WO | WO 2016168143 A1 | 10/2016 |
| WO | WO 2016172624 A1 | 10/2016 |
| WO | WO 2016179517 A1 | 11/2016 |
| WO | WO 2016183469 A1 | 11/2016 |
| WO | WO 2016196237 A1 | 12/2016 |
| WO | WO 2016196389 A1 | 12/2016 |
| WO | WO 2016205320 A1 | 12/2016 |
| WO | WO 2016210129 A1 | 12/2016 |
| WO | WO 2017016497 A1 | 2/2017 |
| WO | WO 2017019846 A1 | 2/2017 |
| WO | WO 2017024515 A1 | 2/2017 |
| WO | WO 2017054646 A1 | 4/2017 |
| WO | WO 2017055443 A1 | 4/2017 |
| WO | WO 2017055547 A1 | 4/2017 |
| WO | WO 2017058115 A1 | 4/2017 |
| WO | WO 2017059095 A1 | 4/2017 |
| WO | WO 2017079080 A1 | 5/2017 |
| WO | WO 2017079303 A1 | 5/2017 |
| WO | WO 2017087280 A1 | 5/2017 |
| WO | WO 2017087599 A1 | 5/2017 |
| WO | WO 2017096026 A1 | 6/2017 |
| WO | WO 2017103280 A1 | 6/2017 |
| WO | WO 2017107885 A1 | 6/2017 |
| WO | WO 2017124050 A1 | 7/2017 |
| WO | WO 2017125815 A2 | 7/2017 |
| WO | WO 2017129763 A1 | 8/2017 |
| WO | WO 2017129790 A1 | 8/2017 |
| WO | WO 2017132508 A1 | 8/2017 |
| WO | WO 2017132536 A1 | 8/2017 |
| WO | WO 2017133540 A1 | 8/2017 |
| WO | WO 2017147368 A1 | 8/2017 |
| WO | WO 2017151502 A1 | 9/2017 |
| WO | WO 2017151517 A1 | 9/2017 |
| WO | WO 2017160975 A1 | 9/2017 |
| WO | WO 2018106864 A1 | 6/2018 |

OTHER PUBLICATIONS

Aug. 3, 2017 Q2 2017 Results—Earnings Call Transcript.
Nov. 7, 2017 Q3 2017 Results—Earnings Call Transcript.
"A comprehensive immune-oncology Ecosystem" Cowen and Company 36th Annual Health Care Conference Mar. 2016.
Abdiche, Y.N., et al. (2016) "Assessing Kinetic and Epitopic Diversity Across Orthogonal Monoclonal Antibody Generation Platforms" mAbs, vol. 8, No. 2, pp. 264-277.
Afanasiev, O.K., et al., (2013) "Merkel Polyomavirus-Specific T Cells Fluctuate with Merkel Cell Carcinoma Burden and Express Therapeutically Targetable PD-1 and Tim-3 Exhaustion Markers" Clin. Cancer Res. 19(19):5351-60.
Agata, Y. et al., (1996) "Expression of the PD-1 antigen on the surface of stimulated mouse T and B lymphocytes." Int. Immunol 8:765-72.

(56) References Cited

OTHER PUBLICATIONS

"Agenus Announces Combination Clinical Trials of its Anti-CTLA4 (AGEN1884) & Anti-PD1 (AGEN2034)" Jan. 22, 2018 /PRNewswire/.
"Agenus Commences Phase I Clinical trials of its CTLA-4 Checkpoint Antibody to Treat Solid Tumors," Apr. 27, 2016 /Business Wire/.
"Agenus Investor Relations Deck" May 15, 2015.
"Agenus IR Deck" Dec. 2016.
"Agenus IR Presentation" Aug. 2016.
Agenus News vol. 1 Issue 1 (2018).
Agenus News vol. 1 Issue 2 (2018).
Agenus News vol. 1 Issue 3 (2018).
Agenus News vol. 1 Issue 8 (2018).
"Agenus Inc. Closes $230 Million Royalty Monetization with HealthCare Royalty Partners" Jan. 22, 2018 /PRNewswire/.
"Agenus Presents Clinical Responses of AGEN1884 (anti-CTLA-4) and AGEN2034 (anti-PD-1) at ASCO 2018" Jun. 4, 2018 /PRNewswire/.
"Agenus Presents Posters on Checkpoint Antibody Product Candidates at the American Association for Cancer Research (AACR) 2016 Annual Meeting" Apr. 18, 2016 (Business Wire).
"Agenus R&D Day" Nov. 19, 2015 New York, NY.
"Agenus Roadshow Slide Deck" May 15, 2015.
"Agenus Roadshow Slide Deck" Aug. 2016.
"Agenus to Present Clinical Data on Lead Programs at ASCO 2018" May 17, 2018 /PRNewswire/.
"Agenus to Present on Lead Antibody Programs AGEN1884 (CTLA-4) and AGEN2034 (PD-1) at SITC 2017" Nov. 9, 2017 /PRNewswire/.
"Agenus Background Slide Deck" Jan. 2017.
Ahmadzadeh, M., et al., (2009) "Tumor antigen-specific CD8 T cells infiltrating the tumor express high levels of PD-1 and are functionally impaired" Blood 114:1537-1544.
Allie, S.R., et al., (2011) "Programmed death 1 regulates development of central memory CD8 T cells after acute viral infection" J. Immunol. 186:6280-6286.
Anonymous (2014) "International Nonproprietary Names for Pharmaceutical Substances (INN)," WHO drug Information Rec. Wld Health Org. Resolution EB15.R7), pp. 1-44. [retrieved on Nov. 7, 2016].
Antonia, S., et al., (2016) "Safety and antitumour activity of durvalumab plus tremelimumab in non-small cell lung cancer: a multicentre, phase 1b study" The Lancet Oncology 17(3):299-308.
Antonia, S.J., et al., (2016) "Nivolumab alone and nivolumab plus ipilimumab in recurrent small-cell lung cancer (CheckMate 032): a multicentre, open-label, phase 1/2 trial" The Lancet Oncology 17(7):883-895.
Attia, P., et al., (2005) "Autoimmunity Correlates With Tumor Regression in Patients With Metastatic Melanoma Treated With Anti—Cytotoxic T-Lymphocyte Antigen-4" Journal of Clinical Oncology 23:6043-6053.
Bally, A.P., et al., (2015) "NF-κB regulates PD-1 expression in macrophages" J. Immunol. 194:4545-4554.
Barber, D.L., et al., (2006) "Restoring function in exhausted CD8 T cells during chronic viral infection" Nature 439:682-687.
Baruch, K., et al., (2016) "PD-1 immune checkpoint blockade reduces pathology and improves memory in mouse models of Alzheimer's disease" Nature Med. 22(2):135-7.
Bauml et al (2016) "Preliminary results from KEYNOTE-055: Pembrolizumab after platinum and cetuximab failure in head and neck squamous cell carcinoma (HNSCC)" 2016 ASCO Annual Meeting: J Clin Oncol 34, 2016 (suppl; abstr 6011).
Bennett, F., et al., (2003) "Program death-1 engagement upon TCR activation has distinct effects on costimulation and cytokine-driven proliferation: attenuation of ICOS, IL-4, and IL-21, but not CD28, IL-7, and IL-15 responses" J. Immunol. 170:711-718.
Benson, D M et al. (2010) "The PD-1/PD-L1 axis modulates the natural killer cell versus multiple myeloma affect: a therapeutic target for CT-011, a novel monoclonal anti-PD-1 antibody," Blood, American Society of Hemotology, US 116(13):2286-2294.
Bifulco, C.B., et al., (2016) "Unmasking PD-1 Resistance by Next-Generation Sequencing" N. Engl. J. of Med. 375(9):888-889.

Blank, C., et al., (2004) "PD-L1/B7H-1 inhibits the effector phase of tumor rejection by T cell receptor (TCR) transgenic CD8+ T cells" Cancer Res. 64:1140-1145.
Blank, C., et al., (2005) "Interaction of PD-L1 on tumor cells with PD-1 on tumor-specific T cells as a mechanism of immune evasion: implications for tumor immunotherapy" Cancer Immunol. Immunother. 54:307-314.
Blank, C., et al., (2007) "Contribution of the PD-L1/PD-1 pathway to T-cell exhaustion: an update on implications for chronic infections and tumor evasion" Cancer Immunol. Immunother. 56:739-745.
Borcoman, E. et al. (2017) "Pembrolizumab in cervical cancer: latest evidence and clinical usefulness," Ther Adv Med Oncol. 9(6):431-439.
Borradori, L. et al., (2016) "Rescue therapy with anti-programmed cell death protein 1 inhibitors of advanced cutaneous squamous cell carcinoma and basosquamous carcinoma: preliminary experience in five cases" The British Journal of Dermatology, 175(6):1382-1386.
Boussiotis, V.A., et al., (2016) "Molecular and Biochemical Aspects of the PD-1 Checkpoint Pathway" N. Engl. J. Med. 375(18):1767-78.
Boutros, C., et al., (2016) "Safety profiles of anti-CTLA-4 and anti-PD-1 antibodies alone and in combination" Nature Reviews 13:473.
Boyd, S.D., et al. (2016) "Deep Sequencing and Human Antibody Repertoire Analysis" Current Opinion in Immunology, vol. 40, pp. 103-109.
Brahmer, J.R., et al., (2010) "Phase I Study of Single-Agent Anti-Programmed Death-1 (MDX-1106) in Refractory Solid Tumors: Safety, Clinical Activity, Pharmacodynamics, and Immunologic Correlates" J. Clin. Oncol. 28(19):3167-75.
Brahmer, J.R., et al., (2012) "Safety and activity of anti-PD-L1 antibody in patients with advanced cancer" N. Engl. J. Med. 366:2455-2465.
Brantsch, K.D. et al., (2008) "Analysis of risk factors determining prognosis of cutaneous squamous-cell carcinoma: a prospective study" The Lancet Oncology 9(8):713-720.
Bristol-Myers Squibb USA, 2015. Yervoy® (ipilimumab) package insert.
Bristol-Myers Squibb USA, 2016. Opdivo® (nivolumab) package insert.
Brougham, N.D.L.S., et al., (2012) "The incidence of metastasis from cutaneous squamous cell carcinoma and the impact of its risk factors" Journal of Surgical Oncology 106(7):811-815.
Brown, J.A., et al., (2003) "Blockade of programmed death-1 ligands on dendritic cells enhances T cell activation and cytokine production" J. Immunol. 170:1257-66.
Buchbinder, E.I., et al., (2016) "CTLA-4 and PD-1 Pathways: Similarities, Differences, and Implications of Their Inhibition" American Journal of Clinical Oncology, 39(1):98-106.
Bulliard, Y., et al., (2013) "Activating Fcγ receptors contribute to the antitumor activities of immunoregulatory receptor-targeting antibodies" The Journal of Experimental Medicine 210(9):1685-1693.
Burova, E. et al. (2017) "Characterization of the anti-PD-1 antibody REGN2810 and its antitumor activity in human PD-1 knock-in mice," Mol. Cancer Ther. 16(5): 861-870.
Butte, M.J., et al., (2007) "Programmed death-1 ligand 1 interacts specifically with the B7-1 costimulatory molecule to inhibit T cell responses" Immunity 27:111-122.
Callahan, M.K., et al., (2014) "CTLA-4 and PD-1 Pathway Blockade: Combinations in the Clinic" Front. Oncol. 4(385):1-6.
Camacho, L.H., (2015) "CTLA-4 blockade with ipilimumab: biology, safety, efficacy, and future considerations" Cancer Medicine 4(5):661-672.
Carrizosa et al., (2013) "New targets and new mechanisms in lung cancer." Oncology 27(5).
Carter, L. et al. (2003) "Cytotoxic T-lymphocyte antigen-4 and programmed death-1 function as negative regulators of lymphocyte activation," Immunol Res 28(1):49-59.
Carter, L., et al., (2002) "PD-1:PD-L inhibitory pathway affects both CD4(+) and CD8(+) T cells and is overcome by IL-2" Eur. J. Immunol. 32:634-43.

(56) References Cited

OTHER PUBLICATIONS

Casey, S.C., et al., (2016) "MYC regulates the antitumor immune response through CD47 and PD-L1" Science 352:227-231.
Chaft, J.E., (Mar. 30, 2017) "Immunotherapy for lung cancer and the landscape of combinations" Thoracis Oncology Service Memorial Sloan Kettering Cancer Center.
Chand, D., et al., "AGEN2034, a novel anti-PD-1 antibody that combines effectively with CTLA-4 pathway blockade to enhance T cell activity" Poster #P312 SITC Annual Meeting, Washington, DC, USA Nov. 9-12, 2017.
Chapman, K., (2007) "Preclinical safety testing of monoclonal antibodies: the significance of species relevance" Nat. Rev. Drug Discov. 6:120-126.
Chapon, M., et al., (2011) "Progressive upregulation of PD-1 in primary and metastatic melanomas associated with blunted TCR signaling in infiltrating T lymphocytes" J. Invest. Dermatol. 131:1300-1307.
Chauvin, J., et al., (2015) "TIGIT and PD-1 impair tumor antigen—specific CD8+ T cells in melanoma patients" 125(5):2046-58.
Chemnitz, J.M., et al., (2004) "SHP-1 and SHP-2 associate with immunoreceptor tyrosine-based switch motif of programmed death 1 upon primary human T cell stimulation, but only receptor ligation prevents T cell activation" J. Immunol. 173:945-954.
Chen, L., et al., (2015) "Anti-PD-1/PD-L1 therapy of human cancer: past, present, and future" J. Clin. Invest. 125:3384-3391.
Chen, S., et al., (2015) "Combination of 4-1BB agonist and PD-1 antagonist promotes antitumor effector/memory CD8 T cells in a poorly immunogenic tumor model" Cancer Immunol. Res. 3(2):149-160.
Chu, F., et al., (2014) "Anti-PD-1 antibodies for the treatment of B-cell lymphoma Importance of PD-1+ T-cell subsets" OncoImmunology 3(e28101):1-3.
Chung, C.H., (2008) "Managing Premedications and the Risk for Reactions to Infusional Monoclonal Antibody Therapy" The Oncologist 13:725-732.
Collins, A.V., et al., (2002) "The interaction properties of costimulatory molecules revisited" Immunity 17:201-210.
Collins, M., et al., (2005) "The B7 family of immune-regulatory ligands" Genome Biology 6(6):223.1-223.7.
Conroy, P.J., et al. (2017) "Antibodies: From Novel Repertoires to Defining and Refining the Structure of Biologically Important Targets" Methods, vol. 116, pp. 12-22.
Coyne, G.O., et al., (2014) "Nivolumab: Promising Survival Signal Coupled With Limited Toxicity Raises Expectations" J. Clin. Oncol. 32(10):986-988.
Cross, R.S., et al., (2015) "Therapeutic DNA vaccination against colorectal cancer by targeting the MYB oncoprotein" Clin. Transl. Immunol. 4:e30.
Curran, M.A., et al., (2010) "PD-1 and CTLA-4 combination blockade expands infiltrating T cells and reduces regulatory T and myeloid cells within B16 melanoma tumors" Proc. Natl. Acad. Sci. USA 107:4275-4280.
Currie, A.J., et al., (2009) "Dual Control of Antitumor CD8 T Cells through the Programmed Death-1/Programmed Death-Ligand 1 Pathway and Immunosuppressive CD4 T Cells: Regulation and Counterregulation" J. Immunol. 183:7898-08.
Da Silva, R M et al. (2014) "Nivolumab: Anti-PD-1 monoclonal antibody cancer immunotherapy," Drugs of the Future, 39(1):15-24.
Dahan, R., (2015) "FcγRs Modulate the Anti-tumor Activity of Antibodies Targeting the PD-1/PD-L1 Axis." Cancer Cell 28(3):285-295.
Das, R., et al., (2015) "Combination therapy with anti-CTLA-4 and anti-PD-1 leads to distinct immunologic changes in vivo" J. Immunol. 194:950-959.
De Souza, P., et al., "Evaluation of Peripheral T-Cell Subset Proliferation as a Pharmacodynamic Assay to Guide the Development of Anti-CTLA-4 and PD-1 Antibody Combinations in Patients With Solid Tumors" CT104 Presented at the 2018 Annual Meeting of the American Association of Cancer Research, Apr. 14-18, 2018, in Chicago, IL, USA.

Demaria, S., et al., (2005) "Combining radiotherapy and immunotherapy: A revived partnership" International J. of Radiation Oncology Biology Physics 63(3):655-666.
Deng, L., et al., (2014) "Irradiation and anti-PD-L1 treatment synergistically promote antitumor immunity in mice" J. Clin. Invest. 124(2):687-695.
Disis, M.L. (2010) "Immune regulation of cancer" J. Clin. Oncol. 28:4531-4538.
Dolan, D.E., et al., (2014) "PD-1 Pathway Inhibitors: Changing the Landscape of Cancer Immunotherapy" Cancer Control 21(3):231-7.
Dong, H., et al., (2002) "Tumor-associated B7-H1 promotes T-cell apoptosis: a potential mechanism of immune evasion" Nat. Med. 8:787-9.
Dong, H., et al., (2003) "B7-H1 pathway and its role in the evasion of tumor immunity." J. Mol. Med. 81:281-7.
Drescher, C., et al., "Phase 1/2, Open-Label, Multiple Ascending Dose Trial of AGEN2034, an Anti—PD-1 Monoclonal Antibody, in Advanced Solid Malignancies: Results of Dose Escalation in Advanced Cancer and Expansion Cohorts in Subjects With Relapsed/Refractory Cervical Cancer" Poster No. 1158P Presented at European Society for Medical Oncology, Munich, Germany (2018).
Drouin, E., et al., "AGEN1884 and AGEN2041: Two functionally distinct anti-CTLA-4 antagonist antibodies" Poster No. #5005 Presented at the American Association for Cancer Research Annual Meeting 2016 New Orleans, LA, USA, Wednesday, Apr. 20, 2016.
Drouin, E., et al., "AGEN1884, an IgG1 anti-CTLA-4 antibody, combines effectively with PD-1 blockade in primary human T cell assays and in a non-human primate pharmacodynamic (PD) model" Poster: #27 Abstract: #3654 AACR Annual Meeting 2017, Washington, DC, USA Apr. 1-5, 2017.
Dudley, J.C., et al., (2016) "Microsatellite Instability as a Biomarker for PD-1 Blockade" Clin. Cancer Res. 22(4):813-20.
Duraiswamy, J., et al., (2013) "Dual Blockade of PD-1 and CTLA-4 Combined with Tumor Vaccine Effectively Restores T-Cell Rejection Function in Tumors" Cancer Res. 73(12):3591-603.
Duraiswamy, J., et al., (2013) "Therapeutic PD-1 pathway blockade augments with other modalities of immunotherapy T-cell function to prevent immune decline in ovarian cancer" Cancer Res. 73(23):6900-6912.
Dyck, L., et al., (2016) "Anti-PD-1 inhibits Foxp3+ Treg cell conversion and unleashes intratumoural effector T cells thereby enhancing the efficacy of a cancer vaccine in a mouse model" Cancer Immunol. Immunother. 65(12):1491-1498.
Eisenhauer, E.A., et al., (2009) "New response evaluation criteria in solid tumours: Revised RECIST guideline (version 1.1)" European Journal of Cancer 45:228-247.
"Emerging Leader in Immuno-Oncology" Nov. 2015, Lexington, MA.
"Enabling Best-in-Class I-O Combinations" Mar. 2018.
Evans, T.A., et al., (2010) "Functional diversity of Robo receptor immunoglobulin domains promotes distinct axon guidance decisions" Curr. Biol. 20:567-572.
Falchook, G.S., et al., (2016) "Responses of metastatic basal cell and cutaneous squamous cell carcinomas to anti-PD1 monoclonal antibody REGN2810" Journal for Immunotherapy of Cancer 4(1):70.
Ferrara, F., et al. (2015) "Recombinant Renewable Polyclonal Antibodies", mAbs, vol. 7 No. 1, pp. 32-41.
Ferris, R.K., et al., (2016) "Nivolumab for Recurrent Squamous-Cell Carcinoma of the Head and Neck" N. Engl. J. Med. 375(19):1856-1867.
Finco, D., et al., (2014) "Cytokine release assays: current practices and future directions" Cytokine 66:143-155.
Foote, M.C. et al., (2014) "Phase II study of single-agent panitumumab in patients with incurable cutaneous squamous cell carcinoma" Annals of Oncology, 25(10):2047-2052.
Four Agenus Abstracts Accepted for Presentation at the American Association for Cancer Research (AACR) 2017 Annual Meeting Mar. 7, 2017 /PRNewswire/.
Francisco, L.M., et al., (2010) "The PD-1 pathway in tolerance and autoimmunity" Immunol. Rev. 236:219-242.
Frazier, K.S., et al., (2015) "Scientific and Regulatory Policy Committee Points-to-consider Paper: Drug-induced Vascular Injury

(56) References Cited

OTHER PUBLICATIONS

Associated with Nonsmall Molecule Therapeutics in Preclinical Development: Part I. Biotherapeutics" Toxicol. Pathol. 43:915-934.
Freeman, G.J et al. (2000) "Engagement of the PD-1 immunoinhibitory receptor by a novel B7 family member leads to negative regulation of lymphocyte activation" J. Exp. Med. 192:1027-1034.
Freeman, G.J., et al. (2006) "Reinvigorating exhausted HIV-specific T cells via PD-1-PD-1 ligand blockade" J. Exp. Med. 203:2223-2227.
Frenel, J.-S., et al., (2016) "Pembrolizumab in patients with advanced cervical squamous cell cancer: Preliminary results from the phase Ib KEYNOTE-028 study" J. Clin. Oncol. 34 (suppl), Abstract 5515.
Fu, J., et al., (2014) "Preclinical Evidence That PD1 Blockade Cooperates with Cancer Vaccine TEGVAX to Elicit Regression of Established Tumors" Cancer Res; 74(15):4042-52.
Garcia-Sanz, J.A., et al. (1996) "Translational control of interleukin 2 messenger RNA as a molecular mechanism of T cell anergy" J. Exp. Med. 184:159-164.
Gatalica, Z., et al., (2014) "Programmed Cell Death 1 (PD-1) and Its Ligand (PD-L1) in Common Cancers and Their Correlation with Molecular Cancer Type" Cancer Epidemiol Biomarkers Prev. 23(12); 2965-70.
Ge, Y., et al., (2013) "Blockade of PD-1/PD-L1 immune checkpoint during DC vaccination induces potent protective immunity against breast cancer in hu-SCID mice" Cancer Letters 336:253-259.
George, S. et al. (2017) "Loss of PTEN is associated with resistance to anti-PD-1 checkpoint blockade therapy in metastatic uterine leiomyosarcoma," Immunity. 46:197-204.
Ghebeh, H., et al., (2006) "The B7-H1 (PD-L1) T lymphocyte-inhibitory molecule is expressed in breast cancer patients with infiltrating ductal carcinoma: correlation with important high-risk prognostic factors" Neoplasia 8:190-198.
Ghiotto, M., et al., (2010) "PD-L1 and PD-L2 differ in their molecular mechanisms of interaction with PD-1" International Immunology 22(8):651-60.
Goldman, JW et al. (2017) "Nivolumab (N) plus Ipillimub (I) as first-line (1L) treatment for advanced (adv) NSCLC: 2-yr OS and long-term outcome from CheckMate 012," J Clin Oncol. 35(15): 4 pp.
Gonzalez, A., et al., "INCAGN1949, an Anti-OX40 Antibody With an Optimal Agonistic Profile and the Ability to Selectively Deplete Intratumoral Regulatory T Cells" 4703 Presented at the American Association for Cancer Research Annual Meeting 2017; Washington, DC, USA Apr. 1-5, 2017.
Gonzalez, et al., "INCAGN1876, a Unique GITR Agonist Antibody That Facilitates GITR Oligomerization" 3643 Presented at the American Association for Cancer Research Annual Meeting 2017, Washington, DC, USA Apr. 1-5, 2017.
Gooden, M.J., et al., (2011) "The prognostic influence of tumour-infiltrating lymphocytes in cancer: a systematic review with meta-analysis" Br. J. Cancer 105:93-103.
Gooden, M. et al. (2011) "HLA-E expression by gynecological cancers restrains tumor-infiltrating CD8+ T lymphocytes," PNAS 108(26):10656-10661.
Gros, A., et al., (2014) "PD-1 identifies the patient-specific CD8+ tumor-reactive repertoire infiltrating human tumors" Journal of Clinical Investigation 124(5):2246.
Grosso, J.F., et al., (2013) "CTLA-4 blockade in tumor models: an overview of preclinical and translational research" Cancer Immun. 13(5).
"Guideline on immunogenicity assessment of monoclonal antibodies intended for in vivo clinical use," European Medicines Agency, London, UK, 2012.
Hamanishi, J., et al., (2007) "Programmed cell death 1 ligand 1 and tumor infiltrating CD8+ T lymphocytes are prognostic factors of human ovarian cancer" Proc. Nat. Acd. Sci. USA 104(9):3360-5.
Hamid, O., et al. (2013) "Safety and tumor responses with lambrolizumab (anti-PD-1) in melanoma" N. Engl. J. Med. 369:134-144.

Haymaker, C., et al., (2012) "PD-1 and BTLA and CD8+ T-cell "exhaustion" in cancer "Exercising" an alternative viewpoint" Oncolmmunology 1(5):735-8.
Hellmann, M.D., et al., (2016) CheckMate 012: safety and efficacy of first-line nivolumab and ipilimumab in advanced NSCLC In ASCO Annual Meeting. Chicago: Proc Am Soc Clin Oncol.
Hirano, F. et al. (2005) "Blockade of B7-H1 and PD-1 by Monoclonal Antibodies Potentiates Cancer Therapeutic Immunity," Cancer Res 65(3):1089-1096.
Hodi, F.S., et al., (2014) "Long-term survival of ipilimumab-naive patients (pts) with advanced melanoma (MEL) treated with nivolumab (anti-PD-1, BMS-936558, ONO-4538) in a phase I trial" ASCO.
Howard, S.C., et al., (2011) "The Tumor Lysis Syndrome" N. Engl. J. Med. 364(19):1844-1854.
Huang, R., et al., (2015) "LAG3 and PD1 co-inhibitory molecules collaborate to limit CD8+ T cell signaling and dampen antitumor immunity in a murine ovarian cancer model" Oncotarget 6(29):27359-77.
Ichigotani, Y., et al., (2000) "Molecular cloning of a novel human gene (SIRP-B2) which encodes a new member of the SIRP/SHP S-1 protein family" J. Hum. Genet. 45:378-382.
"Integrated Approach to Immuno-oncology" Mar. 31, 2016.
"Integrated Immunotherapy: Enabling Best-in-Class 1-O combinations" Feb. 2017.
"Integrated Immunotherapy: Enabling Best-in-Class 1-O Combinations" Jan. 2018.
"Integrated Immunotherapy: Enabling Best-in-Class I-O Combinations" Jun. 2018.
"Integrated Immunotherapy: Enabling Best-in-Class I-O Combinations" Mar. 2018.
"Integrated Immunotherapy: Enabling Best-in-Class I-O Combinations" Nov. 2017.
"Integrated Solutions in Immuno-Oncology" Apr. 2016.
"Integrated Solutions in Immuno-Oncology" May 2016.
International Search report for PCT/US2016/049913 dated Jan. 20, 2017.
Intlekofer, A., et al., (2013) "At the Bench: preclinical rationale for CTLA-4 and PD-1 blockade as cancer immunotherapy" J. of Leukocyte Biol. 94:25-39.
Ishida M, et al., (2002) "Differential expression of PD-L1 and PD-L2, ligands for an inhibitory receptor PD-1, in the cells of lymphohematopoietic tissues" Immunol. Lett. 84(1):57-62.
Ishida, Y., et al., (1992) "Induced expression of PD-1, a novel member of the immunoglobulin gene superfamily, upon programmed cell death" Embo J. 11:3887-3895.
Iwai, Y. et al. (2003) "PD-1 inhibits antiviral immunity at the effector phase in the liver," J Exp Med 198(1):39-50.
Iwai, Y., et al. (2002) "Involvement of PD-L1 on tumor cells in the escape from host immune system and tumor immunotherapy by PD-L1 blockade" Proc. Natl. Acad. Sci. USA 99:12293-12297.
Iwai, Y., et al., (2002) "Microanatomical localization of PD-1 in human tonsils" Immunol. Lett. 83:215-220.
Jarkowski, A., et al., (2016) "Systemic Therapy in Advanced Cutaneous Squamous Cell Carcinoma (CSCC): The Roswell Park Experience and a Review of the Literature" American Journal of Clinical Oncology, 39(6):545-548.
Jawad, Z., "Targeting the next generation of checkpoint pathways using a disease-centric approach" ICI Europe Meeting Nov. 16-17, 2016.
Jin, H., et al., (2010) "Role of PD-1 in Regulating T-Cell Immunity" Current Topics in Microbiology and Immunology 350:17-36.
John, L.B., et al., (2013) "Anti-PD-1 Antibody Therapy Potently Enhances the Eradication of Established Tumors by Gene-Modified T Cells" Clin. Cancer Res. 19(20):5636-46.
John, L.B., et al., (2013) "Blockade of PD-1 immunosuppression boosts CAR T-cell therapy" Oncolmmunology 2(10):e26286-1-3.
Kamphorst, A.O., et al., (2013) "Manipulating the PD-1 pathway to improve immunity" Current Opinion in Immunology 25:381-388.
Karia, P.S., et al., (2013) "Cutaneous squamous cell carcinoma: estimated incidence of disease, nodal metastasis, and deaths from disease in the United States, 2012" Journal of the American Academy of Dermatology 68(6):957-966.

(56) References Cited

OTHER PUBLICATIONS

Kaufman, H., et al., (2016) "Avelumab (MSB0010718C; anti-{D-1) in patients with metastatic Merkel cell carcinoma previously treated with chemotherapy: results of the phase 2 JAVELIN Merkel 200 trial" Oral Presentation at the 52nd ASCO Annual Meeting Jun. 307 Chicago, IL Abstract No. 9508.
Keir, M.E., et al., (2005) "Programmed Death-1 (PD-1):PD-Ligand 1 Interactions Inhibit TCR-Mediated Positive Selection of Thymocytes" The Journal of Immunology 175:7372-7379.
Keir, M.E., et al., (2008) "PD-1 and Its Ligands in Tolerance and Immunity" Annu. Rev. Immunol. 26:677-704.
Kelderman, S., et al., (2015) "Mismatch Repair-Deficient Cancers Are Targets for Anti-PD-1 Therapy" Cancer Cell 28:11-13.
Khan, L., et al. (2017) "Cross-Neutralizing Anti-HIV-1 Human Single Chain Variable Fragments(scFvs) Against CD4 Binding Site and N332 Glycan Identified from a Recombinant Phage Library" Scientific Reports, vol. 7, Article No. 45163, 12 Pages.
Kinter, A.L., et al., (2008) "The common gamma-chain cytokines IL-2, IL-7, IL-15, and IL-21 induce the expression of programmed death-1 and its ligands" J. Immunol. 181:6738-6746.
Kleffel, S., et al., (2015) "Melanoma Cell-Intrinsic PD-1 Receptor Functions Promote Tumor Growth." Cell 162(6): 1242-1256.
Konishi, J., et al., (2004) "B7-H1 expression on non-small cell lung cancer cells and its relationship with tumor-infiltrating lymphocytes and their PD-1 expression" Clin. Cancer Res. 10:5094-100.
Konitzer, J.D., et al. (2017) "Generation of a Highly Diverse Panel of Antagonistic Chicken Monoclonal Antibodies Against the GIP Receptor" mAbs, vol. 9, No. 3, pp. 536-549.
Larkin, J., et al., (2015) "Combined Nivolumab and Ipilimumab or Monotherapy in Untreated Melanoma" New England Journal of Medicine 373(1):23-34.
Latchman, Y., et al., (2001) "PD-L2 is a second ligand for PD-1 and inhibits T cell activation" Nat. Immunol. 2:261-8.
Le, D.T., et al., (2015) "PD-1 Blockade in Tumors with Mismatch-Repair Deficiency" N. Engl. J. Med. 372:2509-2520.
Leach, M.W., et al. (2010) "Use of tissue cross-reactivity studies in the development of antibody-based biopharmaceuticals: history, experience, ethodology, and future directions" Toxicol. Pathol. 38:1138-1166.
Leach, M.W., et al., (2014) "Immunogenicity/hypersensitivity of biologics" Toxicol. Pathol. 42:293-300.
Leach, S., "Immune Checkpoint Inhibitors: Response rates in solid tumors" 2018 Gastrointestinal Cancers Symposium.
Le Tourneau, C., et al., (2009) "Dose Escalation Methods on Phase I Cancer Clinical Trials" J. Natl. Cancer Inst. 101:708-720.
Lee, J., et al. (2016) "Molecular-Level Analysis of the Serum Antibody Repertoire in Young Adults Before and After Seasonal Influenza Vaccination" Nature Medicine, vol. 22, No. 12, pp. 1456-1464.
Li, B., (2009) "Anti-Programmed Death-1Synergizes with Granulocyte Macrophage Colony-Stimulating Factor—Secreting Tumor Cell Immunotherapy roviding Therapeutic Benefit to Mice with Established Tumors" Clin Cancer Res 1623 2009;15(5).
Lin, D.Y., et al., (2008) "The PD-1/PD-L1 complex resembles the antigen-binding Fv domains of antibodies and T cell receptors" Proc. Natl. Acad. Sci. USA 105:3011-3016.
Lin, E.I., et al., (2015) "Mutational profiling of colorectal cancers with microsatellite Instability" Oncotarget 6(39):42334-44.
Lin, Y.M., et al., (2015) "High PD-L1 Expression Correlates with Metastasis and Poor Prognosis in Oral Squamous Cell Carcinoma" PLoS One 10:e0142656.
Liu, L., et al. (2015) "The BRAF and MEK Inhibitors Dabrafenib and Trametinib: Effects on Immune Function and in Combination with Immunomodulatory Antibodies Targeting PD-1, PD-L1, and CTLA-4" Clin. Cancer Res. 21:1639-1651.
Liu, X., et al., (2003) "B7DC/PDL2 Promotes Tumor Immunity by a PD-1-independent Mechanism" J. Exp. Med. 197(12):1721-30.
Li-Weber, M., (2003) "Regulation of IL4 Gene Expression by T Cells and Therapeutic Perspectives" Nature Reviews 3:534.

Li-Weber, M., et al., (2003) "Function and regulation of the CD95 (APO-1/Fas) ligand in the immune system" Semin. Immunol. 15:145-157.
Loke, P., et al., (2003) "PD-L1 and PD-L2 are differentially regulated by Th1 and Th2 cells" Proc. Natl. Acad. Sci. USA 100(9):5336-5341.
Long, G.V., et al., (2016) "Pembrolizumab (pembro) plus ipilimumab (ipi) for advanced melanoma: Results of the KEYNOTE-029 expansion cohort" Journal of Clinical Oncology, 34(15 suppl.):9506-9506.
Lote, H., et al., (2015) "PD-1 and PD-L1 blockade in gastrointestinal malignancies" Cancer Treatment Reviews 41:893-903.
Lowther, D.E., et al. (2016) "PD-1 marks dysfunctional regulatory T cells in malignant gliomas" 1(5):e85935.
Luke, J.J., et al., (2015) "PD-1 pathway inhibitors: The next generation of immunotherapy for advanced melanoma" Oncotarget 6(6):3479-92.
Macfarlane, A.W., et al., (2013) "PD-1 Expression on Peripheral Blood Cells Increases with Stage in Renal Cell Carcinoma Patients and Is Rapidly Reduced after Surgical Tumor Resection" Cancer Immunol Res; 2(4):320-31.
Macian, F. (2005) "NFAT proteins: key regulators of T-cell development and function" Nat. Rev. Immunol. 5:472-484.
Mahoney, K.M., et al., (2015) "The Next Immune-Checkpoint Inhibitors: PD-1/PD-L1 Blockade in Melanoma" Clin. Ther. 37:764-782.
Mamalis, A., et al., (2014) "Targeting the PD-1 Pathway: A Promising Future for the Treatment of Melanoma" Arch Dermatol Res. 306(6): 511-519.
Mangsbo, S.M., et al., (2010) "Enhanced Tumor Eradication by Combining CTLA-4 or PD-1 Blockade With CpG Therapy" J. Immunother. 33:225-235.
Marabelle, A. et al., (2013) "Depleting tumor-specific Tregs at a single site eradicates disseminated tumors" The Journal of Clinical Investigation 123(6):2447-2463.
Marzec, M., et al., (2008) "Oncogenic kinase NPM/ALK induces through STAT3 expression of immunosuppressive protein CD274 (PD-L1, B7-H1)" Proc. Natl. Acad. Sci. USA 105:20852-20857.
Matsuzaki, K., et al., (2010) "Tumor-infiltrating NY-ESO-1-specific CD8+ T cells are negatively regulated by LAG-3 and PD-1 in human ovarian cancer" Proc. Nat'l. Acad. Sci. USA 107(17):7875-7880.
Mcdermott, D.F., et al., (2011) "A phase I study to evaluate safety and antitumor activity of biweekly BMS-936558 (Anti-PD-1, MDX-1106/ONO-4538) in patients with RCC and other advanced refractory malignancies" J. Clin. Oncol. 29 (7 suppl. abstr 331).
Mcdermott, J. et al. (2015) "Pembrolizumab: PD-1 inhibition as a therapeutic strategy in cancer," Drugs of Today, 15(1):7-20.
Meng, X., et al., (2015) "Predictive biomarkers in PD-1/PD-L1 checkpoint blockade immunotherapy" Cancer Treatment Reviews 41(10):868-76.
Mezache, L., et al., (2015) "Enhanced expression of PD L1 in cervical intraepithelial neoplasia and cervical cancers" Modern Pathology 28(12):1594-1602.
Min, L., et al., (2013) "Anti-PD1 Following Ipilimumab for Mucosal Melanoma: Durable Tumor Response Associated with Severe Hypothyroidism and Rhabdomyolysis" Cancer Immunol. Res. 2(1):15-18.
Mittal, D., et al., (2014) "Antimetastatic effects of blocking PD-1 and the adenosine A2A receptor" Cancer Res. 74:3652-3658.
Mkrtichyan, M., et al., (2011) "Anti-PD-1 synergizes with cyclophosphamide to induce potent anti-tumor vaccine effects through novel mechanisms" Eur. J. Immunol. 41:2977-2986.
Moore, K.N., et al., "Phase 1/2 Open-Label, Multiple Ascending Dose Trial of AGEN2034, an anti-PD-1 Monoclonal Antibody, in Advanced Solid Malignancies: Results of Dose Escalation" 18/1200-B ASCO C-700-01, 230933 (2018) J Clin Oncol 36, 2018 (suppl; abstr 3086).
Moreau, T., et al., (1996) "CAMPATH-IH in multiple sclerosis" Mult. Scler. 1:357-365.
Neilsen, J.Z., et al., (2013) "Anti-PD-1 Blockade and Stereotactic Radiation Produce Long-Term Survival in Mice With Intracranial Gliomas" Int. J. Radiat. Oncol. Biol. Phys. 86(2): 343-349.

(56) References Cited

OTHER PUBLICATIONS

Nielsen, C., et al., (2004) "A putative regulatory polymorphism in PD-1 is associated with nephropathy in a population-based cohort of systemic lupus erythematosus patients" Lupus 13(7):510-6.
Ngiow, S.F., (2011) "Anti-TIM3 Antibody Promotes T Cell Ifn-y-Mediated Antitumor Immunity and Suppresses Established Tumors" Cancer Research 71(10) 3540:51.
Nimmerjahn, F., et al., (2007) "Fc-receptors as regulators of immunity" Adv. Immunol. 96:179-204.
Nishimura et al., (2001) "Autoimmune dilated cardiomyopathy in PD-1 receptor-deficient mice" Science 291:319-22.
Nishimura H, et al., (1996) "Developmentally regulated expression of the PD-1 protein on the surface of double-negative (CD4−CD8−) thymocytes" Int. Immunol. 8(5):773-80.
Nishimura H, et al., (2001) "PD-1: an inhibitory immunoreceptor involved in peripheral tolerance" Trends Immunol. 22(5):265-8.
Nishimura, H., et al., (1999) "Development of lupus-like autoimmune diseases by disruption of the PD-1 gene encoding an ITIM motif-carrying immunoreceptor" Immunity 11:141-51.
Norde, W.J., (2011) "PD-1/PD-L1 Interactions Contribute to Functional T-Cell Impairment in Patients Who Relapse with Cancer After Allogeneic Stem Cell Transplantation" Cancer Res. 71(15):5111-22.
Oddone, N. et al., (2009) "Metastatic cutaneous squamous cell carcinoma of the head and neck: the Immunosuppression, Treatment, Extranodal spread, and Margin status (ITEM) prognostic score to predict outcome and the need to improve survival" Cancer 115(9):1883-1891.
Odorizzi, et al., (2015) "Genetic absence of PD-1 promotes accumulation of terminally differentiated exhausted CD8+ T cells" J. Exp. Med. 212:1125-1137.
Oestreich, K.J., et al., (2008) "NFATc1 regulates PD-1 expression upon T cell activation" J. Immunol. 181:4832-4839.
Ohaegbulam, K.C., et al., (2015) "Human cancer immunotherapy with antibodies to the PD-1 and PD-L1 pathway" Trends in Molecular Medicine 21(1):24-33.
Okazaki, T., et al., (2001) "PD-1 immunoreceptor inhibits B cell receptor-mediated signaling by recruiting src homology 2-domain-containing tyrosine phosphatase 2 to phosphotyrosine" Proc. Nat'l. Acad. Sci. USA 98(24):13866-71.
Okazaki, T., et al., (2002) "New regulatory co-receptors: inducible co-stimulator and PD-1" Curr. Opin. Immunol. 14:391779-82.
Okazaki, T., et al., (2007) "PD-1 and PD-1 ligands: from discovery to clinical application" Int. Immunol. 19:813-824.
Oken, M.M. et al., (1982) "Toxicity and response criteria of the Eastern Cooperative Oncology Group" American Journal of Clinical Oncology 5(6):649-655.
Ott, P.A., et al., (2013) "CTLA-4 and PD-1/PD-L1 Blockade: New Immunotherapeutic Modalities with Durable Clinical Benefit in Melanoma Patients" Clin. Cancer Res. 19(19):5300-9.
Palacios, R. (1982) "Concanavalin A triggers T lymphocytes by directly interacting with their receptors for activation" J. Immunol. 128:337-342.
Pan, Z.K., et al., (2015) "Clinicopathological and prognostic significance of programmed cell death ligand1 (PD-L1) expression in patients with non-small cell lung cancer: a meta-analysis" J. Thorac. Dis. 7:462-470.
Pardoll D., et al., (2012) "Immunotherapy earns its spot in the ranks of cancer therapy" J. Exp. Med. 209(2):201-9.
Pardoll DM, (2012) "The blockade of immune checkpoints in cancer immunotherapy" Nat. Rev. Cancer 12(4):252-264.
Parish, C.R., et al., (2009) "Use of the intracellular fluorescent dye CFSE to monitor lymphocyte migration and proliferation" Curr. Protoc. Immunol. Chapter 4, Unit4 9.
Parola, et al. (Jan. 2018) "Integrating High-Throughput Screening and Sequencing for Monoclonal Antibody Discovery and Engineering", Immunology, vol. 153, No. 1, pp. 31-41.
Parry, R.et al., (2005) "CTLA-4 and PD-1 receptors inhibit T-cell activation by distinct mechanisms" Mol. Cell Biol. 25:9543-9553.

Parsa, A.T., et al., (2007) "Loss of tumor suppressor PTEN function increases B7-H1 expression and immunoresistance in glioma" Nat. Med. 13:84-88.
Parse, A.T., et al., (2006) Loss of tumor suppressor PTEN function increases B7-H1 expression and immmunoresistance in glioma. Nature Medicine 13(1):88-84.
Pascolutti, R., et al., (2016) "Structure and Dynamics of PD-L1 and an Ultra-High-Affinity PD-1 Receptor Mutant" Structure 24:1719-1728.
Patsoukis, N. et al., (2015) "PD-1 alters T-cell metabolic reprogramming by inhibiting glycolysis and promoting lipolysis and fatty acid oxidation" Nat. Commun. 6:6692.
Patsoukis, N., et al., (2012) "Selective effects of PD-1 on Akt and Ras pathways regulate molecular components of the cell cycle and inhibit T cell proliferation" Sci. Signal 5:ra46.
Patsoukis, N., et al., (2013) "PD-1 increases PTEN Phosphatase activity while decreasing PTEN protein stability by inhibiting casein kinase 2" Mol. Cell Biol. 33:3091-3098.
Pauken, K.E. et al., (2014) "TIGIT and CD226: Tipping the Balance between Costimulatory and Coinhibitory Molecules to Augment the Cancer Immunotherapy Toolkit" Cancer Cell 26:785-787.
Pauken, K.E., et al., (2015) "Overcoming T cell exhaustion in infection and cancer" Trends Immunol. 36:265-276.
Peng, W., et al., (2013) "Blockade of the PD-1 pathway enhances the efficacy of adoptive cell therapy against cancer" OncoImmunology 2(2):e22691.
Pentcheba-Hoang, T., et al., (2007) "Programmed death-1 concentration at the immunological synapse is determined by ligand affinity and availability" Proc. Natl. Acad. Sci. USA 104(45):17765-70.
Petersson, K., et al., (2002) "Crystal structure of a SEA variant in complex with MHC class II reveals the ability of SEA to crosslink MHC molecules" Structure 10:1619-1626.
Phan, et al., (2003) "Cancer regression and autoimmunity induced by cytotoxic T lymphocyte-associated antigen 4 blockade in patients with metastatic melanoma" Proc. Nat'l. Acad. Sci. USA 100(14):8372-77.
"Phase 1/2 Clinical Trial of Agenus' anti-PD-1 Antibody Begins" Apr. 20, 2017 /PRNewswire/.
Philips, G.K., et al., (2014) "Therapeutic uses of anti-PD-1 and anti-PD-L1 antibodies" International Immunology 27(1):39-46.
Pickering, C.R. et al., (2014) "Mutational landscape of aggressive cutaneous squamous cell carcinoma" Clinical Cancer Research 20(24):6582-6592.
Pilon-Thomas, S., et al., (2010) "Blockade of Programmed Death Ligand 1 Enhances the Therapeutic Efficacy of Combination Immunotherapy against Melanoma" The Journal of Immunology 184:3442-3449.
Plieth, J. et al. (2001) "PD-1/PD-L1 Combination Therapies," PD-1 Report. Evaluate Corp. Boston, MA.
Ponce, R., et al., (2009) "Immunogenicity of biologically-derived therapeutics: assessment and interpretation of nonclinical safety studies" Regul. Toxicol. Pharmacol. 54:164-182.
Postow, M.A., et al., (2015) "Immune Checkpoint Blockade in Cancer Therapy" J. Clin. Oncol. 33(17):1974-82.
Postow, M.A., et al., (2015) "Nivolumab and ipilimumab versus ipilimumab in untreated melanoma" N. Engl. J. Med. 372(21):2006-17.
Prasad, D.V.R., (2003) "B7S1, a Novel B7 Family Member that Negatively Regulates T Cell Activation" Immunity 18:863-873.
Prokunina, L., et al., (2004) "Association of the PD-1.3A allele of the PDCD1 gene in patients with rheumatoid arthritis negative for rheumatoid factor and the shared epitope" Arthritis and Rheumatism 50(6):1770-1773.
Prokunina, L., et al., (2004) "The Genetic Basis of Systemic Lupus Erythematosus—Knowledge of Today and Thoughts for Tomorrow" Hum. Mol. Genet. 13(S1):R143-8.
Qureshi, O.S., et al., (2011) "Trans-endocytosis of CD80 and CD86: a molecular basis for the cell-extrinsic function of CTLA-4" Science 332(6029):600-603.

(56) References Cited

OTHER PUBLICATIONS

Reagan-Steiner, S., et al., (2016) "National, Regional, State, and Selected Local Area Vaccination Coverage Among Adolescents Aged 13-17 Years—United States" Morbidity and Mortality Weekly Report, 65(33):850-858.

Ribas, A., et al., (2012) "Tumor Immunotherapy Directed at PD-1" N. Engl. J. Med. 366(26):2517-9.

Ribas, A., et al., (2014) "The future of cancer therapy: Selecting patients who respond to PD-1/L1 blockade" Clin. Cancer Res. 20(19):4982-84.

Ribas, A., et al., (2016) "PD-1 Blockade Expands Intratumoral Memory T Cells" Cancer Immunol. Res. 4(3):194-203.

Riley, J.L. (2009) "PD-1 signaling in primary T cells" Immunol. Rev. 229:114-125.

Riley, J.L. et al. (2005) "The CD28 family: a T-cell rheostat for therapeutic control of T-cell activation" Blood 105:13-21.

Rizvi, N.A., et al., (2015) "Cancer immunology. Mutational landscape determines sensitivity to PD-1 blockade in non-small cell lung cancer" Science 348:124-128.

Robert, C., (2014) "Nivolumab in Previously Untreated Melanoma without BRAF Mutation" N. Engl. J. Med. 372:320-330.

Rodman & Renshaw Annual Global Investment Conference Sep. 2015.

Rojko, J.L., et al. (2014) "Formation, clearance, deposition, pathogenicity, and identification of biopharmaceutical-related immune complexes: review and case studies" Toxicol. Pathol. 42:725-764.

Romano, E., et al., (2015) "Ipilimumab-dependent cell-mediated cytotoxicity of regulatory T cells ex vivo by nonclassical monocytes in melanoma patients" Proc. Nat'l. Acad. Sci. USA 112(19):6140-6145.

Rosenblatt, J., et al., (2011) "PD-1 blockade by CT-011, anti PD-1 antibody, enhances ex-vivo T cell responses to autologous dendritic/myeloma fusion vaccine" J. Immunother. 34(5):409-418.

Rozali, E.N. et al., (2012) "Programmed death ligand 2 in cancer-induced immune suppression" Clin. Dev. Immunol. 2012:656340.

Sabatier, R., et al., (2015) "Prognostic and predictive value of PDL1 expression in breast cancer" Oncotarget 6:5449-5464.

Sakuishi, K., et al., (2010) "Targeting TIM-3 and PD-1 pathways to reverse T cell exhaustion and restore anti-tumor immunity" J. Exp. Med. 207(10):2187-2194.

Salama, A.D., et al., (2003) "Critical role of the programmed death-1 (PD-1) pathway in regulation of experimental autoimmune encephalomyelitis" J. Exp. Med. 198(1):71-78.

Savitsky, D., et al., "INCAGN02385 Is an Antagonist Antibody Targeting the Co-inhibitory Receptor LAG-3 for the Treatment of Human Malignancies" 3819 Presented at the American Association for Cancer Research 109th Annual Meeting Chicago, IL, USA, Apr. 14-18, 2018.

Scharping, N.E., et al., (2016) "Efficacy of PD-1 Blockade Is Potentiated by Metformin-Induced Reduction of Tumor Hypoxia" Cancer Immunol Res; 5(1):9-16.

Schmidt, L.H., et al., (2015) "PD-1 and PD-L1 Expression in NSCLC Indicate a Favorable Prognosis in Defined Subgroups" PLOS ONE 10(8):e0136023.

Schumacher, T.N., et al., (2015) "Neoantigens in cancer immunotherapy" Science 348(6230):69-74.

Selby, M.J., et al., (2013) "Anti-CTLA-4 antibodies of IgG2a isotype enhance antitumor activity through reduction of intratumoral regulatory T cells" Cancer Immunology Research, 1(1):32-42.

Seung, E., et al., (2013) "PD-1 Blockade in Chronically HIV-1-Infected Humanized Mice Suppresses Viral Loads" PLoS ONE 8(1):e77780.

Sharma, P., et al. (2015) "Immune checkpoint targeting in cancer therapy: toward combination strategies with curative potential" Cell 161:205-214.

Sharma, P., et al. (2015) "The future of immune checkpoint therapy" Science 348(6230):56-61.

Sharma, P., et al., (2016) "Nivolumab monotherapy in recurrent metastatic urothelial carcinoma (CheckMate 032): a multicentre, open-label, two-stage, multi-arm, phase 1/2 trial" The Lancet Oncology 17(11), pp. 1590-1598.

Sharpe, A.H. et al., (2002) "The B7-CD28 superfamily" Nature Reviews. Immunology 2(2):116-126.

Sheehan, J., et al. (2015) "Phage and Yeast Display" Microbiology Spectrum, vol. 3, No. 1, 17 Pages.

Sheppard, K.A. et al., (2004), "PD-1 inhibits T-cell receptor induced phosphorylation of the ZAP70/CD3zeta signalosome and downstream signaling to PKCθ" FEBS Lett. 574:37-41.

Shih et al. (2014) "Clinical Impact of Checkpoint Inhibitors as Novel Cancer Therapies," Drugs. 74(17):1993-2013.

Sica, G.L., et al., (2003) "B7-H4, a Molecule of the B7 Family, Negatively Regulates T Cell Immunity" Immunity, 18:849-861.

Simon, S., et al., (2016) "PD-1 expression conditions T cell avidity within an antigen-specific repertoire" Oncoimmunology 5(1):e1104448.

Simpson, T.R. et al., (2013) "Fc-dependent depletion of tumor-infiltrating regulatory T cells co-defines the efficacy of anti-CTLA-4 therapy against melanoma" The Journal of Experimental Medicine 210(9):1695-1710.

Simpson-Abelson, M.R., et al., (2013) "Human ovarian tumor ascites fluids rapidly and reversibly inhibit T cell receptor induced NF-κB and NFAT signaling in tumor-associated T cells" Cancer Immun.13:14-24.

Slater, N.A. et al., (2016) "PD-L1 expression in cutaneous squamous cell carcinoma correlates with risk of metastasis" Journal of Cutaneous Pathology 43(8):663-670.

Soares, K.C., et al., (2015) "PD-1/PD-L1 blockade together with vaccine therapy facilitates effector T cell infiltration into pancreatic tumors" J. Immunother. 38(1): 1-11.

Stebbings, R., et al., (2007) "Cytokine storm in the phase I trial of monoclonal antibody TGN1412: better understanding the causes to improve preclinical testing of immunotherapeutics" J. Immunol. 179:3325-3331.

Stein, R. "Agonist Checkpoint Modulators: Challenges and Opportunities" PEGS Boston May 8, 2015.

Stein, R. "Immuno-Oncology" RBS Immunotherapy Conference Mar. 27, 2014.

Stein, R., "Next generation immunomodulatory antibodies: optimizing therapeutic impact" Blair Maidstone I-O Conference 2017.

Strome, S.E., et al., (2003) "B7-H1 blockade augments adoptive T-cell immunotherapy for squamous cell carcinoma" Cancer Res. 63:6501-6505.

Sun, Z., et al., (2015) "IL10 and PD-1 Cooperate to Limit the Activity of Tumor-Specific CD8+ T Cells" Cancer Res. 75(8):1635-44.

Sznol et al., (2013) "Antagonist antibodies to PD-1 and B7-H1 (PD-L1) in the treatment of advanced human cancer-response" Clinical Cancer Research 19(19):5542.

Sznol, M., et al., (2013) "Antagonist antibodies to PD-1 and B7-H1 (PD-L1) in the treatment of advanced human cancer" Clin. Cancer Res. 19:1021-1034.

Takeda, K., et al., (2010) "Combination therapy of established tumors by antibodies targeting immune activating and suppressing molecules" J. Immunol. 184:5493-5501.

Tan, S., et al., (2016) "An unexpected N-terminal loop in PD-1 dominates binding by nivolumab" Nature Communications 8:14369.

Tang, X., et al., (2015) "The advantages of PD1 activating chimeric receptor (PD1-ACR) engineered lymphocytes for PDL1+ cancer therapy" Am. J. Transl. Res. 7(3):460-473.

Taube, J.M., et al., (2014) "Association of PD-1, PD-1 Ligands, and Other Features of the Tumor Immune Microenvironment with Response to Anti-PD-1 Therapy" Clin Cancer Res; 20(19):5064-74.

Taylor, A., et al., (2016) "Glycogen Synthase Kinase 3 Inactivation Drives T-bet-Mediated Downregulation of Co-receptor PD-1 to Enhance CD8+ Cytolytic T Cell Responses" Immunity 44:274-286.

Tewari, K.S., et al., (2014) "Improved survival with bevacizumab in advanced cervical cancer" N. Engl. J. Med. 370(8):734-743.

Thomas, M. L., (1995) "Of ITAMs and ITIMs: turning on and off the B cell antigen receptor." J. Exp. Med. 181:1953-6.

(56) References Cited

OTHER PUBLICATIONS

Thompson, R.H., et al., (2007) "PD-1 is expressed by tumor-infiltrating immune cells and is associated with poor outcome for patients with renal cell carcinoma" Clin. Cancer Res. 13:1757-1761.
Three Agenus Abstracts Accepted for Presentation at the American Association for Cancer Research (AACR) 2018 Annual Meeting Apr. 11, 2018 /PRNewswire/.
Topalian, S.L., et al., (2012) "Safety, activity, and immune correlates of anti-PD-1 antibody in cancer" N. Engl. J. Med. 366:2443-2454.
Topalian, S.L., et al., (2012) "Targeting the PD-1/B7-H1(PD-L1) pathway to activate anti-tumor immunity." Curr. Opin. Immunol. 24(2):207-12.
Topalian, S.L., et al., (2015) "Immune Checkpoint Blockade: A Common Denominator Approach to Cancer Therapy" Cancer Cell 27:450-61.
Torre, L.A., et al., (2015) "Global cancer statistics, 2012" CA: A Cancer Journal for Clinicians 65(2):87-108.
Tseng, S.Y., et al., (2001) "B7-DC, a new dendritic cell molecule with potent costimulatory properties for T cells" J. Exp. Med. 193:839-846.
Turnis, M.E., et al., (2012) "Combinatorial immunotherapy PD-1 may not be LAG-ing behind any more" OncoImmunology 1(7):1172-1174.
Tykodi, S.S., (2014) "PD-1 as an emerging therapeutic target in renal cell carcinoma: current evidence" OncoTargets and Therapy 7:1349-1359.
U.S. Food and Drug Administration (2016). FDA approves new, targeted treatment for bladder cancer.
U.S. Food and Drug Administration (2016). pembrolizumab (KEYTRUDA).
Van Regenmortel, M.H.V., (2018) "Development of a Preventive HIV Vaccine Requires Solving Inverse Problems Which Is Unattainable by Rational Vaccine Design" Frontiers in Immunology, vol. 8, Article 2009, 11 Pages.
Vessillier, S., et al., (2015) "Cytokine release assays for the prediction of therapeutic mAb safety in first-in man trials—Whole blood cytokine release assays are poorly predictive for TGN1412 cytokine storm" J. Immunol. Methods 424:43-52.
Victor, C.T., et al., (2015) "Radiation and dual checkpoint blockade activate non-redundant immune mechanisms in cancer" Nature 520(7547):373-7.
Vidal, J.M., et al., (2010) "In vitro cytokine release assays for predicting cytokine release syndrome: the current state-of-the-science. Report of a European Medicines Agency Workshop" Cytokine 51:213-215.
Vigdorovich, V. et al., (2013) "Structure and T cell inhibition properties of B7 family member, B7-H3" Structure 21(5):707-17.
Villasboas, J.C., et al., (2016) "Targeting the PD-1 pathway in patients with relapsed classic Hodgkin lymphoma following allogeneic stem cell transplant is safe and effective" Oncotarget 7(11):13260-4.
Vivier, E., et al., (1997) "Immunoreceptor tyrosine-based inhibition motifs." Immunol. Today 18:286-91.
Waight, J., et al., "INCAGN02390, a Novel Antagonist Antibody That Targets the Co-Inhibitory Receptor TIM-3" 3825 Presented at the American Association for Cancer Research 109th Annual Meeting Chicago, IL, USA, Apr. 14-18, 2018.
Walker, L.S.K., et al., (2015) "Confusing signals: recent progress in CTLA-4 biology" Trends in immunology 36(2):63-70.
Wang et al., (2014) "In vitro characterization of the anti-PD-1 antibody nivolumab, BMS-936558, and in vivo toxicology in non-human primates." Cancer Immunol. Res. 2(9):846-56.
Wang, Li, et al., (2008) "Programmed death 1 ligand signaling regulates the generation of adaptive Foxp3 CD4 regulatory T cells" PNAS 105(27):9331-9336.
Weber, J.S., et al., (2012) "Management of immune-related adverse events and kinetics of response with ipilimumab" Journal of Clinical Oncology 30(21):2691-2697.
Westin, J.R., et al., (2014) "Safety and activity of PD1 blockade by pidilizumab in combination with rituximab in patients with relapsed follicular lymphoma: a single group, open-label, phase 2 trial" Lancet 15:69-77.
Wherry, E.J., et al., (2007) "Molecular signature of CD8+ T cell exhaustion during chronic viral infection" Immunity 27:670-684.
Wherry, E.J., et al., (2015) "Molecular and cellular insights into T cell exhaustion" Nat. Rev. Immunol. 15:486-499.
Wilky, B.A., et al., "Phase 1 Open-Label, Ascending Dose Trial of AGEN1884, an anti-CTLA-4 Monoclonal Antibody, in Advanced Solid Malignancies: Dose Selection for Combination With PD-1 Blockade" 18/1200-A ASCO C-500-01, 225917 (2018).
Wilson, N. "Targeting TNFR Family Members: Therapeutic opportunities in immuno-oncology and immuno-inflammation" PEGS Boston 2016.
Wing, K. et al., (2008) "CTLA-4 control over Foxp3+ regulatory T cell function" Science 322(5899):271-275.
Wolchok, J.D. et al., (2016) "Updated results from a phase III trial of nivolumab (NIVO) combined with ipilimumab (IPI) in treatment-naive patients (pts) with advanced melanoma (MEL) (CheckMate 067)" Journal of Clinical Oncology 34(15 suppl.):9505-9505.
Wolchok, J.D., et al., (2009) "Guidelines for the Evaluation of Immune Therapy Activity in Solid Tumors: Immune-Related Response Criteria" Clin. Cancer Res. 15(23):7412-20.
Wolchok, J.D., et al., (2013) "Nivolumab plus ipilimumab in advanced melanoma" N. Engl. J. Med. 369:122-133.
Wolf, B., et al., (2012) "A whole blood in vitro cytokine release assay with aqueous monoclonal antibody presentation for the prediction of therapeutic protein induced cytokine release syndrome in humans" Cytokine 60:828-837.
Wong, R.M., et al., (2007) "Programmed death-1 blockade enhances expansion and functional capacity of human melanoma antigen-specific CTLs" International Immunology, 19(10):1223-1234.
Woo, S., et al., (2012) "Immune Inhibitory Molecules LAG-3 and PD-1 Synergistically Regulate T-cell Function to Promote Tumoral Immune Escape" Cancer Res. 72:917-927.
Xing, K., et al., (2015) "Dexamethasone enhances programmed cell death 1 (PD-1) expression during T cell activation: an insight into the optimum application of glucocorticoids in anti-cancer therapy" BMC Immunol. 16, 39.
Yang, W., et al., (2013) "Increased expression of programmed death (PD)-1 and its ligand PD-L1 correlates with impaired cell-mediated immunity in high-risk human papillomavirus-related cervical intraepithelial neoplasia" Immunology 139(4):513-522.
Yokosuka, T., et al., (2012) "Programmed cell death 1 forms negative costimulatory microclusters that directly inhibit T cell receptor signaling by recruiting phosphatase SHP2" J. Exp. Med. 209:1201-1217.
Young, A., et al., (2014) "Targeting Cancer-Derived Adenosine New Therapeutics Approaches" Cancer Discovery 4:879-888.
Yu, G., et al., (2015) "PD-1 blockade attenuates immunosuppressive myeloid cells due to inhibition of CD47/SIRPa axis in HPV negative head and neck squamous cell carcinoma" Oncotarget 6(39):42067-80.
Yu, S., et al., (2015) "Advancements in Recurrent and Metastatic Cervical Cancer" Am. J. Hematol. Oncol. 11:26-31.
Zaretsky, J.M., et al., (2016) "Mutations Associated with Acquired Resistance to PD-1 Blockade in Melanoma" N. Engl. J. Med. 375(9):819-829.
Zeng J., et al., (2013) "Anti-PD-1 Blockade and Stereotactic Radiation Produce Long-Term Survival in Mice with Intracranial Gliomas" Radiation Oncology Biology 86(2):343-349.
Zha, Y., et al., (2004) "Negative regulation of T-cell function by PD-1" Crit. Rev. Immunol. 24:229-237.
Zhao, R., et al., (2013) "HHLA2 is a member of the B7 family and inhibits human CD4 and CD8 T-cell function" Proc. Natl. Acad. Sci USA 110:9879-9884.
Zheng, P., et al., (2015) "Human Cancer Immunotherapy with PD-1/PD-L1 Blockade" Biomarkers in Cancer 7(s2):15-18.
Zhou, Q., et al., (2010) "Blockade of programmed death-1 pathway rescues the effector function of tumor-infiltrating T cells and enhances the antitumor efficacy of lentivector immunization" J. Immunol. 185:5082-5092.

(56) References Cited

OTHER PUBLICATIONS

Zhou, Q., et al. (2015) "Structural Repertoire of HIV-1-Neutralizing Antibodies Targeting the CD4 Supersite in 14 Donors" Cell, vol. 161, No. 6, pp. 1280-1292.

Zippelius, A., et al., (2015) "Induced PD-L1 expression mediates acquired resistance to agonistic anti-CD40 treatment" Cancer Immunol. Res. 3:236-244.

Zitvogel, L., et al., (2012) "Targeting PD-1/PD-L1 interactions for cancer immunotherapy" OncoImmunology 1(8):1223-1225.

Zou, W., et al., (2008) "Inhibitory B7-family molecules in the tumour microenvironment" Nat. Rev. Immunol. 8:467-477.

Zou, W., et al., (2016) "PD-L1 (B7-H1) and PD-1 pathway blockade for cancer therapy: Mechanisms, response biomarkers, and combinations" Science 8(328):328rv4.

Zwald, F.O., et al., (2011) "Skin cancer in solid organ transplant recipients: advances in therapy and management: part I. Epidemiology of skin cancer in solid organ transplant recipients" Journal of the American Academy of Dermatology 65(2):253-261.

U.S. Appl. No. 15/254,315, filed Sep. 1, 2016, 2017/0081409, Mar. 23, 2017, Marc Van Dijk, U.S. Pat. No. 10,323,091, Jun. 18, 2019.

U.S. Appl. No. 16/435,175, filed Jun. 7, 2019, Marc Van Dijk.

\* cited by examiner

SEQUENCE LISTING

```
<160> NUMBER OF SEQ ID NOS: 79

<210> SEQ ID NO 1
<211> LENGTH: 5
<212> TYPE: PRT
<213> ORGANISM: Artificial Sequence
<220> FEATURE:
<223> OTHER INFORMATION: AGEN2033w Kabat CDRH1

<400> SEQUENCE: 1

Ser Tyr Gly Met His
1               5
```

<210> SEQ ID NO 2
<211> LENGTH: 17
<212> TYPE: PRT
<213> ORGANISM: Artificial Sequence
<220> FEATURE:
<223> OTHER INFORMATION: AGEN2033w Kabat CDRH2

<400> SEQUENCE: 2

Val Ile Trp Tyr Asp Gly Ser Asn Lys Tyr Tyr Ala Asp Ser Val Lys
1               5                   10                  15

Gly

<210> SEQ ID NO 3
<211> LENGTH: 4
<212> TYPE: PRT
<213> ORGANISM: Artificial Sequence
<220> FEATURE:
<223> OTHER INFORMATION: AGEN2033w Kabat CDRH3

<400> SEQUENCE: 3

Asn Val Asp Tyr
1

<210> SEQ ID NO 4
<211> LENGTH: 11
<212> TYPE: PRT
<213> ORGANISM: Artificial Sequence
<220> FEATURE:
<223> OTHER INFORMATION: AGEN2033w Kabat CDRL1

<400> SEQUENCE: 4

Arg Ala Ser Gln Ser Val Ser Ser Asn Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: AGEN2033w Kabat CDRL2

<400> SEQUENCE: 5

Gly Ala Ser Thr Arg Ala Thr
1               5

<210> SEQ ID NO 6
<211> LENGTH: 9
<212> TYPE: PRT
<213> ORGANISM: Artificial Sequence
<220> FEATURE:
<223> OTHER INFORMATION: AGEN2033w Kabat CDRL3

<400> SEQUENCE: 6

Gln Gln Tyr Asn Asn Trp Pro Arg Thr
1               5

<210> SEQ ID NO 7
<211> LENGTH: 4
<212> TYPE: PRT
<213> ORGANISM: Artificial Sequence
<220> FEATURE:
<223> OTHER INFORMATION: AGEN2034w Kabat CDRH3

<400> SEQUENCE: 7

Asn Gly Asp His
1

<210> SEQ ID NO 8
<211> LENGTH: 8
<212> TYPE: PRT
<213> ORGANISM: Artificial Sequence
<220> FEATURE:
<223> OTHER INFORMATION: AGEN2033w IMGT CDRH1

<400> SEQUENCE: 8

Gly Phe Thr Phe Ser Ser Tyr Gly
1               5

<210> SEQ ID NO 9
<211> LENGTH: 8
<212> TYPE: PRT
<213> ORGANISM: Artificial Sequence
<220> FEATURE:
<223> OTHER INFORMATION: AGEN2033w IMGT CDRH2

<400> SEQUENCE: 9

Ile Trp Tyr Asp Gly Ser Asn Lys
1               5

<210> SEQ ID NO 10
<211> LENGTH: 6
<212> TYPE: PRT
<213> ORGANISM: Artificial Sequence
<220> FEATURE:
<223> OTHER INFORMATION: AGEN2033w IMGT CDRH3

<400> SEQUENCE: 10

Ala Ser Asn Val Asp Tyr
1               5

<210> SEQ ID NO 11
<211> LENGTH: 6
<212> TYPE: PRT
<213> ORGANISM: Artificial Sequence
<220> FEATURE:
<223> OTHER INFORMATION: AGEN2033w IMGT CDRL1

<400> SEQUENCE: 11

Gln Ser Val Ser Ser Asn
1               5

<210> SEQ ID NO 12
<211> LENGTH: 3
<212> TYPE: PRT
<213> ORGANISM: Artificial Sequence
<220> FEATURE:
<223> OTHER INFORMATION: AGEN2033w IMGT CDRL2

<400> SEQUENCE: 12

Gly Ala Ser
1

<210> SEQ ID NO 13
<211> LENGTH: 9
<212> TYPE: PRT
<213> ORGANISM: Artificial Sequence
<220> FEATURE:
<223> OTHER INFORMATION: AGEN2033w IMGT CDRL3

<400> SEQUENCE: 13

Gln Gln Tyr Asn Asn Trp Pro Arg Thr
1               5

-continued

<210> SEQ ID NO 14
<211> LENGTH: 6
<212> TYPE: PRT
<213> ORGANISM: Artificial Sequence
<220> FEATURE:
<223> OTHER INFORMATION: AGEN2034w IMGT CDRH3

<400> SEQUENCE: 14

Ala Ser Asn Gly Asp His
1               5

<210> SEQ ID NO 15
<211> LENGTH: 113
<212> TYPE: PRT
<213> ORGANISM: Artificial Sequence
<220> FEATURE:
<223> OTHER INFORMATION: AGEN2033w, AGEN2046w VH

<400> SEQUENCE: 15

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Val Asp Tyr Trp Gly Gln Gly Thr Leu Val Thr Val Ser
            100                 105                 110

Ser

<210> SEQ ID NO 16
<211> LENGTH: 107
<212> TYPE: PRT
<213> ORGANISM: Artificial Sequence
<220> FEATURE:
<223> OTHER INFORMATION: AGEN2033w, AGEN2034w, AGEN2046w, AGEN2047w VL

<400> SEQUENCE: 16

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Arg
                85                  90                  95

Thr Phe Gly Gln Gly Thr Lys Val Glu Ile Lys
            100                 105

<210> SEQ ID NO 17

<211> LENGTH: 113
<212> TYPE: PRT
<213> ORGANISM: Artificial Sequence
<220> FEATURE:
<223> OTHER INFORMATION: AGEN2034w, AGEN2047w VH

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Gly Asp His Trp Gly Gln Gly Thr Leu Val Thr Val Ser
            100                 105                 110

Ser

<210> SEQ ID NO 18
<211> LENGTH: 440
<212> TYPE: PRT
<213> ORGANISM: Artificial Sequence
<220> FEATURE:
<223> OTHER INFORMATION: AGEN2033w heavy chain IgG4 S228P

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Val Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
            210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
            325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
            405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 19
<211> LENGTH: 214
<212> TYPE: PRT
<213> ORGANISM: Artificial Sequence
<220> FEATURE:
<223> OTHER INFORMATION: AGEN2033w, AGEN2034w, AGEN2046w, AGEN2047w
    light chain

<400> SEQUENCE: 19

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Arg
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly

```
            115                 120                 125
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 440
<212> TYPE: PRT
<213> ORGANISM: Artificial Sequence
<220> FEATURE:
<223> OTHER INFORMATION: AGEN2034w heavy chain IgG4 S228P

<400> SEQUENCE: 20

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Gly Asp His Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
```

```
                260                 265                 270
Asp Gly Val Glu Val His Asn Ala Lys Thr Lys Pro Arg Glu Glu Gln
            275                 280                 285

Phe Asn Ser Thr Tyr Arg Val Ser Val Leu Thr Val Leu His Gln
            290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
            325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
            370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
            405                 410                 415

Ser Cys Ser Val Met His Glu Ala Leu His Asn His Tyr Thr Gln Lys
            420                 425                 430

Ser Leu Ser Leu Ser Leu Gly Lys
            435                 440

<210> SEQ ID NO 21
<211> LENGTH: 443
<212> TYPE: PRT
<213> ORGANISM: Artificial Sequence
<220> FEATURE:
<223> OTHER INFORMATION: AGEN2046w heavy chain IgG1

<400> SEQUENCE: 21

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Ser Asn Val Asp Tyr Trp Gly Gln Gly Thr Leu Val Thr Val Ser
            100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
            130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Gln
```

```
                180                 185                 190
Thr Tyr Ile Cys Asn Val Asn His Lys Pro Ser Asn Thr Lys Val Asp
            195                 200                 205
Lys Arg Val Glu Pro Lys Ser Cys Asp Lys Thr His Thr Cys Pro Pro
        210                 215                 220
Cys Pro Ala Pro Glu Leu Leu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Lys Phe Asn
            260                 265                 270
Trp Tyr Val Asp Gly Val Glu Val His Asn Ala Lys Thr Lys Pro Arg
        275                 280                 285
Glu Glu Gln Tyr Asn Ser Thr Tyr Arg Val Val Ser Val Leu Thr Val
                290                 295                 300
Leu His Gln Asp Trp Leu Asn Gly Lys Glu Tyr Lys Cys Lys Val Ser
305                 310                 315                 320
Asn Lys Ala Leu Pro Ala Pro Ile Glu Lys Thr Ile Ser Lys Ala Lys
                325                 330                 335
Gly Gln Pro Arg Glu Pro Gln Val Tyr Thr Leu Pro Pro Ser Arg Glu
            340                 345                 350
Glu Met Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
    370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys
        435                 440

<210> SEQ ID NO 22
<211> LENGTH: 443
<212> TYPE: PRT
<213> ORGANISM: Artificial Sequence
<220> FEATURE:
<223> OTHER INFORMATION: AGEN2047w heavy chain IgG1

<400> SEQUENCE: 22

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Trp Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ser Asn Gly Asp His Trp Gly Gln Gly Thr Leu Val Thr Val Ser
```

```
            100                 105                 110
Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
            130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
            195                 200                 205

Lys Arg Val Glu Pro Lys Ser Cys Asp Lys Thr His Thr Cys Pro Pro
            210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
            290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
            325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 23
<211> LENGTH: 443
<212> TYPE: PRT
<213> ORGANISM: Artificial Sequence
<220> FEATURE:
<223> OTHER INFORMATION: AGEN2047w heavy chain IgG1 N297A

<400> SEQUENCE: 23

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
```

```
                    20                  25                  30
Gly Met His Trp Val Arg Gln Ala Pro Gly Lys Gly Leu Glu Trp Val
                35                  40                  45
Ala Val Ile Trp Tyr Asp Gly Ser Asn Lys Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ser Asn Gly Asp His Trp Gly Gln Gly Thr Leu Val Thr Val Ser
                100                 105                 110
Ser Ala Ser Thr Lys Gly Pro Ser Val Phe Pro Leu Ala Pro Ser Ser
            115                 120                 125
Lys Ser Thr Ser Gly Gly Thr Ala Ala Leu Gly Cys Leu Val Lys Asp
        130                 135                 140
Tyr Phe Pro Glu Pro Val Thr Val Ser Trp Asn Ser Gly Ala Leu Thr
145                 150                 155                 160
Ser Gly Val His Thr Phe Pro Ala Val Leu Gln Ser Ser Gly Leu Tyr
                165                 170                 175
Ser Leu Ser Ser Val Val Thr Val Pro Ser Ser Ser Leu Gly Thr Gln
            180                 185                 190
Thr Tyr Ile Cys Asn Val Asn His Lys Pro Ser Asn Thr Lys Val Asp
        195                 200                 205
Lys Arg Val Glu Pro Lys Ser Cys Asp Lys Thr His Thr Cys Pro Pro
    210                 215                 220
Cys Pro Ala Pro Glu Leu Leu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Lys Phe Asn
            260                 265                 270
Trp Tyr Val Asp Gly Val Glu Val His Asn Ala Lys Thr Lys Pro Arg
        275                 280                 285
Glu Glu Gln Tyr Ala Ser Thr Tyr Arg Val Val Ser Val Leu Thr Val
    290                 295                 300
Leu His Gln Asp Trp Leu Asn Gly Lys Glu Tyr Lys Cys Lys Val Ser
305                 310                 315                 320
Asn Lys Ala Leu Pro Ala Pro Ile Glu Lys Thr Ile Ser Lys Ala Lys
                325                 330                 335
Gly Gln Pro Arg Glu Pro Gln Val Tyr Thr Leu Pro Pro Ser Arg Glu
            340                 345                 350
Glu Met Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
    370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys
        435                 440
```

<210> SEQ ID NO 24
<211> LENGTH: 443
<212> TYPE: PRT
<213> ORGANISM: Artificial Sequence
<220> FEATURE:
<223> OTHER INFORMATION: AGEN2047w heavy chain IgG1 S267E/L328F

<400> SEQUENCE: 24

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Gly Asp His Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Glu His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Phe Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365
```

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 25
<211> LENGTH: 443
<212> TYPE: PRT
<213> ORGANISM: Artificial Sequence
<220> FEATURE:
<223> OTHER INFORMATION: AGEN2047w heavy chain IgG1 S239D/A330L/I332E

<400> SEQUENCE: 25

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Gly Asp His Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
    210                 215                 220

Cys Pro Ala Pro Glu Leu Leu Gly Gly Pro Asp Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
      290                 295                 300

Leu His Gln Asp Trp Leu Asn Gly Lys Glu Tyr Lys Cys Lys Val Ser
305                 310                 315                 320

Asn Lys Ala Leu Pro Leu Pro Glu Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 26
<211> LENGTH: 113
<212> TYPE: PRT
<213> ORGANISM: Artificial Sequence
<220> FEATURE:
<223> OTHER INFORMATION: AGEN2001w VH (BADD426-2614)

<400> SEQUENCE: 26

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Asn Gly Asp Tyr Trp Gly Gln Gly Thr Leu Val Thr Val Ser
            100                 105                 110

Ser

<210> SEQ ID NO 27
<211> LENGTH: 113
<212> TYPE: PRT
<213> ORGANISM: Artificial Sequence
<220> FEATURE:
<223> OTHER INFORMATION: AGEN2002w VH (BADD426-2615)

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

```
Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ser Asn Gly Asp Tyr Trp Gly Gln Gly Thr Leu Val Thr Val Ser
            100                 105                 110

Ser

<210> SEQ ID NO 28
<211> LENGTH: 113
<212> TYPE: PRT
<213> ORGANISM: Artificial Sequence
<220> FEATURE:
<223> OTHER INFORMATION: EP11_pl1_B03 (BADD438-2743)

<400> SEQUENCE: 28

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Asn Glu Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ser Asn Gly Asp His Trp Gly Gln Gly Thr Leu Val Thr Val Ser
            100                 105                 110

Ser

<210> SEQ ID NO 29
<211> LENGTH: 113
<212> TYPE: PRT
<213> ORGANISM: Artificial Sequence
<220> FEATURE:
<223> OTHER INFORMATION: EP11_pl1_B05 (BADD438-2745)

<400> SEQUENCE: 29

Gln Val Gln Leu Val Glu Ser Gly Gly Gly Met Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Phe Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

Ala Ser Asn Gly Asp His Trp Gly Gln Gly Thr Leu Val Thr Val Ser
            100                 105                 110

Ser

<210> SEQ ID NO 30
<211> LENGTH: 113
<212> TYPE: PRT
<213> ORGANISM: Artificial Sequence
<220> FEATURE:
<223> OTHER INFORMATION: EP11_p11_C02 (BADD438-2746)

<400> SEQUENCE: 30

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Gly Asp His Trp Gly His Gly Thr Leu Val Thr Val Ser
            100                 105                 110

Ser

<210> SEQ ID NO 31
<211> LENGTH: 113
<212> TYPE: PRT
<213> ORGANISM: Artificial Sequence
<220> FEATURE:
<223> OTHER INFORMATION: EP11_p11_C03 (BADD438-2747)

<400> SEQUENCE: 31

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Met Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Gly Asp His Trp Gly Gln Gly Thr Leu Val Thr Val Ser
            100                 105                 110

Ser

<210> SEQ ID NO 32
<211> LENGTH: 17
<212> TYPE: PRT
<213> ORGANISM: Artificial Sequence
<220> FEATURE:
<223> OTHER INFORMATION: CDRH2 consensus
<220> FEATURE:

```
<221> NAME/KEY: VARIANT
<222> LOCATION: (4)..(4)
<223> OTHER INFORMATION: Tyr or Phe
<220> FEATURE:
<221> NAME/KEY: VARIANT
<222> LOCATION: (9)..(9)
<223> OTHER INFORMATION: Lys or Glu
<220> FEATURE:
<221> NAME/KEY: VARIANT
<222> LOCATION: (16)..(16)
<223> OTHER INFORMATION: Lys or Met

<400> SEQUENCE: 32

Val Ile Trp Xaa Asp Gly Ser Asn Xaa Tyr Tyr Ala Asp Ser Val Xaa
1               5                   10                  15

Gly

<210> SEQ ID NO 33
<211> LENGTH: 4
<212> TYPE: PRT
<213> ORGANISM: Artificial Sequence
<220> FEATURE:
<223> OTHER INFORMATION: CDRH3 consensus
<220> FEATURE:
<221> NAME/KEY: VARIANT
<222> LOCATION: (2)..(2)
<223> OTHER INFORMATION: Gly or Val
<220> FEATURE:
<221> NAME/KEY: VARIANT
<222> LOCATION: (4)..(4)
<223> OTHER INFORMATION: His or Tyr

<400> SEQUENCE: 33

Asn Xaa Asp Xaa
1

<210> SEQ ID NO 34
<211> LENGTH: 17
<212> TYPE: PRT
<213> ORGANISM: Artificial Sequence
<220> FEATURE:
<223> OTHER INFORMATION: CDRH2

<400> SEQUENCE: 34

Val Ile Trp Tyr Asp Gly Ser Asn Glu Tyr Tyr Ala Asp Ser Val Lys
1               5                   10                  15

Gly

<210> SEQ ID NO 35
<211> LENGTH: 17
<212> TYPE: PRT
<213> ORGANISM: Artificial Sequence
<220> FEATURE:
<223> OTHER INFORMATION: CDRH2

<400> SEQUENCE: 35

Val Ile Trp Phe Asp Gly Ser Asn Lys Tyr Tyr Ala Asp Ser Val Lys
1               5                   10                  15

Gly

<210> SEQ ID NO 36
<211> LENGTH: 17
<212> TYPE: PRT
<213> ORGANISM: Artificial Sequence
<220> FEATURE:
<223> OTHER INFORMATION: CDRH2

<400> SEQUENCE: 36
```

Val Ile Trp Tyr Asp Gly Ser Asn Lys Tyr Tyr Ala Asp Ser Val Met
1               5                   10                  15

Gly

<210> SEQ ID NO 37
<211> LENGTH: 4
<212> TYPE: PRT
<213> ORGANISM: Artificial Sequence
<220> FEATURE:
<223> OTHER INFORMATION: CDRH3

<400> SEQUENCE: 37

Asn Gly Asp Tyr
1

<210> SEQ ID NO 38
<211> LENGTH: 30
<212> TYPE: PRT
<213> ORGANISM: Artificial Sequence
<220> FEATURE:
<223> OTHER INFORMATION: VH FR1

<400> SEQUENCE: 38

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: VH FR1

<400> SEQUENCE: 39

Gln Val Gln Leu Val Glu Ser Gly Gly Gly Met Val Gln Pro Gly Arg
1               5                   10                  15

Ser Leu Arg Leu Ser Cys Ala Ala Ser Gly Phe Thr Phe Ser
            20                  25                  30

<210> SEQ ID NO 40
<211> LENGTH: 14
<212> TYPE: PRT
<213> ORGANISM: Artificial Sequence
<220> FEATURE:
<223> OTHER INFORMATION: VH FR2

<400> SEQUENCE: 40

Trp Val Arg Gln Ala Pro Gly Lys Gly Leu Glu Trp Val Ala
1               5                   10

<210> SEQ ID NO 41
<211> LENGTH: 32
<212> TYPE: PRT
<213> ORGANISM: Artificial Sequence
<220> FEATURE:
<223> OTHER INFORMATION: VH FR3

<400> SEQUENCE: 41

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: VH FR3

<400> SEQUENCE: 42

Arg Phe Thr Ile Ser Arg Asp Asn Ser Lys Asn Thr Leu Tyr Leu Gln
 1               5                  10                  15

Met Asn Ser Leu Arg Ala Glu Asp Thr Ala Val Tyr Tyr Cys Ala Thr
             20                  25                  30

<210> SEQ ID NO 43
<211> LENGTH: 11
<212> TYPE: PRT
<213> ORGANISM: Artificial Sequence
<220> FEATURE:
<223> OTHER INFORMATION: VH FR4

<400> SEQUENCE: 43

Trp Gly Gln Gly Thr Leu Val Thr Val Ser Ser
 1               5                  10

<210> SEQ ID NO 44
<211> LENGTH: 11
<212> TYPE: PRT
<213> ORGANISM: Artificial Sequence
<220> FEATURE:
<223> OTHER INFORMATION: VH FR4

<400> SEQUENCE: 44

Trp Gly His Gly Thr Leu Val Thr Val Ser Ser
 1               5                  10

<210> SEQ ID NO 45
<211> LENGTH: 23
<212> TYPE: PRT
<213> ORGANISM: Artificial Sequence
<220> FEATURE:
<223> OTHER INFORMATION: VL FR1

<400> SEQUENCE: 45

Glu Ile Val Met Thr Gln Ser Pro Ala Thr Leu Ser Val Ser Pro Gly
 1               5                  10                  15

Glu Arg Ala Thr Leu Ser Cys
             20

<210> SEQ ID NO 46
<211> LENGTH: 15
<212> TYPE: PRT
<213> ORGANISM: Artificial Sequence
<220> FEATURE:
<223> OTHER INFORMATION: VL FR2

<400> SEQUENCE: 46

Trp Tyr Gln Gln Lys Pro Gly Gln Ala Pro Arg Leu Leu Ile Tyr
 1               5                  10                  15

<210> SEQ ID NO 47
<211> LENGTH: 32
<212> TYPE: PRT
<213> ORGANISM: Artificial Sequence
<220> FEATURE:
<223> OTHER INFORMATION: VL FR3

<400> SEQUENCE: 47

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 48
<211> LENGTH: 10
<212> TYPE: PRT
<213> ORGANISM: Artificial Sequence
<220> FEATURE:
<223> OTHER INFORMATION: VL FR4

<400> SEQUENCE: 48

Phe Gly Gln Gly Thr Lys Val Glu Ile Lys
1               5                   10

<210> SEQ ID NO 49
<211> LENGTH: 113
<212> TYPE: PRT
<213> ORGANISM: Artificial Sequence
<220> FEATURE:
<223> OTHER INFORMATION: VH consensus sequence
<220> FEATURE:
<221> NAME/KEY: VARIANT
<222> LOCATION: (11)..(11)
<223> OTHER INFORMATION: Val or Met
<220> FEATURE:
<221> NAME/KEY: VARIANT
<222> LOCATION: (53)..(53)
<223> OTHER INFORMATION: Tyr or Phe
<220> FEATURE:
<221> NAME/KEY: VARIANT
<222> LOCATION: (58)..(58)
<223> OTHER INFORMATION: Lys or Glu
<220> FEATURE:
<221> NAME/KEY: VARIANT
<222> LOCATION: (65)..(65)
<223> OTHER INFORMATION: Lys or Met
<220> FEATURE:
<221> NAME/KEY: VARIANT
<222> LOCATION: (98)..(98)
<223> OTHER INFORMATION: Ser or Thr
<220> FEATURE:
<221> NAME/KEY: VARIANT
<222> LOCATION: (100)..(100)
<223> OTHER INFORMATION: Gly or Val
<220> FEATURE:
<221> NAME/KEY: VARIANT
<222> LOCATION: (102)..(102)
<223> OTHER INFORMATION: His or Tyr
<220> FEATURE:
<221> NAME/KEY: VARIANT
<222> LOCATION: (105)..(105)
<223> OTHER INFORMATION: Gln or His

<400> SEQUENCE: 49

Gln Val Gln Leu Val Glu Ser Gly Gly Xaa Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Xaa Asp Gly Ser Asn Xaa Tyr Tyr Ala Asp Ser Val
    50                  55                  60

Xaa Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Xaa Asn Xaa Asp Xaa Trp Gly Xaa Gly Thr Leu Val Thr Val Ser
        100                 105                 110

Ser
```

<210> SEQ ID NO 50
<211> LENGTH: 98
<212> TYPE: PRT
<213> ORGANISM: Homo sapiens

<400> SEQUENCE: 50

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 51
<211> LENGTH: 95
<212> TYPE: PRT
<213> ORGANISM: Homo sapiens

<400> SEQUENCE: 51

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95
```

<210> SEQ ID NO 52
<211> LENGTH: 439
<212> TYPE: PRT
<213> ORGANISM: Artificial Sequence
<220> FEATURE:
<223> OTHER INFORMATION: AGEN2033w heavy chain IgG4 S228P (without C-
      terminal lysine)

<400> SEQUENCE: 52

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30
```

```
Gly Met His Trp Val Arg Gln Ala Pro Gly Lys Gly Leu Glu Trp Val
        35                  40                  45
Ala Val Ile Trp Tyr Asp Gly Ser Asn Lys Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Ser Asn Val Asp Tyr Trp Gly Gln Gly Thr Leu Val Thr Val Ser
                100                 105                 110
Ser Ala Ser Thr Lys Gly Pro Ser Val Phe Pro Leu Ala Pro Cys Ser
        115                 120                 125
Arg Ser Thr Ser Glu Ser Thr Ala Ala Leu Gly Cys Leu Val Lys Asp
130                 135                 140
Tyr Phe Pro Glu Pro Val Thr Val Ser Trp Asn Ser Gly Ala Leu Thr
145                 150                 155                 160
Ser Gly Val His Thr Phe Pro Ala Val Leu Gln Ser Ser Gly Leu Tyr
                165                 170                 175
Ser Leu Ser Ser Val Val Thr Val Pro Ser Ser Ser Leu Gly Thr Lys
                180                 185                 190
Thr Tyr Thr Cys Asn Val Asp His Lys Pro Ser Asn Thr Lys Val Asp
        195                 200                 205
Lys Arg Val Glu Ser Lys Tyr Gly Pro Pro Cys Pro Pro Cys Pro Ala
        210                 215                 220
Pro Glu Phe Leu Gly Gly Pro Ser Val Phe Leu Phe Pro Pro Lys Pro
225                 230                 235                 240
Lys Asp Thr Leu Met Ile Ser Arg Thr Pro Glu Val Thr Cys Val Val
                245                 250                 255
Val Asp Val Ser Gln Glu Asp Pro Glu Val Gln Phe Asn Trp Tyr Val
                260                 265                 270
Asp Gly Val Glu Val His Asn Ala Lys Thr Lys Pro Arg Glu Glu Gln
        275                 280                 285
Phe Asn Ser Thr Tyr Arg Val Val Ser Val Leu Thr Val Leu His Gln
290                 295                 300
Asp Trp Leu Asn Gly Lys Glu Tyr Lys Cys Lys Val Ser Asn Lys Gly
305                 310                 315                 320
Leu Pro Ser Ser Ile Glu Lys Thr Ile Ser Lys Ala Lys Gly Gln Pro
                325                 330                 335
Arg Glu Pro Gln Val Tyr Thr Leu Pro Pro Ser Gln Glu Glu Met Thr
        340                 345                 350
Lys Asn Gln Val Ser Leu Thr Cys Leu Val Lys Gly Phe Tyr Pro Ser
        355                 360                 365
Asp Ile Ala Val Glu Trp Glu Ser Asn Gly Gln Pro Glu Asn Asn Tyr
370                 375                 380
Lys Thr Thr Pro Pro Val Leu Asp Ser Asp Gly Ser Phe Phe Leu Tyr
385                 390                 395                 400
Ser Arg Leu Thr Val Asp Lys Ser Arg Trp Gln Glu Gly Asn Val Phe
                405                 410                 415
Ser Cys Ser Val Met His Glu Ala Leu His Asn His Tyr Thr Gln Lys
        420                 425                 430
Ser Leu Ser Leu Ser Leu Gly
        435
```

<210> SEQ ID NO 53
<211> LENGTH: 439
<212> TYPE: PRT
<213> ORGANISM: Artificial Sequence
<220> FEATURE:
<223> OTHER INFORMATION: AGEN2034w heavy chain IgG4 S228P (without C-terminal lysine)

<400> SEQUENCE: 53

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Gly Asp His Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365
```

```
Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
                420                 425                 430

Ser Leu Ser Leu Ser Leu Gly
            435

<210> SEQ ID NO 54
<211> LENGTH: 442
<212> TYPE: PRT
<213> ORGANISM: Artificial Sequence
<220> FEATURE:
<223> OTHER INFORMATION: AGEN2046w heavy chain IgG1 (without C-terminal
      lysine)

<400> SEQUENCE: 54

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Val Asp Tyr Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285
```

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
        435                 440

<210> SEQ ID NO 55
<211> LENGTH: 442
<212> TYPE: PRT
<213> ORGANISM: Artificial Sequence
<220> FEATURE:
<223> OTHER INFORMATION: AGEN2047w heavy chain IgG1 (without C-terminal
      lysine)

<400> SEQUENCE: 55

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Gly Asp His Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp

```
                195                 200                 205
Lys Arg Val Glu Pro Lys Ser Cys Asp Lys Thr His Thr Cys Pro Pro
        210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
        260                 265                 270

Trp Tyr Val Asp Gly Val Glu Val His Asn Ala Lys Thr Lys Pro Arg
                275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
                340                 345                 350

Glu Met Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
        370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly
                435                 440

<210> SEQ ID NO 56
<211> LENGTH: 442
<212> TYPE: PRT
<213> ORGANISM: Artificial Sequence
<220> FEATURE:
<223> OTHER INFORMATION: AGEN2047w heavy chain IgG1 N297A (without C-
      terminal lysine)

<400> SEQUENCE: 56

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Gly Asp His Trp Gly Gln Gly Thr Leu Val Thr Val Ser
            100                 105                 110
```

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Ala Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
        435                 440

<210> SEQ ID NO 57
<211> LENGTH: 442
<212> TYPE: PRT
<213> ORGANISM: Artificial Sequence
<220> FEATURE:
<223> OTHER INFORMATION: AGEN2047w heavy chain IgG1 S267E/L328F (without
      C-terminal lysine)

<400> SEQUENCE: 57

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

```
Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Ser Asn Gly Asp His Trp Gly Gln Gly Thr Leu Val Thr Val Ser
            100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
        210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Glu His Glu Asp Pro Glu Val Lys Phe Asn
                260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Ala Phe Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
        435                 440
```

<210> SEQ ID NO 58
<211> LENGTH: 442
<212> TYPE: PRT
<213> ORGANISM: Artificial Sequence
<220> FEATURE:
<223> OTHER INFORMATION: AGEN2047w heavy chain IgG1 S239D/A330L/I332E
      (without C-terminal lysine)

<400> SEQUENCE: 58

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asn Gly Asp His Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
    210                 215                 220

Cys Pro Ala Pro Glu Leu Leu Gly Gly Pro Asp Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Leu Pro Glu Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365
```

Tyr Pro Ser Asp Ile Ala Val Glu Trp Glu Ser Asn Gly Gln Pro Glu
        370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
        435                 440

<210> SEQ ID NO 59
<211> LENGTH: 329
<212> TYPE: PRT
<213> ORGANISM: Homo sapiens

<400> SEQUENCE: 59

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 60
<211> LENGTH: 330
<212> TYPE: PRT
<213> ORGANISM: Homo sapiens

<400> SEQUENCE: 60

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 61
<211> LENGTH: 329
<212> TYPE: PRT
<213> ORGANISM: Artificial Sequence
<220> FEATURE:
<223> OTHER INFORMATION: IgG1 N297A (without C-terminal lysine)

<400> SEQUENCE: 61

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 62
<211> LENGTH: 330
<212> TYPE: PRT
<213> ORGANISM: Artificial Sequence
<220> FEATURE:

<223> OTHER INFORMATION: IgG1 N297A

<400> SEQUENCE: 62

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 63
<211> LENGTH: 326
<212> TYPE: PRT
<213> ORGANISM: Artificial Sequence
<220> FEATURE:
<223> OTHER INFORMATION: IgG4 S228P (without C-terminal lysine)

<400> SEQUENCE: 63

```
Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 64
<211> LENGTH: 327
<212> TYPE: PRT
<213> ORGANISM: Artificial Sequence
<220> FEATURE:
<223> OTHER INFORMATION: IgG4 S228P

<400> SEQUENCE: 64

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
         35                  40                  45
```

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
    195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 65
<211> LENGTH: 107
<212> TYPE: PRT
<213> ORGANISM: Homo sapiens

<400> SEQUENCE: 65

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser

```
                    85                  90                  95

Pro Val Thr Lys Ser Phe Asn Arg Gly Glu Cys
            100                 105

<210> SEQ ID NO 66
<211> LENGTH: 448
<212> TYPE: PRT
<213> ORGANISM: Artificial Sequence
<220> FEATURE:
<223> OTHER INFORMATION: pab2197 heavy chain

<400> SEQUENCE: 66

Glu Val Gln Leu Val Glu Ser Gly Gly Leu Thr Gln Pro Gly Lys
1               5                   10                  15

Ser Leu Lys Leu Ser Cys Glu Ala Ser Gly Phe Thr Phe Ser Ser Phe
                20                  25                  30

Thr Met His Trp Val Arg Gln Ser Pro Gly Lys Gly Leu Glu Trp Val
            35                  40                  45

Ala Phe Ile Arg Ser Gly Ser Gly Ile Val Phe Tyr Ala Asp Ala Val
        50                  55                  60

Arg Gly Arg Phe Thr Ile Ser Arg Asp Asn Ala Lys Asn Leu Leu Phe
65                  70                  75                  80

Leu Gln Met Asn Asp Leu Lys Ser Glu Asp Thr Ala Met Tyr Tyr Cys
                85                  90                  95

Ala Arg Arg Pro Leu Gly His Asn Thr Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
```

```
                340             345             350
Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445
```

<210> SEQ ID NO 67
<211> LENGTH: 220
<212> TYPE: PRT
<213> ORGANISM: Artificial Sequence
<220> FEATURE:
<223> OTHER INFORMATION: pab2197 light chain

<400> SEQUENCE: 67

```
Asp Ile Val Met Thr Gln Ser Pro Ser Ser Leu Ala Val Ser Pro Gly
1               5                   10                  15

Glu Lys Val Thr Met Thr Cys Lys Ser Ser Gln Ser Leu Tyr Tyr Ser
            20                  25                  30

Gly Val Lys Glu Asn Leu Leu Ala Trp Tyr Gln Gln Lys Pro Gly Gln
        35                  40                  45

Ser Pro Lys Leu Leu Ile Tyr Tyr Ala Ser Ile Arg Phe Thr Gly Val
    50                  55                  60

Pro Asp Arg Phe Thr Gly Ser Gly Ser Gly Thr Asp Tyr Thr Leu Thr
65                  70                  75                  80

Ile Thr Ser Val Gln Ala Glu Asp Met Gly Gln Tyr Phe Cys Gln Gln
                85                  90                  95

Gly Ile Asn Asn Pro Leu Thr Phe Gly Asp Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 68
<211> LENGTH: 448
<212> TYPE: PRT
<213> ORGANISM: Artificial Sequence
<220> FEATURE:
<223> OTHER INFORMATION: pab2196 heavy chain

<400> SEQUENCE: 68

```
Glu Val Gln Leu Gln Gln Ser Gly Pro Glu Leu Val Lys Pro Gly Thr
1               5                   10                  15
Ser Met Lys Ile Ser Cys Lys Ala Ser Gly Tyr Ser Phe Thr Gly His
            20                  25                  30
Leu Met Asn Trp Val Lys Gln Ser His Gly Lys Asn Leu Glu Trp Ile
        35                  40                  45
Gly Leu Ile Ile Pro Tyr Asn Gly Gly Thr Ser Tyr Asn Gln Lys Phe
    50                  55                  60
Lys Gly Lys Ala Thr Leu Thr Val Asp Lys Ser Ser Thr Ala Tyr
65                  70                  75                  80
Met Glu Leu Leu Ser Leu Thr Ser Asp Asp Ser Ala Val Tyr Phe Cys
                85                  90                  95
Ser Arg Gly Leu Arg Gly Phe Tyr Ala Met Asp Tyr Trp Gly Gln Gly
            100                 105                 110
Thr Ser Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
```

```
                            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 69
<211> LENGTH: 219
<212> TYPE: PRT
<213> ORGANISM: Artificial Sequence
<220> FEATURE:
<223> OTHER INFORMATION: pab2196 light chain

<400> SEQUENCE: 69

Asp Val Val Leu Thr Gln Thr Pro Leu Ser Leu Ser Val Ser Phe Gly
1               5                   10                  15

Asp Gln Val Ser Ile Ser Cys Arg Ser Ser Gln Ser Leu Val Asn Ser
            20                  25                  30

Tyr Gly Asn Thr Phe Leu Ser Trp Tyr Leu His Lys Pro Gly Gln Ser
        35                  40                  45

Pro Gln Leu Leu Ile Phe Gly Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Thr Ile Lys Pro Glu Asp Leu Gly Met Tyr Tyr Cys Leu Gln Gly
                85                  90                  95

Thr His Gln Pro Pro Thr Phe Gly Pro Gly Thr Lys Leu Glu Val Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 70
<211> LENGTH: 450
<212> TYPE: PRT
<213> ORGANISM: Artificial Sequence
<220> FEATURE:
<223> OTHER INFORMATION: pab2225 heavy chain

<400> SEQUENCE: 70

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45
```

```
Gly Glu Ile Asn His Gly Gly Tyr Val Thr Tyr Asn Pro Ser Leu Glu
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Tyr Gly Pro Gly Asn Tyr Asp Trp Tyr Phe Asp Leu Trp Gly
             100                 105                 110

Arg Gly Thr Leu Val Thr Val Ser Ala Ser Thr Lys Gly Pro Ser
         115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
450
```

-continued

```
<210> SEQ ID NO 71
<211> LENGTH: 216
<212> TYPE: PRT
<213> ORGANISM: Artificial Sequence
<220> FEATURE:
<223> OTHER INFORMATION: pab2225 light chain

<400> SEQUENCE: 71
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

```
<210> SEQ ID NO 72
<211> LENGTH: 451
<212> TYPE: PRT
<213> ORGANISM: Artificial Sequence
<220> FEATURE:
<223> OTHER INFORMATION: pab1928 heavy chain

<400> SEQUENCE: 72
```

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Lys Trp Met
        35                  40                  45

Gly Trp Ile Asn Thr Glu Thr Gly Glu Pro Thr Tyr Ala Asp Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Pro Tyr Tyr Asp Tyr Val Ser Tyr Ala Met Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 73
<211> LENGTH: 214
<212> TYPE: PRT
<213> ORGANISM: Artificial Sequence
<220> FEATURE:
<223> OTHER INFORMATION: pab1928 light chain

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Leu Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Arg
                85                  90                  95

Thr Phe Gly Gln Gly Thr Lys Leu Glu Ile Lys Arg Ser Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 74
<211> LENGTH: 268
<212> TYPE: PRT
<213> ORGANISM: Homo sapiens

<400> SEQUENCE: 74

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Val Trp Val Leu Ala Val Ile Cys Ser Arg Ala Ala
            165                 170                 175

Arg Gly Thr Ile Gly Ala Arg Thr Gly Gln Pro Leu Lys Glu Asp
        180                 185                 190

Pro Ser Ala Val Pro Val Phe Ser Val Asp Tyr Gly Glu Leu Asp Phe
        195                 200                 205

Gln Trp Arg Glu Lys Thr Pro Glu Pro Val Pro Cys Val Pro Glu
210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
            245                 250                 255

Leu Arg Pro Glu Asp Gly His Cys Ser Trp Pro Leu
            260                 265

<210> SEQ ID NO 75
<211> LENGTH: 16
<212> TYPE: PRT
<213> ORGANISM: Homo sapiens

<400> SEQUENCE: 75

Ser Leu Ala Pro Lys Ala Gln Ile Lys Glu Ser Leu Arg Ala Glu Leu
1               5                   10                  15

<210> SEQ ID NO 76
<211> LENGTH: 18
<212> TYPE: PRT
<213> ORGANISM: Homo sapiens

<400> SEQUENCE: 76

Leu Asp Ser Pro Asp Arg Pro Trp Asn Pro Thr Phe Ser Pro Ala
1               5                   10                  15

Leu Leu

<210> SEQ ID NO 77
<211> LENGTH: 10
<212> TYPE: PRT
<213> ORGANISM: Homo sapiens

<400> SEQUENCE: 77

Asp Ser Pro Asp Arg Pro Trp Asn Pro Pro
1               5                   10

<210> SEQ ID NO 78
<211> LENGTH: 9
<212> TYPE: PRT
<213> ORGANISM: Homo sapiens

<400> SEQUENCE: 78

Glu Val Pro Thr Ala His Pro Ser Pro
1               5

<210> SEQ ID NO 79
<211> LENGTH: 8
<212> TYPE: PRT
<213> ORGANISM: Homo sapiens

<400> SEQUENCE: 79

Ile Ser Leu Ala Pro Lys Ala Gln
1               5

ANTI-PD-1 ANTIBODIES AND METHODS OF USE THEREOF

CROSS-REFERENCE TO RELATED APPLICATIONS

This application is a continuation of U.S. patent application Ser. No. 15/254,315, filed Sep. 1, 2016 which claims priority to U.S. Provisional Application Nos. 62/212,851, filed Sep. 1, 2015; 62/216,043, filed Sep. 9, 2015; and 62/257,195, filed Nov. 18, 2015, each of which is incorporated by reference herein in its entirety.

1. FIELD

The instant disclosure relates to antibodies that specifically bind to human PD-1 and methods of using the same.

2. BACKGROUND

The protein programmed cell death protein 1 (PD-1) is an inhibitory member of the CD28 family of receptors. PD-1 is expressed on activated B cells, T cells, and myeloid cells (Agata et al. (1996) Int Immunol 8:765-72; Okazaki et al. (2002) Curr. Opin. Immunol. 14: 391779-82; Bennett et al. (2003) J Immunol 170:711-8). PD-1 is a 55 kDa type I transmembrane protein that is part of the Ig gene superfamily and contains a membrane proximal immunoreceptor tyrosine inhibitory motif (ITIM) and a membrane distal tyrosine-based switch motif (ITSM) (Thomas, M. L. (1995) J Exp Med 181:1953-6; Vivier, E and Daeron, M (1997) Immunol Today 18:286-91). Two ligands for PD-1 have been identified, PD-L1 and PD-L2, that have been shown to downregulate T cell activation upon binding to PD-1 (Freeman et al. (2000) J Exp Med 192:1027-34; Latchman et al. (2001) Nat Immunol 2:261-8; Carter et al. (2002) Eur J Immunol 32:634-43). PD-L1 is abundant in a variety of human cancers (Dong et al. (2002) Nat. Med. 8:787-9). The interaction between PD-1 and PD-L1 results in a decrease in tumor infiltrating lymphocytes, a decrease in T cell receptor mediated proliferation, and immune evasion by the cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). This immune suppression can be reversed by inhibiting the local interaction of PD-1 with PD-L1, and the effect is additive when the interaction of PD-1 with PD-L2 is blocked as well (Iwai et al. (2002) Proc. Nat'l. Acad. Sci. USA 99:12293-7; Brown et al. (2003) J. Immunol. 170:1257-66).

PD-1 is an immune cell inhibitory molecule. PD-1 deficient animals develop various autoimmune phenotypes, including autoimmune cardiomyopathy and a lupus-like syndrome with arthritis and nephritis (Nishimura et al. (1999) Immunity 11:141-51; Nishimura et al. (2001) Science 291:319-22). Additionally, PD-1 has been found to play a role in autoimmune encephalomyelitis, systemic lupus erythematosus, graft-versus-host disease (GVHD), type I diabetes, and rheumatoid arthritis (Salama et al. (2003) J Exp Med 198:71-78; Prokunina and Alarcon-Riquelme (2004) Hum Mol Genet 13:R143; Nielsen et al. (2004) Lupus 13:510). In a murine B cell tumor line, the ITSM of PD-1 was shown to be essential to block BCR-mediated $Ca^{2+}$-flux and tyrosine phosphorylation of downstream effector molecules (Okazaki et al. (2001) PNAS 98:13866-71).

Given the role of human PD-1 in modulating immune responses, therapeutic agents designed to antagonize PD-1 signaling hold great promise for the treatment of diseases that involve PD-1-mediated immune suppression.

3. SUMMARY

The instant disclosure provides antibodies that specifically bind to human PD-1 and antagonize PD-1 function, e.g., PD-1-mediated immune suppression. Also provided are pharmaceutical compositions comprising these antibodies, nucleic acids encoding these antibodies, expression vectors and host cells for making these antibodies, and methods of treating a subject using these antibodies. The antibodies disclosed herein are particularly useful for increasing T cell activation in response to an antigen (e.g., a tumor antigen or an infectious disease antigen) and/or decreasing Treg-mediated immune suppression, and hence for treating cancer in a subject or treating or preventing an infectious disease in a subject.

Accordingly, in one aspect, the instant disclosure provides an antibody or isolated antibody comprising a heavy chain variable region comprising complementarity determining regions CDRH1, CDRH2, and CDRH3 and a light chain variable region comprising complementarity determining regions CDRL1, CDRL2, and CDRL3, wherein: (a) CDRH1 comprises the amino acid sequence of SYGMH (SEQ ID NO: 1); (b) CDRH2 comprises the amino acid sequence of VIWX$_1$DGSNX$_2$YYADSVX$_3$G (SEQ ID NO: 32), wherein X$_1$ is Y or F; X$_2$ is K or E; and X$_3$ is K or M; (c) CDRH3 comprises the amino acid sequence of NX$_1$DX$_2$ (SEQ ID NO: 33), wherein X$_1$ is G or V; and X$_2$ is H or Y; (d) CDRL1 comprises the amino acid sequence of RASQSVSSNLA (SEQ ID NO: 4); (e) CDRL2 comprises the amino acid sequence of GASTRAT (SEQ ID NO: 5); and (f) CDRL3 comprises the amino acid sequence of QQYNNWPRT (SEQ ID NO: 6).

In certain embodiments, CDRH2 comprises an amino acid sequence selected from the group consisting of SEQ ID NOs: 2 and 34-36.

In certain embodiments, CDRH3 comprises an amino acid sequence selected from the group consisting of SEQ ID NOs: 3, 7, and 37.

In certain embodiments, CDRH1, CDRH2 and CDRH3 comprise the CDRH1, CDRH2 and CDRH3 amino acid sequences, respectively, set forth in SEQ ID NOs: 1, 2, and 3; 1, 2, and 7; 1, 2, and 37; 1, 34, and 7; 1, 35, and 7; or 1, 36, and 7.

In certain embodiments, the antibody comprises a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 1, 2, 3, 4, 5, and 6, respectively.

In certain embodiments, the antibody comprises a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 1, 2, 7, 4, 5, and 6, respectively.

In certain embodiments, the antibody comprises a heavy chain variable region comprising the amino acid sequence of SEQ ID NO: 49.

In certain embodiments, the antibody comprises a heavy chain variable region comprising an amino acid sequence which is at least 75%, 80%, 85%, 90%, 95%, or 100% identical to an amino acid sequence selected from the group consisting of SEQ ID NOs: 15, 17, and 26-31. In certain embodiments, the heavy chain variable region comprises an amino acid sequence selected from the group consisting of SEQ ID NOs: 15, 17, and 26-31. In certain embodiments, the heavy chain variable region comprises the amino acid sequence of SEQ ID NO: 15. In certain embodiments, the heavy chain variable region comprises the amino acid sequence of SEQ ID NO: 17. In certain embodiments, the heavy chain variable region comprises the amino acid sequence of SEQ ID NO: 26. In certain embodiments, the heavy chain variable region comprises the amino acid sequence of SEQ ID NO: 27. In certain embodiments, the heavy chain variable region comprises the amino acid sequence of SEQ ID NO: 28. In certain embodiments, the heavy chain variable region comprises the amino acid sequence of SEQ ID NO: 29. In certain embodiments, the heavy chain variable region comprises the amino acid sequence of SEQ ID NO: 30. In certain embodiments, the heavy chain variable region comprises the amino acid sequence of SEQ ID NO: 31. In certain embodiments, the antibody comprises a heavy chain comprising the amino acid sequence of SEQ ID NO: 18. In certain embodiments, the antibody comprises a heavy chain comprising the amino acid sequence of SEQ ID NO: 21. In certain embodiments, the antibody comprises a heavy chain comprising the amino acid sequence of SEQ ID NO: 20. In certain embodiments, the antibody comprises a heavy chain comprising the amino acid sequence of SEQ ID NO: 22. In certain embodiments, the antibody comprises a heavy chain comprising the amino acid sequence of SEQ ID NO: 23. In certain embodiments, the antibody comprises a heavy chain comprising the amino acid sequence of SEQ ID NO: 24. In certain embodiments, the antibody comprises a heavy chain comprising the amino acid sequence of SEQ ID NO: 25. In certain embodiments, the antibody comprises a heavy chain comprising the amino acid sequence of SEQ ID NO: 52. In certain embodiments, the antibody comprises a heavy chain comprising the amino acid sequence of SEQ ID NO: 53. In certain embodiments, the antibody comprises a heavy chain comprising the amino acid sequence of SEQ ID NO: 54. In certain embodiments, the antibody comprises a heavy chain comprising the amino acid sequence of SEQ ID NO: 55. In certain embodiments, the antibody comprises a heavy chain comprising the amino acid sequence of SEQ ID NO: 56. In certain embodiments, the antibody comprises a heavy chain comprising the amino acid sequence of SEQ ID NO: 57. In certain embodiments, the antibody comprises a heavy chain comprising the amino acid sequence of SEQ ID NO: 58.

In certain embodiments, the antibody comprises a heavy chain variable region having an amino acid sequence derived from a human IGHV3-33 germline sequence (e.g., IGHV3-33*01, e.g., having amino acid sequence of SEQ ID NO: 50).

In certain embodiments, the antibody comprises a light chain variable region comprising an amino acid sequence which is at least 75%, 80%, 85%, 90%, 95%, or 100% identical to the amino acid sequence of SEQ ID NO: 16. In certain embodiments, the light chain variable region comprises the amino acid sequence of SEQ ID NO: 16. In certain embodiments, the antibody comprises a light chain comprising the amino acid sequence of SEQ ID NO: 19.

In certain embodiments, the antibody comprises a light chain variable region having an amino acid sequence derived from a human IGKV3-15 germline sequence (e.g., IGKV3-15*01, e.g., having amino acid sequence of SEQ ID NO: 51).

In certain embodiments, the antibody comprises a heavy chain variable region and a light chain variable region, wherein the heavy chain variable region and the light chain variable region, respectively, comprise the amino acid sequences set forth in SEQ ID NOs: 15 and 16; 17 and 16; 26 and 16; 27 and 16; 28 and 16; 29 and 16; 30 and 16; or 31 and 16.

In another aspect, the instant disclosure provides an antibody or isolated antibody comprising: (a) a heavy chain variable region comprising the amino acid sequence of SEQ ID NO: 15, and (b) a light chain variable region comprising the amino acid sequence of SEQ ID NO: 16.

In another aspect, the instant disclosure provides an antibody or isolated antibody comprising: (a) a heavy chain variable region comprising the amino acid sequence of SEQ ID NO: 17, and (b) a light chain variable region comprising the amino acid sequence of SEQ ID NO: 16.

In another aspect, the instant disclosure provides an antibody or isolated antibody comprising: (a) a heavy chain variable region comprising the amino acid sequence of SEQ ID NO: 26, and (b) a light chain variable region comprising the amino acid sequence of SEQ ID NO: 16.

In another aspect, the instant disclosure provides an antibody or isolated antibody comprising: (a) a heavy chain variable region comprising the amino acid sequence of SEQ ID NO: 27, and (b) a light chain variable region comprising the amino acid sequence of SEQ ID NO: 16.

In another aspect, the instant disclosure provides an antibody or isolated antibody comprising: (a) a heavy chain variable region comprising the amino acid sequence of SEQ ID NO: 28, and (b) a light chain variable region comprising the amino acid sequence of SEQ ID NO: 16.

In another aspect, the instant disclosure provides an antibody or isolated antibody comprising: (a) a heavy chain variable region comprising the amino acid sequence of SEQ ID NO: 29, and (b) a light chain variable region comprising the amino acid sequence of SEQ ID NO: 16.

In another aspect, the instant disclosure provides an antibody or isolated antibody comprising: (a) a heavy chain variable region comprising the amino acid sequence of SEQ ID NO: 30, and (b) a light chain variable region comprising the amino acid sequence of SEQ ID NO: 16.

In another aspect, the instant disclosure provides an antibody or isolated antibody comprising: (a) a heavy chain variable region having an amino acid sequence derived from a human IGHV3-33 germline sequence (e.g., IGHV3-33*01, e.g., having amino acid sequence of SEQ ID NO: 50), and (b) a light chain variable region having an amino acid sequence derived from a human IGKV3-15 germline sequence (e.g., IGKV3-15*01, e.g., having amino acid sequence of SEQ ID NO: 51).

In another aspect, the instant disclosure provides an antibody or isolated antibody comprising: (a) a heavy chain variable region comprising the amino acid sequence of SEQ ID NO: 31, and (b) a light chain variable region comprising the amino acid sequence of SEQ ID NO: 16.

In another aspect, the instant disclosure provides an antibody or isolated antibody comprising a heavy chain variable region comprising an amino acid sequence selected from the group consisting of SEQ ID NOs: 15, 17, and 26-31.

In another aspect, the instant disclosure provides an antibody or isolated antibody comprising a light chain variable region comprising the amino acid sequence of SEQ ID NO: 16.

In another aspect, the instant disclosure provides an antibody or isolated antibody comprising: (a) a heavy chain comprising the amino acid sequence of SEQ ID NO: 18; and (b) a light chain comprising the amino acid sequence of SEQ ID NO: 19.

In another aspect, the instant disclosure provides an antibody or isolated antibody comprising: (a) a heavy chain comprising the amino acid sequence of SEQ ID NO: 20; and (b) a light chain comprising the amino acid sequence of SEQ ID NO: 19.

In another aspect, the instant disclosure provides an antibody or isolated antibody comprising: (a) a heavy chain comprising the amino acid sequence of SEQ ID NO: 21; and (b) a light chain comprising the amino acid sequence of SEQ ID NO: 19.

In another aspect, the instant disclosure provides an antibody or isolated antibody comprising: (a) a heavy chain comprising the amino acid sequence of SEQ ID NO: 22; and (b) a light chain comprising the amino acid sequence of SEQ ID NO: 19.

In another aspect, the instant disclosure provides an antibody or isolated antibody comprising: (a) a heavy chain comprising the amino acid sequence of SEQ ID NO: 23; and (b) a light chain comprising the amino acid sequence of SEQ ID NO: 19.

In another aspect, the instant disclosure provides an antibody or isolated antibody comprising: (a) a heavy chain comprising the amino acid sequence of SEQ ID NO: 52; and (b) a light chain comprising the amino acid sequence of SEQ ID NO: 19.

In another aspect, the instant disclosure provides an antibody or isolated antibody comprising: (a) a heavy chain comprising the amino acid sequence of SEQ ID NO: 53; and (b) a light chain comprising the amino acid sequence of SEQ ID NO: 19.

In another aspect, the instant disclosure provides an antibody or isolated antibody comprising: (a) a heavy chain comprising the amino acid sequence of SEQ ID NO: 54; and (b) a light chain comprising the amino acid sequence of SEQ ID NO: 19.

In another aspect, the instant disclosure provides an antibody or isolated antibody comprising: (a) a heavy chain comprising the amino acid sequence of SEQ ID NO: 55; and (b) a light chain comprising the amino acid sequence of SEQ ID NO: 19.

In another aspect, the instant disclosure provides an antibody or isolated antibody comprising: (a) a heavy chain comprising the amino acid sequence of SEQ ID NO: 56; and (b) a light chain comprising the amino acid sequence of SEQ ID NO: 19.

In another aspect, the instant disclosure provides an antibody or isolated antibody that specifically binds to human PD-1 comprising a heavy chain variable region comprising complementarity determining regions CDRH1, CDRH2, and CDRH3 and a light chain variable region comprising complementarity determining regions CDRL1, CDRL2, and CDRL3, wherein: (a) CDRH1 comprises the amino acid sequence of SYGMH (SEQ ID NO: 1); (b) CDRH2 comprises the amino acid sequence of VIWX$_1$DGSNX$_2$YYADSVX$_3$G (SEQ ID NO: 32), wherein X$_1$ is Y or F; X$_2$ is K or E; and X$_3$ is K or M; (c) CDRH3 comprises the amino acid sequence of NX$_1$DX$_2$ (SEQ ID NO: 33), wherein X$_1$ is G or V; and X$_2$ is H or Y; (d) CDRL1 comprises the amino acid sequence of RASQSVSSNLA (SEQ ID NO: 4); (e) CDRL2 comprises the amino acid sequence of GASTRAT (SEQ ID NO: 5); and (f) CDRL3 comprises the amino acid sequence of QQYNNWPRT (SEQ ID NO: 6).

In certain embodiments, CDRH2 comprises an amino acid sequence selected from the group consisting of SEQ ID NOs: 2 and 34-36.

In certain embodiments, CDRH3 comprises an amino acid sequence selected from the group consisting of SEQ ID NOs: 3, 7, and 37.

In certain embodiments, CDRH1, CDRH2 and CDRH3 comprise the CDRH1, CDRH2 and CDRH3 amino acid sequences, respectively, set forth in SEQ ID NOs: 1, 2, and 3; 1, 2, and 7; 1, 2, and 37; 1, 34, and 7; 1, 35, and 7; or 1, 36, and 7.

In certain embodiments, the antibody comprises a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 1, 2, 3, 4, 5, and 6, respectively.

In certain embodiments, the antibody comprises a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 1, 2, 7, 4, 5, and 6, respectively.

In certain embodiments, the antibody comprises a heavy chain variable region comprising the amino acid sequence of SEQ ID NO: 49.

In certain embodiments, the antibody comprises a heavy chain variable region comprising an amino acid sequence which is at least 75%, 80%, 85%, 90%, 95%, or 100% identical to an amino acid sequence selected from the group consisting of SEQ ID NOs: 15, 17, and 26-31. In certain embodiments, the heavy chain variable region comprises an amino acid sequence selected from the group consisting of SEQ ID NOs: 15, 17, and 26-31. In certain embodiments, the heavy chain variable region comprises the amino acid sequence of SEQ ID NO: 15. In certain embodiments, the heavy chain variable region comprises the amino acid sequence of SEQ ID NO: 17. In certain embodiments, the heavy chain variable region comprises the amino acid sequence of SEQ ID NO: 26. In certain embodiments, the heavy chain variable region comprises the amino acid sequence of SEQ ID NO: 27. In certain embodiments, the heavy chain variable region comprises the amino acid sequence of SEQ ID NO: 28. In certain embodiments, the heavy chain variable region comprises the amino acid sequence of SEQ ID NO: 29. In certain embodiments, the heavy chain variable region comprises the amino acid sequence of SEQ ID NO: 30. In certain embodiments, the heavy chain variable region comprises the amino acid sequence of SEQ ID NO: 31. In certain embodiments, the antibody comprises a heavy chain comprising the amino acid sequence of SEQ ID NO: 18. In certain embodiments, the antibody comprises a heavy chain comprising the amino acid sequence of SEQ ID NO: 21. In certain embodiments, the antibody comprises a heavy chain comprising the amino acid sequence of SEQ ID NO: 20. In certain embodiments, the antibody comprises a heavy chain comprising the amino acid sequence of SEQ ID NO: 22. In certain embodiments, the antibody comprises a heavy chain comprising the amino acid sequence of SEQ ID NO: 23. In certain embodiments, the antibody comprises a heavy chain comprising the amino acid sequence of SEQ ID NO: 24. In certain embodiments, the antibody comprises a heavy chain comprising the amino acid sequence of SEQ ID NO: 25. In certain embodiments, the antibody comprises a heavy chain comprising the amino acid sequence of SEQ ID NO: 52. In certain embodiments, the antibody comprises a heavy chain comprising the amino acid sequence of SEQ ID NO: 53. In certain embodiments, the antibody comprises a heavy chain comprising the amino acid sequence of SEQ ID NO: 54. In certain embodiments, the antibody comprises a heavy chain comprising the amino acid sequence of SEQ ID NO: 55. In certain embodiments, the antibody comprises a heavy chain comprising the amino acid sequence of SEQ ID NO: 56. In certain embodiments, the antibody comprises a heavy chain comprising the amino acid sequence of SEQ ID NO: 57. In certain embodiments, the antibody comprises a heavy chain comprising the amino acid sequence of SEQ ID NO: 58.

In certain embodiments, the antibody comprises a heavy chain variable region having an amino acid sequence derived from a human IGHV3-33 germline sequence (e.g., IGHV3-33*01, e.g., having amino acid sequence of SEQ ID NO: 50).

In certain embodiments, the antibody comprises a light chain variable region comprising an amino acid sequence which is at least 75%, 80%, 85%, 90%, 95%, or 100% identical to the amino acid sequence of SEQ ID NO: 16. In certain embodiments, the light chain variable region comprises the amino acid sequence of SEQ ID NO: 16. In certain embodiments, the antibody comprises a light chain comprising the amino acid sequence of SEQ ID NO: 19.

In certain embodiments, the antibody comprises a light chain variable region having an amino acid sequence derived from a human IGKV3-15 germline sequence (e.g., IGKV3-15*01, e.g., having amino acid sequence of SEQ ID NO: 51).

In certain embodiments, the antibody comprises a heavy chain variable region and a light chain variable region, wherein the heavy chain variable region and the light chain variable region, respectively, comprise the amino acid sequences set forth in SEQ ID NOs: 15 and 16; 17 and 16; 26 and 16; 27 and 16; 28 and 16; 29 and 16; 30 and 16; or 31 and 16.

In another aspect, the instant disclosure provides an antibody or isolated antibody that specifically binds to human PD-1, comprising: (a) a heavy chain variable region comprising the amino acid sequence of SEQ ID NO: 15, and (b) a light chain variable region comprising the amino acid sequence of SEQ ID NO: 16.

In another aspect, the instant disclosure provides an antibody or isolated antibody that specifically binds to human PD-1, comprising: (a) a heavy chain variable region comprising the amino acid sequence of SEQ ID NO: 17, and (b) a light chain variable region comprising the amino acid sequence of SEQ ID NO: 16.

In another aspect, the instant disclosure provides an antibody or isolated antibody that specifically binds to human PD-1, comprising: (a) a heavy chain variable region comprising the amino acid sequence of SEQ ID NO: 26, and (b) a light chain variable region comprising the amino acid sequence of SEQ ID NO: 16.

In another aspect, the instant disclosure provides an antibody or isolated antibody that specifically binds to human PD-1, comprising: (a) a heavy chain variable region comprising the amino acid sequence of SEQ ID NO: 27, and (b) a light chain variable region comprising the amino acid sequence of SEQ ID NO: 16.

In another aspect, the instant disclosure provides an antibody or isolated antibody that specifically binds to human PD-1, comprising: (a) a heavy chain variable region comprising the amino acid sequence of SEQ ID NO: 28, and (b) a light chain variable region comprising the amino acid sequence of SEQ ID NO: 16.

In another aspect, the instant disclosure provides an antibody or isolated antibody that specifically binds to human PD-1, comprising: (a) a heavy chain variable region comprising the amino acid sequence of SEQ ID NO: 29, and (b) a light chain variable region comprising the amino acid sequence of SEQ ID NO: 16.

In another aspect, the instant disclosure provides an antibody or isolated antibody that specifically binds to human PD-1, comprising: (a) a heavy chain variable region comprising the amino acid sequence of SEQ ID NO: 30, and (b) a light chain variable region comprising the amino acid sequence of SEQ ID NO: 16.

In another aspect, the instant disclosure provides an antibody or isolated antibody that specifically binds to human PD-1, comprising: (a) a heavy chain variable region comprising the amino acid sequence of SEQ ID NO: 31, and (b) a light chain variable region comprising the amino acid sequence of SEQ ID NO: 16.

In another aspect, the instant disclosure provides an antibody or isolated antibody that specifically binds to human PD-1, comprising: (a) a heavy chain variable region having an amino acid sequence derived from a human IGHV3-33 germline sequence (e.g., IGHV3-33*01, e.g., having amino acid sequence of SEQ ID NO: 50), and (b) a light chain variable region having an amino acid sequence derived from a human IGKV3-15 germline sequence (e.g., IGKV3-15*01, e.g., having amino acid sequence of SEQ ID NO: 51).

In another aspect, the instant disclosure provides an antibody or isolated antibody that specifically binds to human PD-1, comprising a heavy chain variable region comprising an amino acid sequence selected from the group consisting of SEQ ID NOs: 15, 17, and 26-31.

In another aspect, the instant disclosure provides an antibody or isolated antibody that specifically binds to human PD-1, comprising a light chain variable region comprising the amino acid sequence of SEQ ID NO: 16.

In another aspect, the instant disclosure provides an antibody or isolated antibody that specifically binds to human PD-1, comprising: (a) a heavy chain comprising the amino acid sequence of SEQ ID NO: 18; and (b) a light chain comprising the amino acid sequence of SEQ ID NO: 19.

In another aspect, the instant disclosure provides an antibody or isolated antibody that specifically binds to human PD-1, comprising: (a) a heavy chain comprising the amino acid sequence of SEQ ID NO: 20; and (b) a light chain comprising the amino acid sequence of SEQ ID NO: 19.

In another aspect, the instant disclosure provides an antibody or isolated antibody that specifically binds to human PD-1, comprising: (a) a heavy chain comprising the amino acid sequence of SEQ ID NO: 21; and (b) a light chain comprising the amino acid sequence of SEQ ID NO: 19.

In another aspect, the instant disclosure provides an antibody or isolated antibody that specifically binds to human PD-1, comprising: (a) a heavy chain comprising the amino acid sequence of SEQ ID NO: 22; and (b) a light chain comprising the amino acid sequence of SEQ ID NO: 19.

In another aspect, the instant disclosure provides an antibody or isolated antibody that specifically binds to human PD-1, comprising: (a) a heavy chain comprising the amino acid sequence of SEQ ID NO: 23; and (b) a light chain comprising the amino acid sequence of SEQ ID NO: 19.

In another aspect, the instant disclosure provides an antibody or isolated antibody that specifically binds to human PD-1, comprising: (a) a heavy chain comprising the amino acid sequence of SEQ ID NO: 52; and (b) a light chain comprising the amino acid sequence of SEQ ID NO: 19.

In another aspect, the instant disclosure provides an antibody or isolated antibody that specifically binds to human PD-1, comprising: (a) a heavy chain comprising the amino acid sequence of SEQ ID NO: 53; and (b) a light chain comprising the amino acid sequence of SEQ ID NO: 19.

In another aspect, the instant disclosure provides an antibody or isolated antibody that specifically binds to human PD-1, comprising: (a) a heavy chain comprising the amino acid sequence of SEQ ID NO: 54; and (b) a light chain comprising the amino acid sequence of SEQ ID NO: 19.

In another aspect, the instant disclosure provides an antibody or isolated antibody that specifically binds to human PD-1, comprising: (a) a heavy chain comprising the amino acid sequence of SEQ ID NO: 55; and (b) a light chain comprising the amino acid sequence of SEQ ID NO: 19.

In another aspect, the instant disclosure provides an antibody or isolated antibody that specifically binds to human PD-1, comprising: (a) a heavy chain comprising the amino acid sequence of SEQ ID NO: 56; and (b) a light chain comprising the amino acid sequence of SEQ ID NO: 19.

In another aspect, the instant disclosure provides an antibody or isolated antibody that cross-competes for binding to human PD-1 with any antibody disclosed herein. In another aspect the instant disclosure provides an antibody or isolated antibody that binds, e.g., specifically binds, to the same epitope of human PD-1 as any antibody disclosed herein.

In another aspect, the instant disclosure provides an antibody that binds, e.g., specifically binds, to an epitope of human PD-1. In certain embodiments, the antibody binds to an epitope of human PD-1 comprising, consisting essentially of, or consisting of residues 107-122 of SEQ ID NO: 74. In certain embodiments, the antibody binds to an epitope of human PD-1 consisting of residues 107-122 of SEQ ID NO: 74. In certain embodiments, the antibody binds to an epitope of human PD-1 comprising, consisting essentially of, or consisting of residues 5-22 of SEQ ID NO: 74. In certain embodiments, the antibody binds to an epitope of human PD-1 consisting of residues 5-22 of SEQ ID NO: 74. In certain embodiments, the antibody binds to an epitope of human PD-1 comprising, consisting essentially of, or consisting of residues 6-15 of SEQ ID NO: 74. In certain embodiments, the antibody binds to an epitope of human PD-1 consisting of residues 6-15 of SEQ ID NO: 74. In certain embodiments, the antibody binds to an epitope of human PD-1 comprising, consisting essentially of, or consisting of residues 130-138 of SEQ ID NO: 74. In certain embodiments, the antibody binds to an epitope of human PD-1 consisting of residues 130-138 of SEQ ID NO: 74. In certain embodiments, the antibody binds to an epitope of human PD-1 comprising, consisting essentially of, or consisting of residues 106-113 of SEQ ID NO: 74. In certain embodiments, the antibody binds to an epitope of human PD-1 consisting of residues 106-113 of SEQ ID NO: 74.

In another aspect, the instant disclosure provides an antibody for which, upon binding of the antibody to human PD-1 protein followed by addition of deuterium, the exchange of hydrogen in the human PD-1 protein with deuterium in a region comprising residues 107-122 of SEQ ID NO: 74 is substantially reduced relative to the exchange of hydrogen in the human PD-1 protein with deuterium in the same region in the absence of the antibody, as determined by hydrogen/deuterium exchange. In another aspect, the instant disclosure provides an antibody for which, upon binding of the antibody to human PD-1 protein followed by addition of deuterium, the exchange of hydrogen in the human PD-1 protein with deuterium in a region comprising residues 5-22 of SEQ ID NO: 74 is substantially reduced relative to the exchange of hydrogen in the human PD-1 protein with deuterium in the same region in the absence of the antibody, as determined by hydrogen/deuterium exchange.

In another aspect, the instant disclosure provides an antibody or isolated antibody that binds, e.g., specifically binds, to the same epitope of human PD-1 as any antibody of the present invention. In a preferred embodiment, the antibody binds to an epitope of human PD-1 comprising, consisting essentially of, or consisting of residues 107-122 of SEQ ID NO: 74. In another preferred embodiment, the antibody binds to an epitope of human PD-1 consisting of residues 107-122 of SEQ ID NO: 74. In another preferred embodiment, the antibody binds to an epitope of human PD-1 comprising, consisting essentially of, or consisting of residues 5-22 of SEQ ID NO: 74. In another preferred embodiment, the antibody binds to an epitope of human PD-1 consisting of residues 5-22 of SEQ ID NO: 74. In another preferred embodiment, the antibody binds to an epitope of human PD-1 comprising, consisting essentially of, or consisting of residues 6-15 of SEQ ID NO: 74. In another preferred embodiment, the antibody binds to an epitope of human PD-1 consisting of residues 6-15 of SEQ ID NO: 74. In another preferred embodiment, the antibody binds to an epitope of human PD-1 comprising, consisting essentially of, or consisting of residues 130-138 of SEQ ID NO: 74. In another preferred embodiment, the antibody binds to an epitope of human PD-1 consisting of residues 130-138 of SEQ ID NO: 74. In another preferred embodiment, the antibody binds to an epitope of human PD-1 comprising, consisting essentially of, or consisting of residues 106-113 of SEQ ID NO: 74. In another preferred embodiment, the antibody binds to an epitope of human PD-1 consisting of residues 106-113 of SEQ ID NO: 74. In a further preferred embodiment, the antibody binds to an epitope of human PD-1 comprising, consisting essentially of, or consisting of residues 6-15 of SEQ ID NO: 74, and/or an epitope of human PD-1 comprising, consisting essentially of, or consisting of residues 130-138 of SEQ ID NO: 74, and/or comprising, consisting essentially of, or consisting of residues 106-113 of SEQ ID NO: 74. The binding to an epitope is preferably determined by Pepscan analysis, in particular as described in the Examples. For example, binding to more than one above epitope sequences of human PD-1 may occur in the case of discontinuous epitopes.

In another aspect, the instant disclosure provides an antibody or isolated antibody that binds, e.g., specifically binds, to the same epitope of human PD-1 as any antibody of the present invention, for which, upon binding of the antibody to human PD-1 protein followed by addition of deuterium, the exchange of hydrogen in the human PD-1 protein with deuterium in a region comprising residues 107-122 of SEQ ID NO: 74 is substantially reduced relative to the exchange of hydrogen in the human PD-1 protein with deuterium in the same region in the absence of the antibody, as determined by hydrogen/deuterium exchange. In another aspect, the instant disclosure provides an antibody or isolated antibody that binds, e.g., specifically binds, to the same epitope of human PD-1 as any antibody of the present invention, and for which, upon binding of the antibody to human PD-1 protein followed by addition of deuterium, the exchange of hydrogen in the human PD-1 protein with deuterium in a region comprising residues 5-22 of SEQ ID NO: 74 is substantially reduced relative to the exchange of hydrogen in the human PD-1 protein with deuterium in the same region in the absence of the antibody, as determined by hydrogen/deuterium exchange. In a more preferred embodiment, upon binding of the antibody to human PD-1 protein followed by addition of deuterium, the exchange of hydrogen in the human PD-1 protein with deuterium in a region comprising residues 107-122 of SEQ ID NO: 74 is substantially reduced relative to the exchange of hydrogen in the human PD-1 protein with deuterium in the same region in the absence of the antibody, as determined by hydrogen/deuterium exchange, and, upon binding of the antibody to human PD-1 protein followed by addition of deuterium, the exchange of hydrogen in the human PD-1 protein with deuterium in a region comprising residues 5-22 of SEQ ID NO: 74 is substantially reduced relative to the exchange of hydrogen in the human PD-1 protein with deuterium in the same region in the absence of the antibody, as determined by hydrogen/deuterium exchange. For example, binding to more than one above epitope sequences of human PD-1 may occur in the case of discontinuous epitopes.

In another aspect, the instant disclosure provides an antibody or isolated antibody that binds, e.g., specifically binds, to the same epitope of human PD-1 as any antibody of the present invention, wherein the epitope is determined by hydrogen-deuterium exchange (HDX), in particular as described in the examples, or by Pepscan analysis, in particular as described in the examples, more preferably by hydrogen-deuterium exchange.

The following embodiments apply to all of the foregoing aspects.

In certain embodiments, the antibody comprises a heavy chain constant region selected from the group consisting of human $IgG_1$, $IgG_2$, $IgG_3$, $IgG_4$, $IgA_1$, and $IgA_2$. In certain embodiments, the antibody comprises a human $IgG_1$ heavy chain constant region. In certain embodiments, the antibody comprises a human $IgG_1$ heavy chain constant region that lacks a glycan moiety at position N297, according to the EU numbering system. In certain embodiments, the antibody comprises a human $IgG_1$ heavy chain constant region comprising an N297A mutation, according to the EU numbering system. In certain embodiments, the antibody comprises a human $IgG_1$ heavy chain constant region comprising an N297Q mutation, according to the EU numbering system. In certain embodiments, the antibody comprises a human $IgG_1$ heavy chain constant region comprising a D265A mutation, according to the EU numbering system. In certain embodiments, the antibody comprises a human $IgG_4$ heavy chain constant region comprising an S228P mutation, according to the EU numbering system.

In certain embodiments, the antibody comprises a human IgG heavy chain constant region that is a variant of a wild type human IgG heavy chain constant region, wherein the variant human IgG heavy chain constant region binds to human Fc receptor with lower affinity than the wild type human IgG heavy chain constant region binds to the human Fc receptor. In certain embodiments, the human Fc receptor is an FcγR. In certain embodiments, the FcγR is FcγRIIB. In certain embodiments, the FcγR is expressed on a cell selected from the group consisting of dendritic cells, monocytes, macrophages, neutrophils, granulocytes, B cells, and natural killer cells. In certain embodiments, the variant human IgG heavy chain constant region is a variant human $IgG_1$, a variant human $IgG_2$, or a variant human $IgG_4$ heavy chain constant region. In certain embodiments, the antibody comprises a light chain constant region selected from the group consisting of human IgGκ and IgGλ.

In certain embodiments, the antibody is a human antibody. In certain embodiments, the antibody is antagonistic to human PD-1. In certain embodiments, the antibody deactivates, reduces, or inhibits an activity of human PD-1. In certain embodiments, the antibody inhibits binding of human PD-1 to human PD-L1 or to human PD-L2. In certain embodiments, the antibody increases IL-2 production by peripheral blood mononuclear cells (PBMCs) stimulated with staphylococcal enterotoxin A (SEA). In certain embodiments, the antibody increases IFNγ production of a co-culture of human T cells and allogenic dendritic cells. In certain embodiments, the antibody increases proliferation of anti-CD3-antibody-stimulated CD4+ or CD8+ T cells co-cultured with ovarian cancer ascites fluid. In certain embodiments, the antibody increases NFAT signaling in PD-1-expressing NFAT-luciferase reporter cells co-cultured with PD-L1-expressing target cells.

In certain embodiments, an antibody disclosed herein is conjugated to a cytotoxic agent, cytostatic agent, toxin, radionuclide, or detectable label.

In another aspect, the instant disclosure provides a pharmaceutical composition comprising an antibody disclosed herein and a pharmaceutically acceptable carrier or excipient.

In another aspect, the instant disclosure provides a polynucleotide or isolated polynucleotide encoding a heavy and/or light chain of an antibody disclosed herein. In another aspect, the instant disclosure provides a vector comprising the polynucleotide. In yet another aspect, the instant disclosure provides a recombinant host cell comprising the polynucleotide or the vector. In a further aspect, the instant disclosure provides a method of producing an antibody that binds to human PD-1, the method comprising culturing the host cell so that the polynucleotide is expressed and the antibody is produced. In a preferred embodiment, the method is an in vitro method.

In one embodiment, the present invention relates to an antibody of the invention, or a pharmaceutical composition of the invention, or a polynucleotide of the invention, or a vector of the invention, or a recombinant host cell of the invention for use as a medicament.

In one embodiment, the present invention relates to an antibody of the invention, or a pharmaceutical composition of the invention, or a polynucleotide of the invention, or a vector of the invention, or a recombinant host cell of the invention for use as a diagnostic.

In one embodiment, the present invention relates to the use of an antibody of the present invention for preparing pharmaceutical compositions or medicaments for immunotherapy. Preferably, the immunotherapy is for increasing the activity of T cells, optionally for treating cancer or treating or preventing an infectious disease.

In another aspect, the instant disclosure provides a method of increasing T cell activation in response to an antigen in a subject, the method comprising administering to the subject an effective amount of an antibody or pharmaceutical composition disclosed herein.

In another aspect, the instant disclosure provides a method of treating cancer in a subject, the method comprising administering to the subject an effective amount of an antibody or pharmaceutical composition disclosed herein. In certain embodiments, the cancer is selected from the group consisting of melanoma, head and neck cancer (e.g., head and neck squamous cancer), lung cancer (e.g., non-small cell lung cancer and small cell lung cancer), breast cancer (e.g., herceptin resistant breast cancer and trastuzumab-DM1 (T-DM1) resistant breast cancer), prostate cancer, glioblastoma multiforme, colorectal cancer, sarcoma, bladder cancer, cervical cancer, HPV-associated cancers, cancers of the vagina, cancers of the vulva, cancers of the penis, cancers of the anus, cancers of the rectum, cancers of the oropharynx, multiple myeloma, renal cell carcinoma, ovarian cancer, hepatocellular cancer, endometrial cancer, pancreatic cancer, lymphoma, and leukemia (e.g., elderly leukemia, acute myeloid leukemia (AML), and elderly AML). In certain embodiments, the antibody or pharmaceutical composition is administered subcutaneously or intravenously. In certain embodiments, the antibody or pharmaceutical composition is administered intratumorally. In certain embodiments, the antibody or pharmaceutical composition is delivered to a tumor draining lymph node. In certain embodiments, the antibody or pharmaceutical composition is administered intra-arterially.

In one aspect, the present invention relates to an antibody, polynucleotide, vector, recombinant host cell, and/or pharmaceutical composition of the present invention for use in a method for increasing T cell activation in response to an antigen.

In one aspect, the present invention relates to an antibody, polynucleotide, vector, recombinant host cell, and/or pharmaceutical composition of the present invention for use in a method for increasing T cell activation in response to an antigen in a subject.

In one aspect, the present invention relates to the use of an antibody, polynucleotide, vector, recombinant host cell, and/or pharmaceutical composition of the present invention for preparing a pharmaceutical composition for increasing T cell activation in response to an antigen in a subject.

In one aspect, the present invention relates to an antibody, polynucleotide, vector, recombinant host cell, and/or pharmaceutical composition of the present invention for use in a method for increasing T cell activation in response to an antigen in a subject comprising administering to the subject an effective amount of an antibody, polynucleotide, vector, recombinant host cell, and/or pharmaceutical composition of the invention.

In one aspect, the present invention relates to an antibody, polynucleotide, vector, recombinant host cell, and/or pharmaceutical composition of the present invention for use in a method for the treatment of cancer, preferably wherein the cancer is selected from the group consisting of melanoma, head and neck cancer (e.g., head and neck squamous cancer), lung cancer (e.g., non-small cell lung cancer and small cell lung cancer), breast cancer (e.g., herceptin resistant breast cancer and trastuzumab-DM1 (T-DM1) resistant breast cancer), prostate cancer, glioblastoma multiforme, colorectal cancer, sarcoma, bladder cancer, cervical cancer, HPV-associated cancers, cancers of the vagina, cancers of the vulva, cancers of the penis, cancers of the anus, cancers of the rectum, cancers of the oropharynx, multiple myeloma, renal cell carcinoma, ovarian cancer, hepatocellular cancer, endometrial cancer, pancreatic cancer, lymphoma, and leukemia (e.g., elderly leukemia, acute myeloid leukemia (AML), and elderly AML).

In one aspect, the present invention relates to an antibody, polynucleotide, vector, recombinant host cell, and/or pharmaceutical composition of the present invention for use in a method for the treatment of cancer in a subject, preferably wherein the cancer is selected from the group consisting of melanoma, head and neck cancer (e.g., head and neck squamous cancer), lung cancer (e.g., non-small cell lung cancer and small cell lung cancer), breast cancer (e.g., herceptin resistant breast cancer and trastuzumab-DM1 (T-DM1) resistant breast cancer), prostate cancer, glioblastoma multiforme, colorectal cancer, sarcoma, bladder cancer, cervical cancer, HPV-associated cancers, cancers of the vagina, cancers of the vulva, cancers of the penis, cancers of the anus, cancers of the rectum, cancers of the oropharynx, multiple myeloma, renal cell carcinoma, ovarian cancer, hepatocellular cancer, endometrial cancer, pancreatic cancer, lymphoma, and leukemia (e.g., elderly leukemia, acute myeloid leukemia (AML), and elderly AML).

In one aspect, the present invention relates to an antibody, polynucleotide, vector, recombinant host cell, and/or pharmaceutical composition of the present invention for use in a method for the treatment of cancer in a subject comprising administering to the subject an effective amount of an antibody, polynucleotide, vector, recombinant host cell, and/or pharmaceutical composition of the invention, preferably wherein the cancer is selected from the group consisting of melanoma, head and neck cancer (e.g., head and neck squamous cancer), lung cancer (e.g., non-small cell lung cancer and small cell lung cancer), breast cancer (e.g., herceptin resistant breast cancer and trastuzumab-DM1 (T-DM1) resistant breast cancer), prostate cancer, glioblastoma multiforme, colorectal cancer, sarcoma, bladder cancer, cervical cancer, HPV-associated cancers, cancers of the vagina, cancers of the vulva, cancers of the penis, cancers of the anus, cancers of the rectum, cancers of the oropharynx, multiple myeloma, renal cell carcinoma, ovarian cancer, hepatocellular cancer, endometrial cancer, pancreatic cancer, lymphoma, and leukemia (e.g., elderly leukemia, acute myeloid leukemia (AML), and elderly AML).

In a preferred embodiment of an antibody, polynucleotide, vector, recombinant host cell, and/or pharmaceutical composition for use of the present invention, the antibody, polynucleotide, vector, recombinant host cell, and/or pharmaceutical composition, more preferably the antibody or pharmaceutical composition, is administered subcutaneously or intravenously. In another preferred embodiment of an antibody, polynucleotide, vector, recombinant host cell, and/or pharmaceutical composition for use of the present invention, the antibody, polynucleotide, vector, recombinant host cell, and/or pharmaceutical composition, more preferably the antibody or pharmaceutical composition, is administered intratumorally or intra-arterially.

In certain embodiments, the foregoing methods further comprise administering an additional therapeutic agent to the subject. Therefore, in one preferred embodiment of an antibody, polynucleotide, vector, recombinant host cell, and/or pharmaceutical composition for use in a method of the present invention, the method further comprises administering an additional therapeutic agent to the subject.

In one aspect, the present invention relates to (a) an antibody, polynucleotide, vector, recombinant host cell, and/or pharmaceutical composition of the present invention and (b) an additional therapeutic agent for use as a medicament.

In one aspect, the present invention relates to (a) an antibody, polynucleotide, vector, recombinant host cell, and/or pharmaceutical composition of the present invention and (b) an additional therapeutic agent for use in a method for the treatment of cancer.

In one aspect, the present invention relates to a pharmaceutical composition, kit or kit-of-parts comprising (a) an antibody, polynucleotide, vector, recombinant host cell, and/or pharmaceutical composition of the present invention and (b) an additional therapeutic agent.

In certain embodiments, the additional therapeutic agent is a chemotherapeutic or a checkpoint targeting agent. In certain embodiments, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAM1 antibody, an antagonist anti-TIGIT antibody, an agonist anti-CD137 antibody, an agonist anti-ICOS antibody, an agonist anti-GITR antibody, and an agonist anti-OX40 antibody. In certain embodiments, the additional therapeutic agent is an inhibitor of indoleamine-2,3-dioxygenase (IDO). In certain embodiments, the inhibitor is selected from the group consisting of epacadostat, F001287, indoximod, and NLG919. In certain embodiments, the additional therapeutic agent is a vaccine. In certain embodiments, the vaccine comprises a heat shock protein peptide complex (HSPPC) comprising a heat shock protein complexed with an antigenic peptide. In certain embodiments, the heat shock protein is hsc70 and is complexed with a tumor-associated antigenic peptide. In certain embodiments, the heat shock protein is gp96 protein and is complexed with a tumor-associated antigenic peptide, wherein the HSPPC is derived from a tumor obtained from a subject. In certain embodiments, the additional therapeutic agent comprises a TCR. In certain embodiments, the additional therapeutic agent is a soluble TCR. In certain embodiments, the additional therapeutic agent is a cell expressing a TCR. In certain embodiments, the additional therapeutic agent is a cell expressing a chimeric antigen receptor. In certain embodiments, the additional therapeutic agent is an antibody that specifically binds to a peptide-MHC complex. In certain embodiments, the additional therapeutic agent is an adjuvant. In one aspect, the present invention relates to (a) an antibody, polynucleotide, vector, recombinant host cell, and/or pharmaceutical composition of the present invention, as well as the use thereof for preparing medicines, and (b) a vaccine for use as a medicament, in particular, for use in a method for the treatment of cancer, preferably wherein the vaccine comprises a heat shock protein peptide complex (HSPPC) comprising a heat shock protein complexed with an antigenic peptide. In one aspect, the present invention relates to a pharmaceutical composition, kit or kit-of-parts comprising (a) an antibody, polynucleotide, vector, recombinant host cell, and/or pharmaceutical composition of the present invention and (b) a vaccine, preferably wherein the vaccine comprises a heat shock protein peptide complex (HSPPC) comprising a heat shock protein complexed with an antigenic peptide.

4. BRIEF DESCRIPTION OF THE DRAWINGS

Figure 1B:
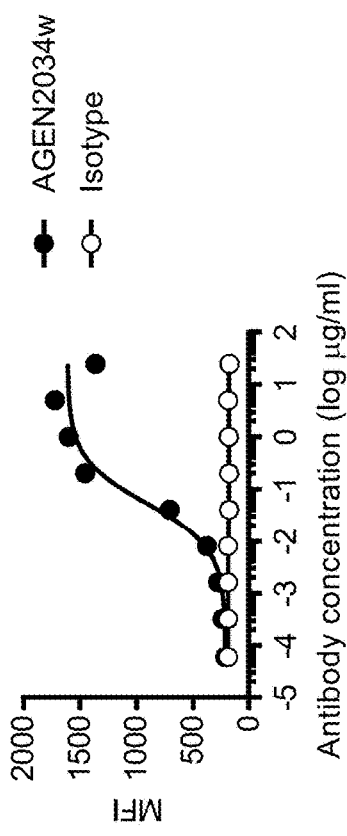
Figure 1C:
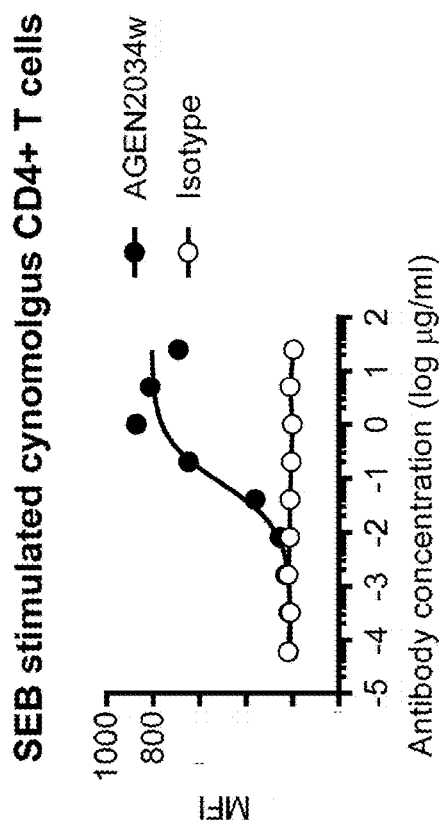

FIGS. 1A, 1B, 1C, and 1D are graphs showing the binding of anti-PD-1 antibodies to activated primary human or cynomolgus T cells as measured by flow cytometry. The mean fluorescence intensity (MFI) was calculated and plotted against a range of antibody concentrations. In FIG. 1A, AGEN2046w, AGEN2047w, and a human IgG$_1$ isotype control were measured for binding to Staphylococcus Enterotoxin A (SEA) stimulated human CD4+ T cells. AGEN2034w and a human IgG$_4$ isotype control were tested against SEA stimulated human CD4+ T cells (FIGS. 1B and 1D) and Staphylococcus Enterotoxin B (SEB) stimulated cynomolgus CD4+ T cells (FIG. 1C).

Figure 2:
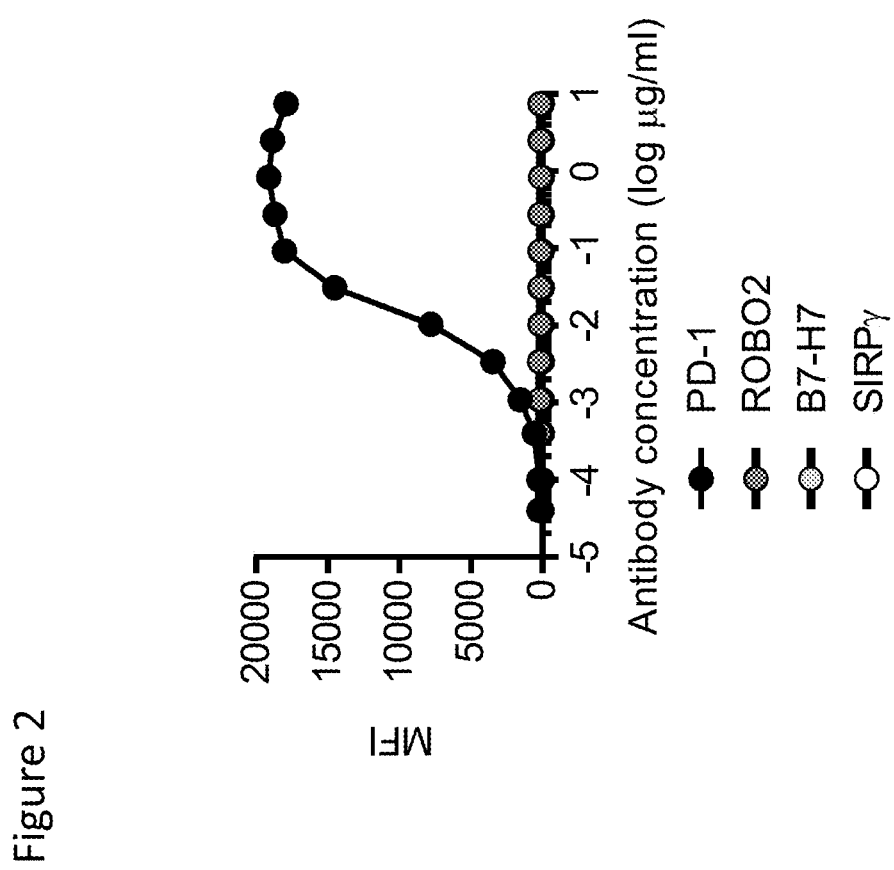

FIG. 2 is a graph showing the binding of AGEN2034w to human PD-1-Fc, human ROBO2-Fc, human B7-H7-Fc, or SIRPγ-His. The interaction was measured by suspension array technology and the median fluorescent intensity (MFI) is plotted against antibody concentrations.

Figure 3B:
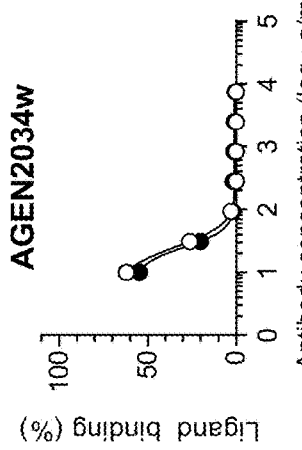
Figure 3D:
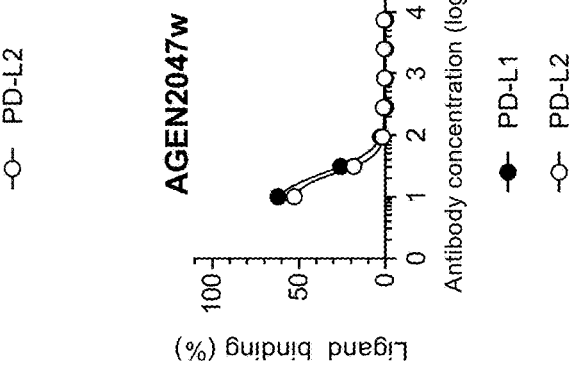
Figure 3A:
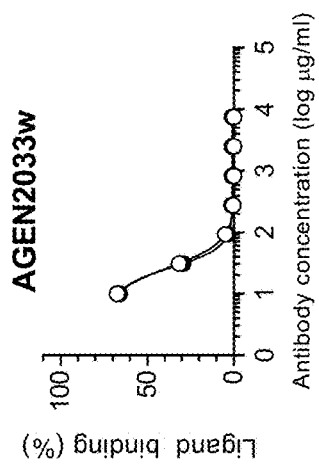
Figure 3C:
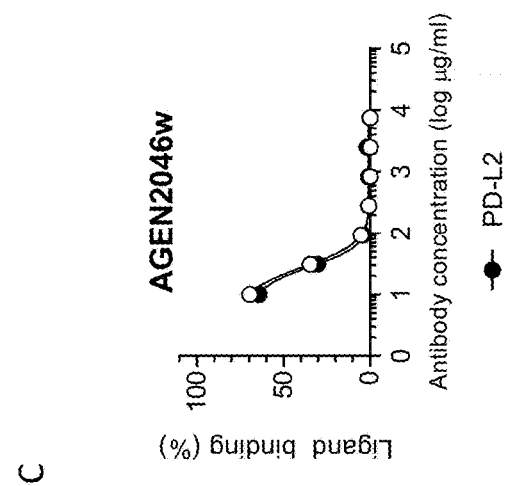
Figure 3E:
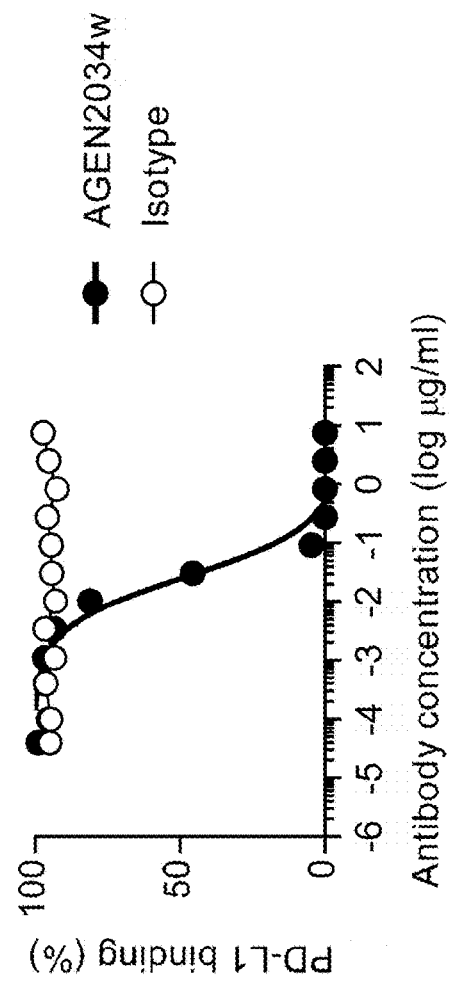
Figure 3F:
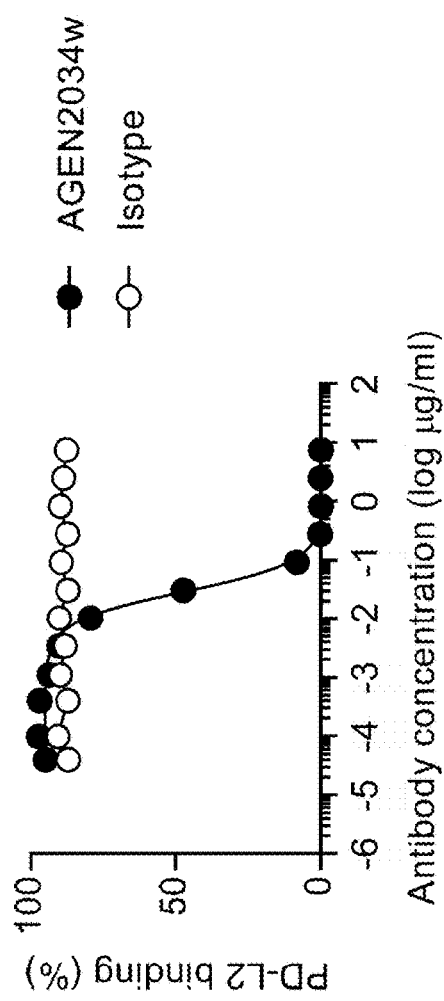

FIGS. 3A, 3B, 3C, 3D, 3E, and 3F are graphs showing the percent of recombinant PD-L1-Fc and/or PD-L2-Fc binding to PD-1 coupled beads in the presence of a dose titration of anti-PD-1 antibodies. In FIGS. 3A, 3B, 3C, and 3D, the anti-PD-1 antibodies tested are AGEN2033w, AGEN2034w, AGEN2046w, and AGEN2047w, respectively. In FIGS. 3E and 3F, similar results are shown for AGEN2034w and an isotype control antibody.

Figure 4B:
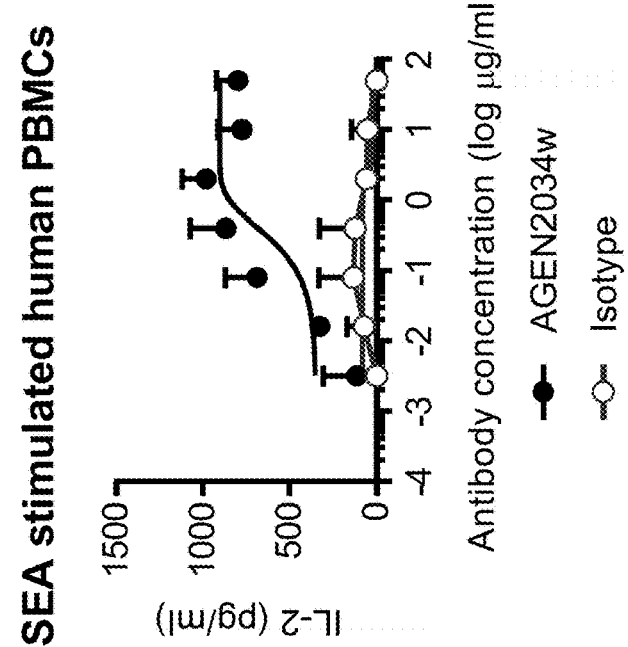
Figure 4A:
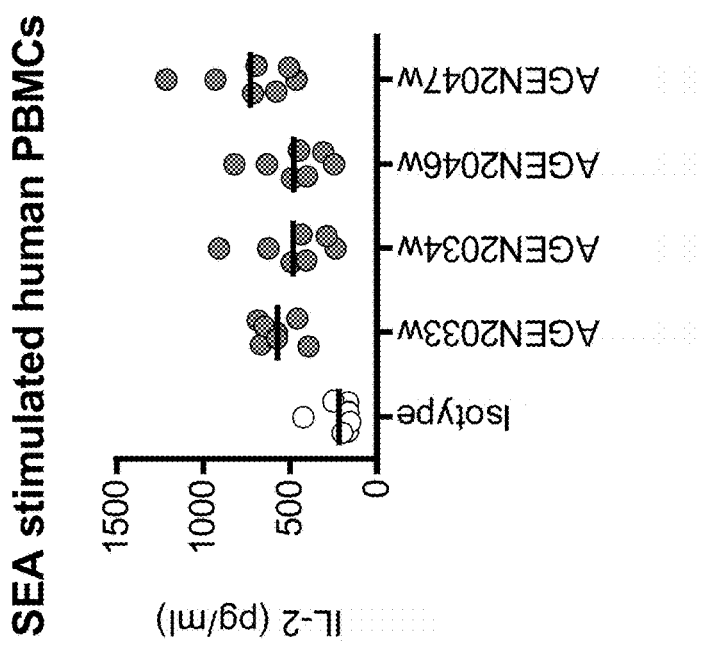
Figure 4C:
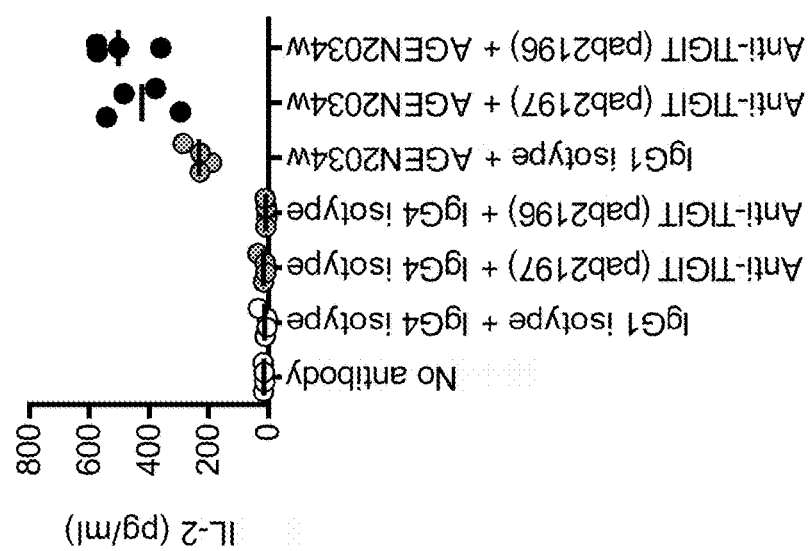
Figure 4D:
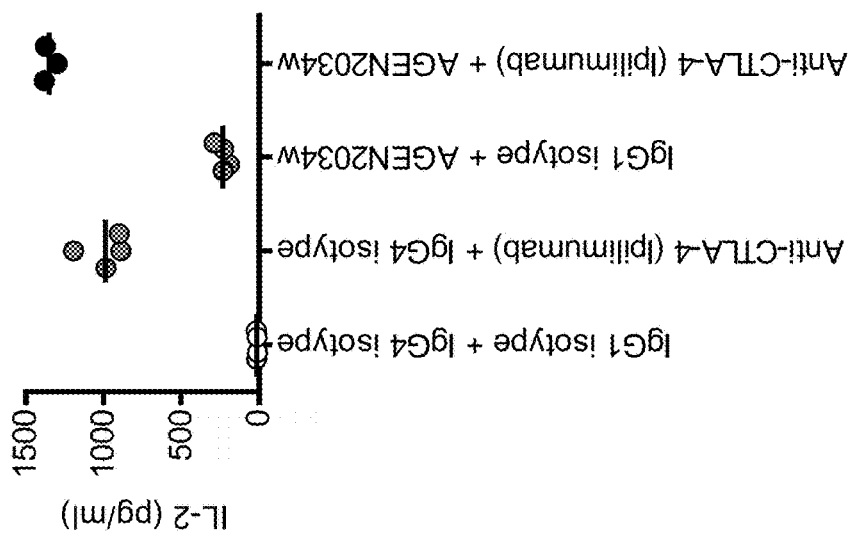
Figure 4F:
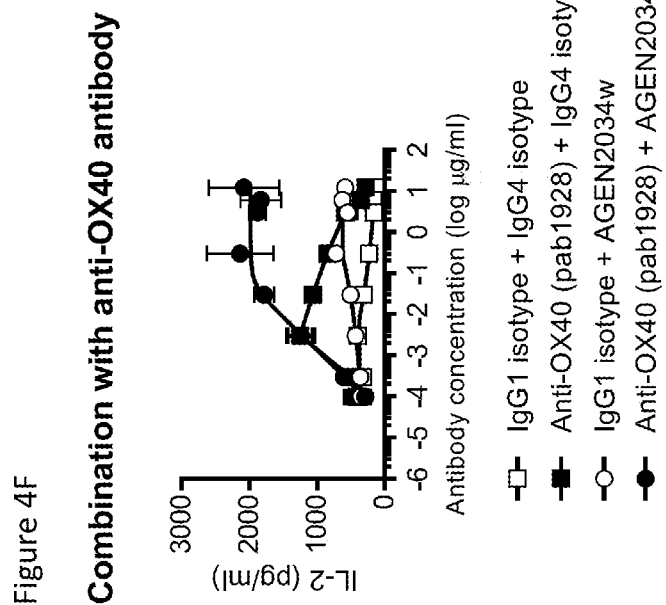
Figure 4E:
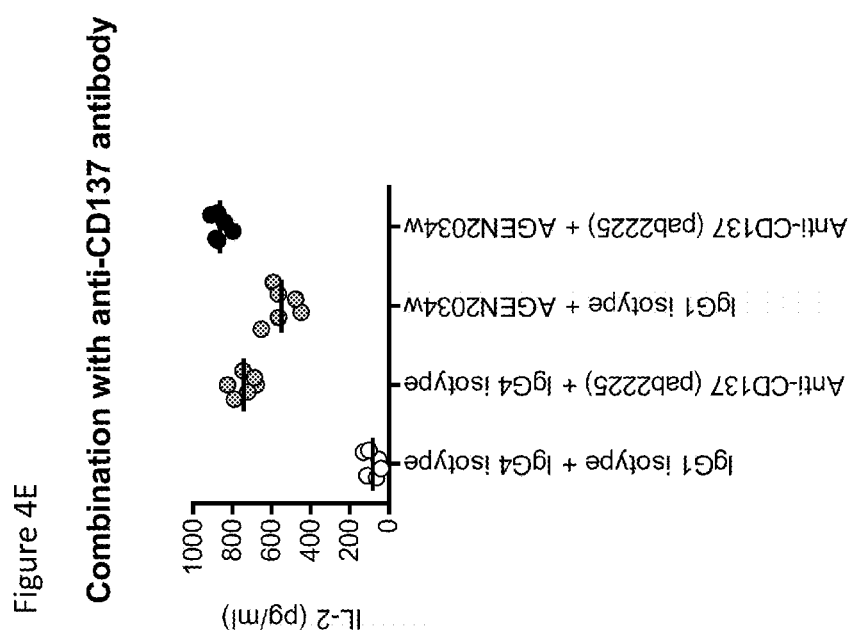

FIGS. 4A, 4B, 4C, 4D, 4E, and 4F are graphs depicting the functional activity of anti-PD-1 antibodies on cultures of primary human PBMCs following SEA stimulation. FIG. 4A is a graph showing IL-2 production induced by anti-PD-1 antibodies AGEN2033w, AGEN2034w, AGEN2046w, AGEN2047w, and an IgG$_1$ isotype control. The mean values (bar) of secreted IL-2 are shown. FIG. 4B is a graph showing IL-2 production in the presence of a dose titration of AGEN2034w as compared with an isotype control. Error bars represent one standard deviation. AGEN2034w or an isotype control antibody was tested in the presence or absence of anti-CTLA-4 antibody Ipilimumab (FIG. 4C), anti-TIGIT antibody pab2197 or pab2196 (FIG. 4D), anti-CD137 antibody pab2225 (FIG. 4E), or anti-OX40 antibody pab1928 (FIG. 4F).

Figure 5B:
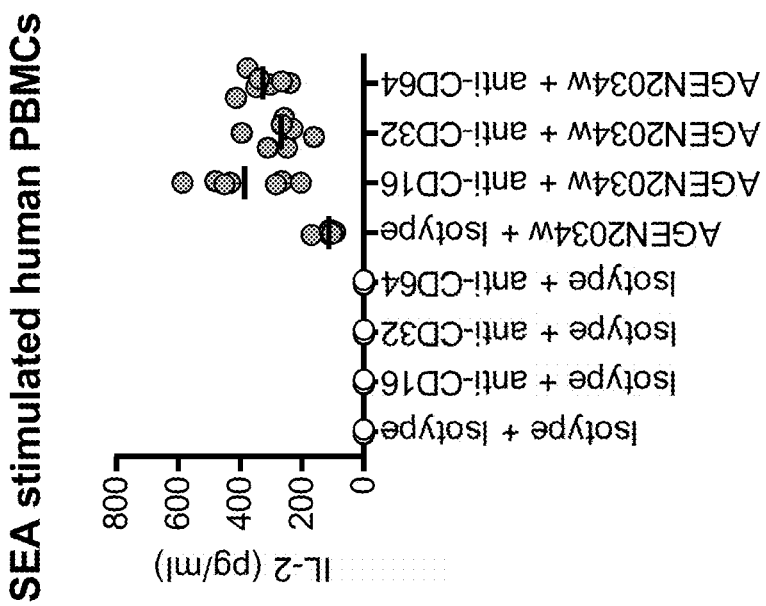
Figure 5A:
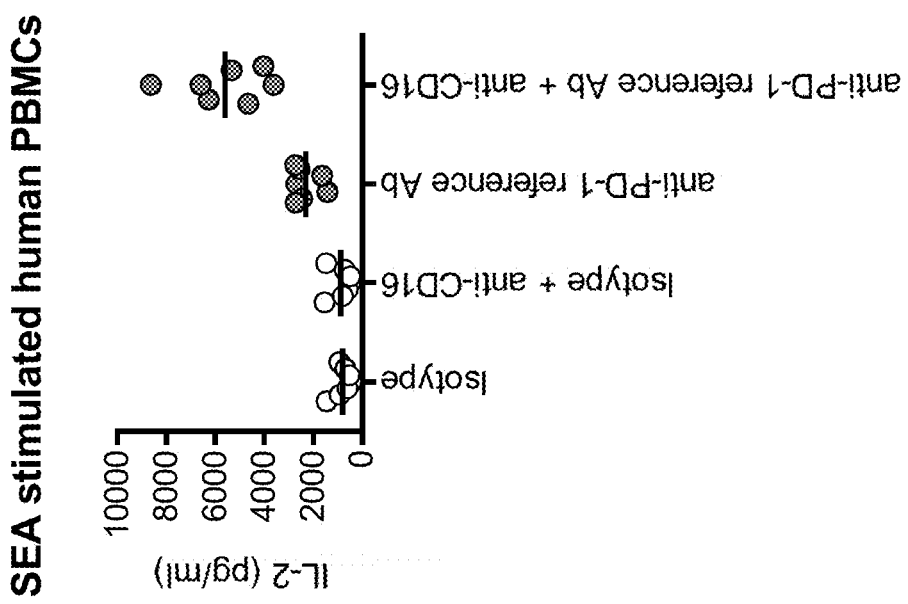
Figure 5C:
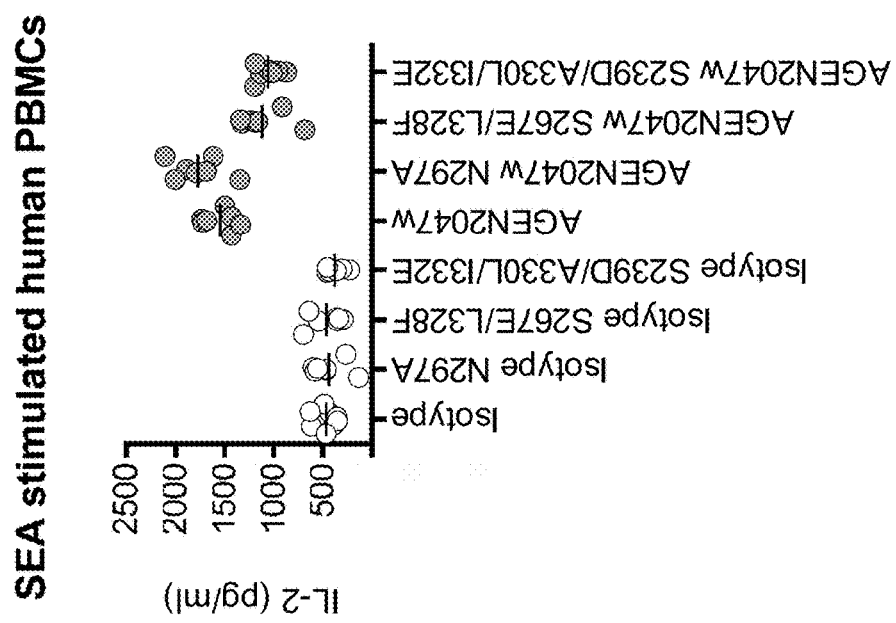

FIGS. 5A, 5B, and 5C are results from studies examining the impact of Fc gamma receptor (FcγR) engagement on the antagonistic activity of anti-PD-1 antibodies on primary human PBMCs following SEA stimulation. FIG. 5A is a graph showing IL-2 production induced by an anti-PD-1 reference antibody or an isotype control in the presence or absence of an anti-CD16 antibody. FIG. 5B is the result from a similar study examining IL-2 secretion induced by AGEN2034w or an isotype control in the presence of an isotype control, an anti-CD16 antibody, anti-CD32 antibody, or anti-CD64 antibody. FIG. 5C is a graph showing IL-2 production induced by AGEN2047w with wild type human IgG$_1$ Fc region, three corresponding Fc mutants (N297A, S267E/L328F, and S239D/A330L/I332E), and their respective isotype controls. The mean values (bar) of secreted IL-2 are shown.

Figure 6:
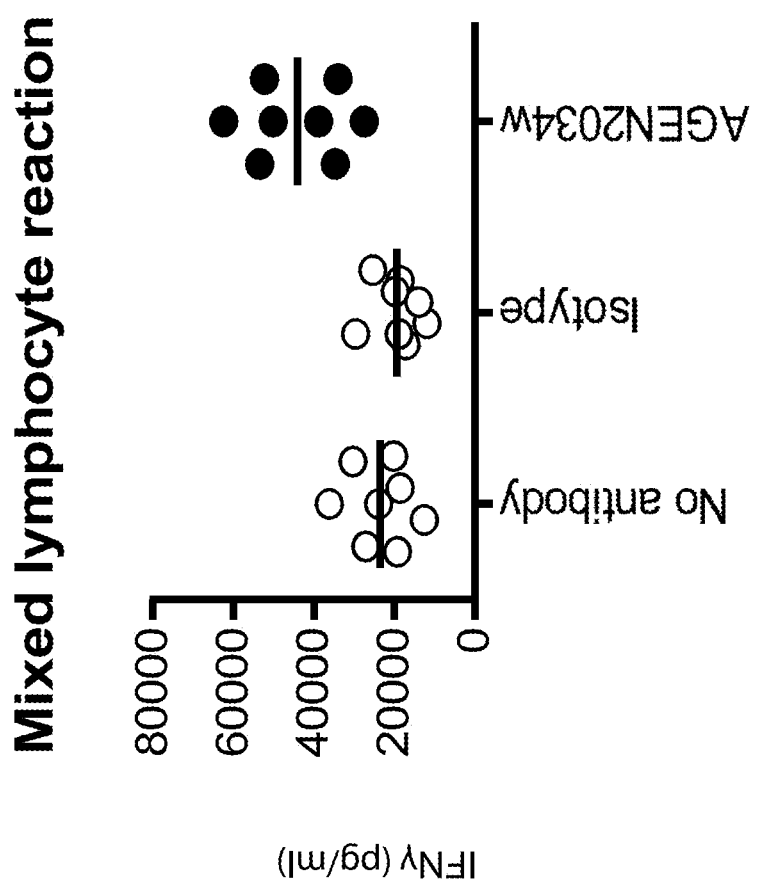

FIG. 6 is a graph showing IFNγ production of a co-culture of human T cells and allogenic dendritic cells in the absence of any antibody or in the presence of an isotype control antibody or the anti-PD-1 antibody AGEN2034w. The mean values (bar) of IFNγ are shown.

Figure 7A:
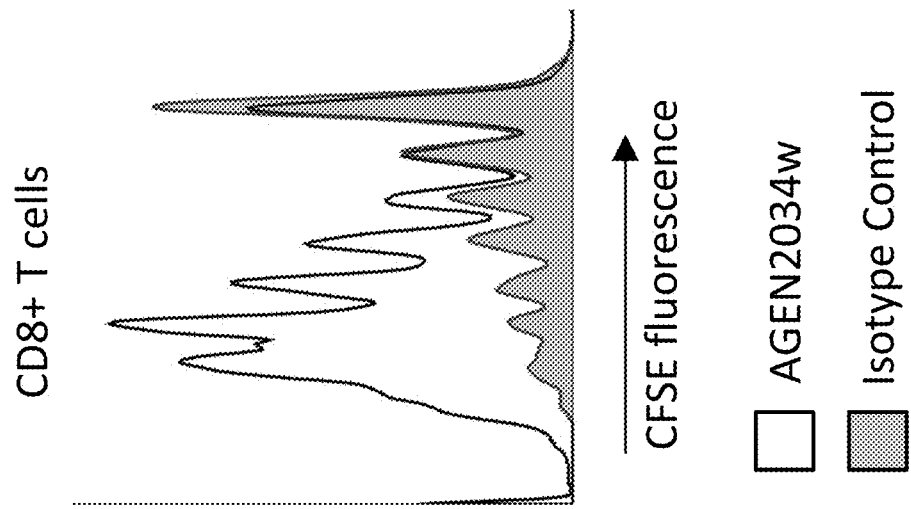
Figure 7B:
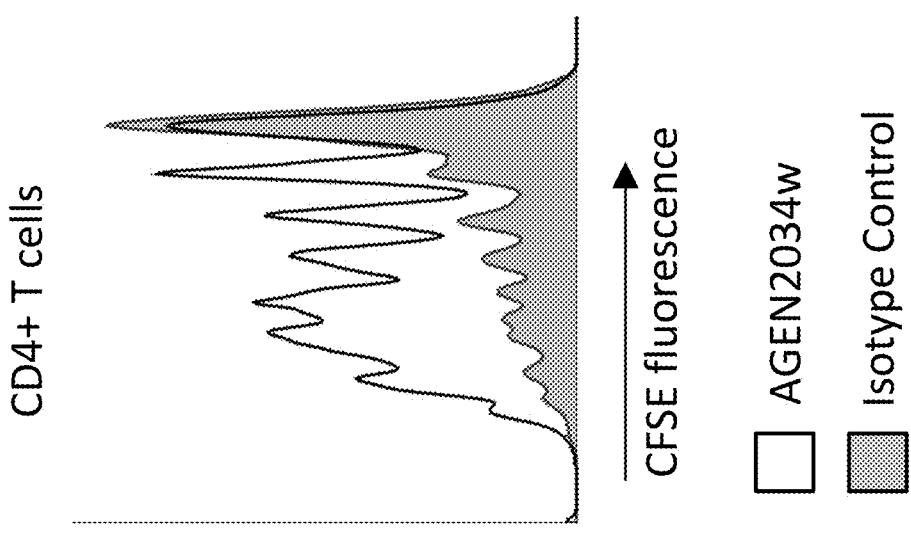
Figure 7C:
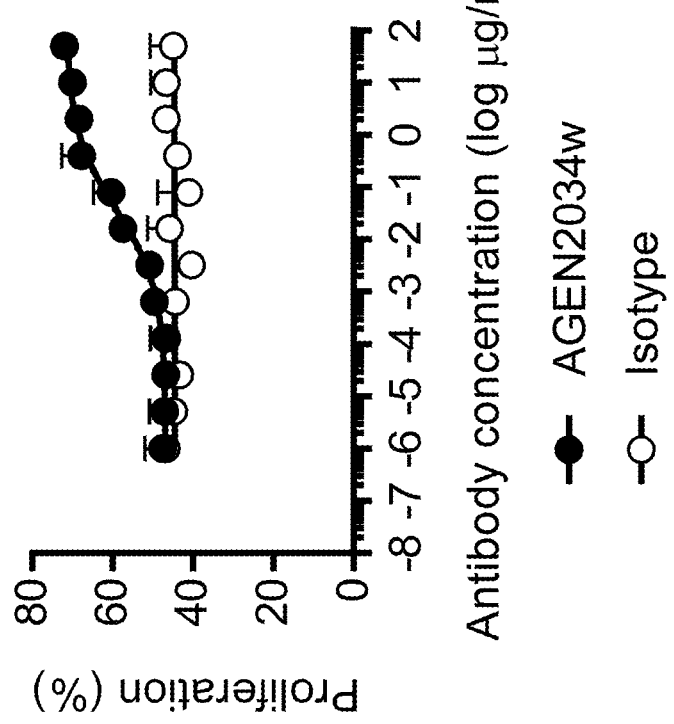

FIGS. 7A, 7B, and 7C are results from assays measuring proliferation of anti-CD3-antibody-stimulated T cells after co-culturing with ovarian cancer ascites fluid in the presence of AGEN2034w or an isotype control antibody. FIGS. 7A and 7B are representative histograms showing CFSE fluorescence from CD4+ and CD8+ T cells, respectively, in the presence of AGEN2034w or an isotype control antibody at 10 μg/ml. FIG. 7C is a graph showing results from a similar study. In FIG. 7C, proliferation of CD4+ T cells, as measured by CFSE dilution, was normalized to proliferation of CD4+ T cells in the absence of ovarian cancer ascites fluid and plotted against antibody concentrations.

Figure 8:
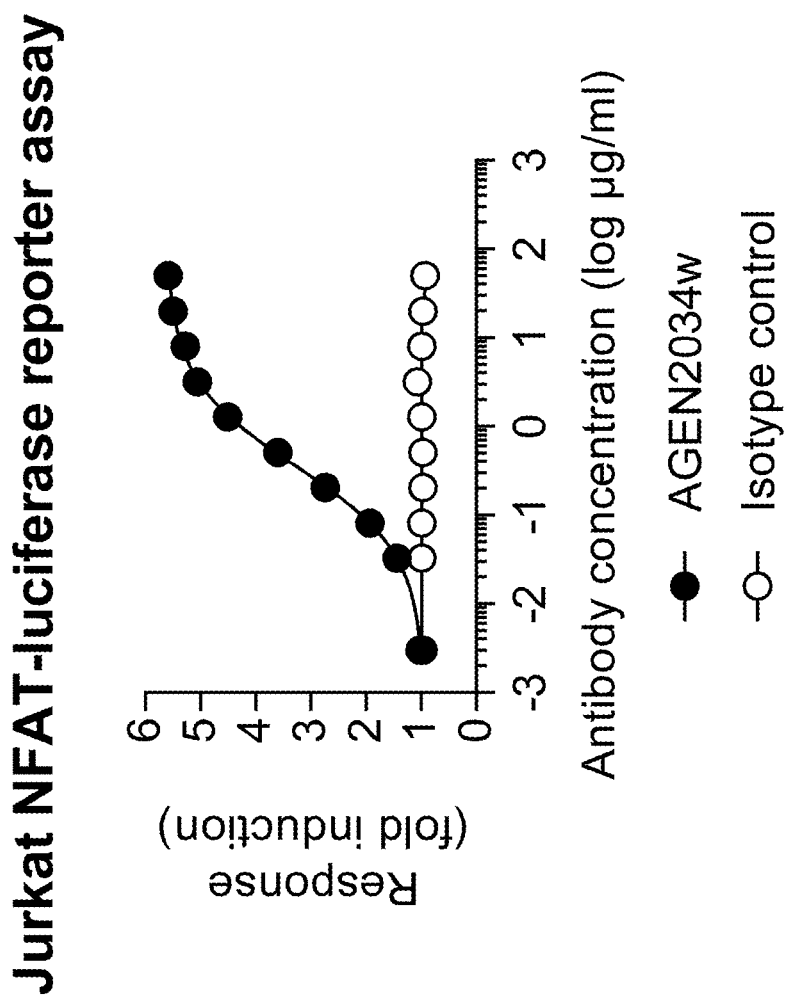

FIG. 8 is a graph showing response in a Jurkat NFAT-luciferase reporter assay induced by the anti-PD-1 antibody AGEN2034w or an IgG$_4$ isotype control antibody. Response, as measured by luciferase expression, was normalized to the response induced in the presence of the isotype control antibody at the lowest concentration tested (fold induction) and plotted against antibody concentrations.

Figure 9A:
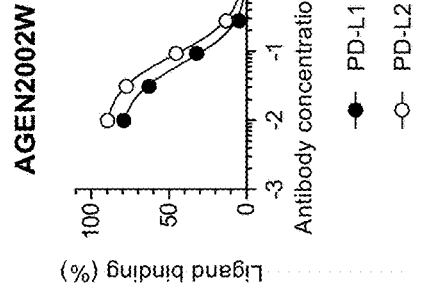
Figure 9B:
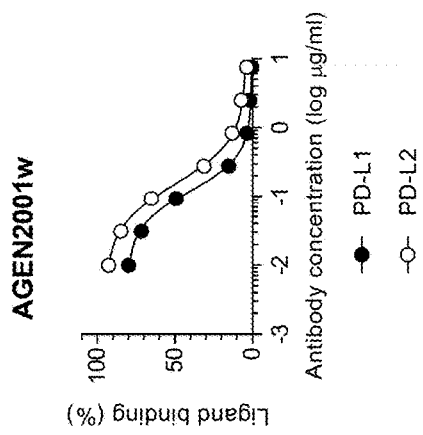
Figure 9C:
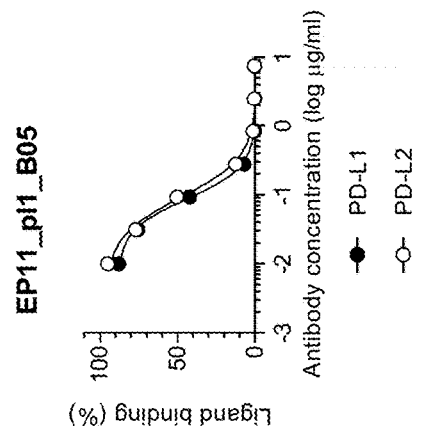
Figure 9D:
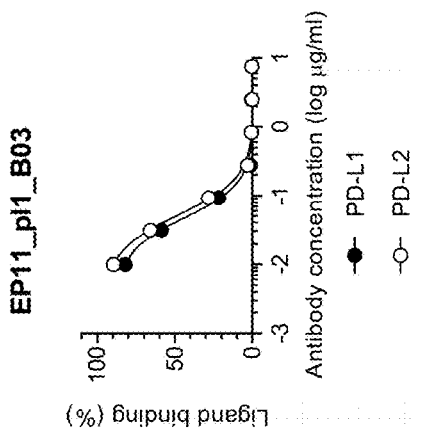
Figure 9F:
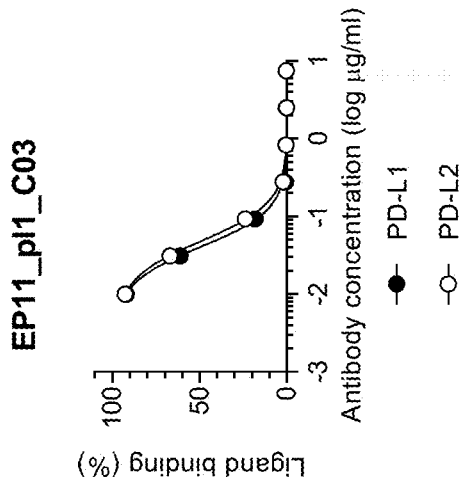
Figure 9E:
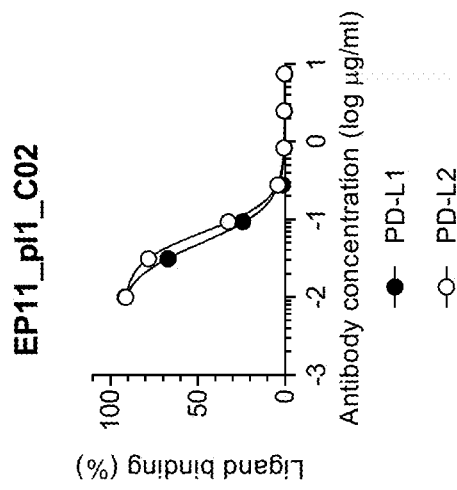

FIGS. 9A, 9B, 9C, 9D, 9E, and 9F are graphs showing the percent of recombinant PD-L1-Fc and PD-L2-Fc binding to PD-1 coupled beads in the presence of a dose titration of anti-PD-1 antibodies AGEN2001w (FIG. 9A), AGEN2002w (FIG. 9B), EP11_pl1_B03 (FIG. 9C), EP11_pl1_B05 (FIG. 9D), EP11_pl1_C02 (FIG. 9E), or EP11_pl1_C03 (FIG. 9F).

Figure 10:
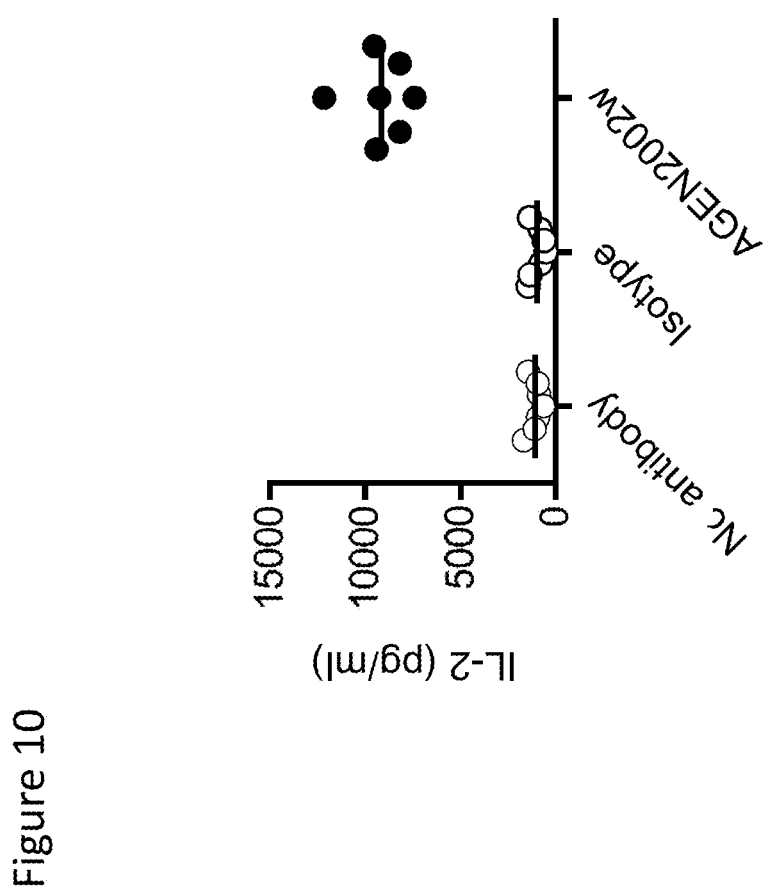

FIG. 10 is a graph depicting the functional activity of the anti-PD-1 antibody AGEN2002w or an IgG$_1$ isotype control on cultures of primary human PBMCs following SEA stimulation, as demonstrated by IL-2 production. The mean values (bar) of secreted IL-2 are shown.

5. DETAILED DESCRIPTION

The instant disclosure provides antibodies that specifically bind to human PD-1 and antagonize PD-1 function, e.g., PD-1-mediated immune suppression. Also provided are pharmaceutical compositions comprising these antibodies, nucleic acids encoding these antibodies, expression vectors and host cells for making these antibodies, and methods of treating a subject using these antibodies. The antibodies disclosed herein are particularly useful for increasing T cell activation in response to an antigen (e.g., a tumor antigen or an infectious disease antigen), and hence for treating cancer in a subject or treating or preventing an infectious disease in a subject. All instances of "isolated antibodies" described herein are additionally contemplated as antibodies that may be, but need not be, isolated. All instances of "isolated polynucleotides" described herein are additionally contemplated as polynucleotides that may be, but need not be, isolated. All instances of "antibodies" described herein are additionally contemplated as antibodies that may be, but need not be, isolated. All instances of "polynucleotides" described herein are additionally contemplated as polynucleotides that may be, but need not be, isolated.

5.1 Definitions

As used herein, the terms "about" and "approximately," when used to modify a numeric value or numeric range, indicate that deviations of up to 5% to 10% above and up to 5% to 10% below the value or range remain within the intended meaning of the recited value or range.

As used herein, the term "PD-1" refers to the protein programmed cell death protein 1. PD-1 nucleotide and amino acid sequences are well known in the art. An exemplary human PD-1 amino acid sequence is set forth in GenBank deposit GI: 167857792.

As used herein, the terms "antibody" and "antibodies" include full length antibodies, antigen-binding fragments of full length antibodies, and molecules comprising antibody CDRs, VH regions or VL regions. Examples of antibodies include monoclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single domain antibodies, monovalent antibodies, single chain antibodies or single-chain Fvs (scFv), camelized antibodies, affybodies, Fab fragments, F(ab')2 fragments, disulfide-linked Fvs (sdFv), anti-idiotypic (anti-Id) antibodies (including, e.g., anti-anti-Id antibodies), and antigen-binding fragments of any of the above. In certain embodiments, antibodies described herein refer to polyclonal antibody populations. Antibodies can be of any type (e.g., IgG, IgE, IgM, IgD, IgA or IgY), any class (e.g., IgG$_1$, IgG$_2$, IgG$_3$, IgG$_4$, IgA$_1$ or IgA$_2$), or any subclass (e.g., IgG$_{2a}$ or IgG$_{2b}$) of immunoglobulin molecule. In certain embodiments, antibodies described herein are IgG antibodies, or a class (e.g., human IgG$_1$ or IgG$_4$) or subclass thereof. In a specific embodiment, the antibody is a humanized monoclonal antibody. In another specific embodiment, the antibody is a human monoclonal antibody. In certain embodiments, an antibody described herein is an IgG$_1$ or IgG$_2$ antibody.

As used herein, the terms "VH region" and "VL region" refer to single antibody heavy and light chain variable regions, respectively, comprising FR (Framework Regions) 1, 2, 3 and 4 and CDR (Complementarity Determining Regions) 1, 2 and 3 (see Kabat et al., (1991) Sequences of Proteins of Immunological Interest (NIH Publication No. 91-3242, Bethesda), which is herein incorporated by reference in its entirety).

As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), by Chothia et al., J. Mol. Biol. 196:901-917 (1987), and by MacCallum et al., J. Mol. Biol. 262:732-745 (1996), all of which are herein incorporated by reference in their entireties, where the definitions include overlapping or subsets of amino acid residues when compared against each other. Preferably, the term "CDR" is a CDR as defined by Kabat, based on sequence comparisons. CDRH1, CDRH2 and CDRH3 denote the heavy chain CDRs, and CDRL1, CDRL2 and CDRL3 denote the light chain CDRs.

As used herein, the term "EU numbering system" refers to the EU numbering convention for the constant regions of an antibody, as described in Edelman, G. M. et al., Proc. Natl. Acad. USA, 63, 78-85 (1969) and Kabat et al., in "Sequences of Proteins of Immunological Interest", U.S. Dept. Health and Human Services, 5th edition, 1991, each of which is herein incorporated by reference in its entirety.

As used herein the term "framework (FR) amino acid residues" refers to those amino acids in the framework region of an immunoglobulin chain. The term "framework region" or "FR region" as used herein, includes the amino acid residues that are part of the variable region, but are not part of the CDRs (e.g., using the Kabat definition of CDRs).

As used herein, the terms "variable region" and "variable domain" are used interchangeably and are common in the art. The variable region typically refers to a portion of an antibody, generally, a portion of a light or heavy chain, typically about the amino-terminal 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

As used herein, the terms "constant region" and "constant domain" are interchangeable and are common in the art. The constant region is an antibody portion, e.g., a carboxyl terminal portion of a light and/or heavy chain which is not directly involved in binding of an antibody to antigen but which can exhibit various effector functions, such as interaction with an Fc receptor (e.g., Fc gamma receptor). The constant region of an immunoglobulin molecule generally has a more conserved amino acid sequence relative to an immunoglobulin variable domain.

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation rate constant of, e.g., an antibody to an antigen. The $k_{on}$ and $k_{off}$ can be determined by techniques known to one of ordinary skill in the art, such as BIAcore® or KinExA.

As used herein, the term "specifically binds to" refers to the ability of an antibody to bind to an antigen with a dissociation constant ($K_d$) of at least about $1\times10^{-6}$ M, $1\times10^{-7}$ M, $1\times10^{-8}$ M, $1\times10^{-9}$ M, $1\times10^{-10}$ M, $1\times10^{-11}$ M, $1\times10^{-12}$ M, or less, and/or bind to an antigen with an affinity that is at least two-fold greater than its affinity for a nonspecific antigen. In one embodiment, a molecule that specifically binds to an antigen can bind to other peptides or polypeptides, generally with lower affinity as determined by, e.g., immunoassays, BIAcore®, KinExA 3000 instrument (Sapidyne Instruments, Boise, Id.), or other assays known in the art. In one embodiment, a molecule that specifically binds to an antigen binds to the antigen with an association constant ($K_A$) that is at least 2 logs, 2.5 logs, 3 logs, 4 logs or greater than the $K_A$ when the molecule binds non-specifically to another antigen. In one embodiment, a molecule that specifically binds to an antigen binds to the antigen with a $K_d$ of $1\times10^{-6}$ M or less, $1\times10^{-7}$ M or less, $1\times10^{-8}$ M or less, $1\times10^{-9}$M or less, $1\times10^{-10}$ M or less, $1\times10^{-11}$ M or less, or $1\times10^{-12}$ M or less.

In another specific embodiment, molecules that specifically bind to an antigen do not cross react with other proteins under similar binding conditions. In another specific embodiment, molecules that specifically bind to PD-1 do not cross react with other non-PD-1 proteins. In a specific embodiment, provided herein is an antibody that binds to PD-1 (e.g., human PD-1) with higher affinity than to another unrelated antigen. In certain embodiments, provided herein is an antibody that binds to PD-1 (e.g., human PD-1) with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In a specific embodiment, the extent of binding of an anti-PD-1 antibody described herein to an unrelated, non-PD-1 protein is less than 10%, 15%, or 20% of the binding of the antibody to PD-1 protein as measured by, e.g., a radioimmunoassay.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays (e.g., constraining peptides using CLIPS (Chemical Linkage of Peptides onto Scaffolds) to map discontinuous or conformational epitopes), and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303, each of which is herein incorporated by reference in its entirety). Antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323, each of which is herein incorporated by reference in its entirety). Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085, each of which is herein incorporated by reference in its entirety, for a description of mutagenesis techniques, including alanine scanning mutagenesis techniques. CLIPS (Chemical Linkage of Peptides onto Scaffolds) is a technology to present one or more peptides in a structurally constrained configuration to behave as functional mimics of complex protein domains. See, e.g., U.S. Publication Nos. US 2008/0139407 A1 and US 2007/099240 A1, and U.S. Pat. No. 7,972,993, all of which are herein incorporated by reference in their entireties. In a specific embodiment, the epitope of an antibody is determined using alanine scanning mutagenesis studies. In a specific embodiment, the epitope of an antibody is determined using hydrogen/deuterium exchange coupled with mass spectrometry. In a specific embodiment, the epitope of an antibody is determined using CLIPS Epitope Mapping Technology from Pepscan Therapeutics.

As used herein, the terms "T cell receptor" and "TCR" are used interchangeably and refer to full length heterodimeric αβ or γδ TCRs, antigen-binding fragments of full length TCRs, and molecules comprising TCR CDRs or variable regions. Examples of TCRs include, but are not limited to, full length TCRs, antigen-binding fragments of full length TCRs, soluble TCRs lacking transmembrane and cytoplasmic regions, single-chain TCRs containing variable regions of TCRs attached by a flexible linker, TCR chains linked by an engineered disulfide bond, monospecific TCRs, multispecific TCRs (including bispecific TCRs), TCR fusions, human TCRs, humanized TCRs, chimeric TCRs, recombinantly produced TCRs, and synthetic TCRs. The term encompasses wild-type TCRs and genetically engineered TCRs (e.g., a chimeric TCR comprising a chimeric TCR chain which includes a first portion from a TCR of a first species and a second portion from a TCR of a second species).

As used herein, the terms "major histocompatibility complex" and "MHC" are used interchangeably and refer to an MHC class I molecule and/or an MHC class II molecule.

As used herein, the term "peptide-MHC complex" refers to an MHC molecule (MHC class I or MHC class II) with a peptide bound in the art-recognized peptide binding pocket of the MHC.

As used herein, the term "treat," "treating," and "treatment" refer to therapeutic or preventative measures described herein. The methods of "treatment" employ administration of an antibody to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "subject" includes any human or non-human animal. In a preferred embodiment, the subject is a human or non-human mammal, more preferably a human.

The determination of "percent identity" between two sequences (e.g., amino acid sequences or nucleic acid sequences) can be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877, each of which is herein incorporated by reference in its entirety. Such an algorithm is incorporated into the NBLAST and XBLAST programs of Altschul S F et al., (1990) J Mol Biol 215: 403, which is herein incorporated by reference in its entirety. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389-3402, which is herein incorporated by reference in its entirety. Alternatively, PSI BLAST can be used to perform an iterated search which detects distant relationships between molecules (Id.). When utilizing BLAST, Gapped BLAST, and PSI Blast programs, the default parameters of the respective programs (e.g., of) (BLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, 1988, CABIOS 4:11-17, which is herein incorporated by reference in its entirety. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

5.2 Anti-PD-1 Antibodies

In one aspect the instant disclosure provides antibodies that specifically bind to human PD-1 and antagonize PD-1 function. The amino acid sequences of exemplary antibodies are set forth in Tables 1-6, herein.

TABLE 1

Sequences of variable regions, CDRs, and FRs of exemplary anti-PD-1 antibodies

| SEQ ID NO: | Description | Amino acid Sequence |
|---|---|---|
| 1 | AGEN2033w Kabat CDRH1 | SYGMH |
| 2 | AGEN2033w Kabat CDRH2 | VIWYDGSNKYYADSVKG |
| 3 | AGEN2033w Kabat CDRH3 | NVDY |
| 4 | AGEN2033w Kabat CDRL1 | RASQSVSSNLA |
| 5 | AGEN2033w Kabat CDRL2 | GASTRAT |
| 6 | AGEN2033w Kabat CDRL3 | QQYNNWPRT |
| 7 | AGEN2034w Kabat CDRH3 | NGDH |
| 8 | AGEN2033w IMGT CDRH1 | GFTFSSYG |
| 9 | AGEN2033w IMGT CDRH2 | IWYDGSNK |
| 10 | AGEN2033w IMGT CDRH3 | ASNVDY |
| 11 | AGEN2033w IMGT CDRL1 | QSVSSN |
| 12 | AGEN2033w IMGT CDRL2 | GAS |
| 13 | AGEN2033w IMGT CDRL3 | QQYNNWPRT |
| 14 | AGEN2034w IMGT CDRH3 | ASNGDH |
| 15 | AGEN2033w, AGEN2046w VH | QVQLVESGGGVVQPGRSLRLSCAASGFTFSSYGMHWV RQAPGKGLEWVAVIWYDGSNKYYADSVKGRFTISRDN SKNTLYLQMNSLRAEDTAVYYCASNVDYWGQGTLVTV SS |
| 16 | AGEN2033w, AGEN2034w, AGEN2046w, AGEN2047w VL | EIVMTQSPATLSVSPGERATLSCRASQSVSSNLAWYQ QKPGQAPRLLIYGASTRATGIPARFSGSGSGTEFTLT ISSLQSEDFAVYYCQQYNNWPRTFGQGTKVEIK |
| 17 | AGEN2034w, AGEN2047w VH | QVQLVESGGGVVQPGRSLRLSCAASGFTFSSYGMHWV RQAPGKGLEWVAVIWYDGSNKYYADSVKGRFTISRDN SKNTLYLQMNSLRAEDTAVYYCASNGDHWGQGTLVTV SS |
| 18 | AGEN2033w heavy chain IgG4 S228P | QVQLVESGGGVVQPGRSLRLSCAASGFTFSSYGMHWV RQAPGKGLEWVAVIWYDGSNKYYADSVKGRFTISRDN SKNTLYLQMNSLRAEDTAVYYCASNVDYWGQGTLVTV SSASTKGPSVFPLAPCSRSTSESTAALGCLVKDYFPE PVTVSWNSGALTSGVHTFPAVLQSSGLYSLSSVVTVP SSSLGTKTYTCNVDHKPSNTKVDKRVESKYGPPCPPC PAPEFLGGPSVFLFPPKPKDTLMISRTPEVTCVVVDV SQEDPEVQFNWYVDGVEVHNAKTKPREEQFNSTYRVV SVLTVLHQDWLNGKEYKCKVSNKGLPSSIEKTISKAK GQPREPQVYTLPPSQEEMTKNQVSLTCLVKGFYPSDI AVEWESNGQPENNYKTTPPVLDSDGSFFLYSRLTVDK SRWQEGNVFSCSVMHEALHNHYTQKSLSLSLGK |
| 52 | AGEN2033w heavy chain IgG4 S228P (without C-terminal lysine) | QVQLVESGGGVVQPGRSLRLSCAASGFTFSSYGMHWV RQAPGKGLEWVAVIWYDGSNKYYADSVKGRFTISRDN SKNTLYLQMNSLRAEDTAVYYCASNVDYWGQGTLVTV SSASTKGPSVFPLAPCSRSTSESTAALGCLVKDYFPE PVTVSWNSGALTSGVHTFPAVLQSSGLYSLSSVVTVP |

TABLE 1-continued

Sequences of variable regions, CDRs, and FRs of exemplary anti-PD-1 antibodies

| SEQ ID NO | Description | Amino acid Sequence |
|---|---|---|
| | | SSSLGTKTYTCNVDHKPSNTKVDKRVESKYGPPCPPC PAPEFLGGPSVFLFPPKPKDTLMISRTPEVTCVVVDV SQEDPEVQFNWYVDGVEVHNAKTKPREEQFNSTYRVV SVLTVLHQDWLNGKEYKCKVSNKGLPSSIEKTISKAK GQPREPQVYTLPPSQEEMTKNQVSLTCLVKGFYPSDI AVEWESNGQPENNYKTTPPVLDSDGSFFLYSRLTVDK SRWQEGNVFSCSVMHEALHNHYTQKSLSLSLG |
| 19 | AGEN2033w, AGEN2034w, AGEN2046w, AGEN2047w light chain | EIVMTQSPATLSVSPGERATLSCRASQSVSSNLAWYQ QKPGQAPRLLIYGASTRATGIPARFSGSGSGTEFTLT ISSLQSEDFAVYYCQQYNNWPRTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| 20 | AGEN2034w heavy chain IgG4 S228P | QVQLVESGGGVVQPGRSLRLSCAASGFTFSSYGMHWV RQAPGKGLEWVAVIWYDGSNKYYADSVKGRFTISRDN SKNTLYLQMNSLRAEDTAVYYCASNGDHWGQGTLVTV SSASTKGPSVFPLAPCSRSTSESTAALGCLVKDYFPE PVTVSWNSGALTSGVHTFPAVLQSSGLYSLSSVVTVP SSSLGTKTYTCNVDHKPSNTKVDKRVESKYGPPCPPC PAPEFLGGPSVFLFPPKPKDTLMISRTPEVTCVVVDV SQEDPEVQFNWYVDGVEVHNAKTKPREEQFNSTYRVV SVLTVLHQDWLNGKEYKCKVSNKGLPSSIEKTISKAK GQPREPQVYTLPPSQEEMTKNQVSLTCLVKGFYPSDI AVEWESNGQPENNYKTTPPVLDSDGSFFLYSRLTVDK SRWQEGNVFSCSVMHEALHNHYTQKSLSLSLGK |
| 53 | AGEN2034w heavy chain IgG4 S228P (without C-terminal lysine) | QVQLVESGGGVVQPGRSLRLSCAASGFTFSSYGMHWV RQAPGKGLEWVAVIWYDGSNKYYADSVKGRFTISRDN SKNTLYLQMNSLRAEDTAVYYCASNGDHWGQGTLVTV SSASTKGPSVFPLAPCSRSTSESTAALGCLVKDYFPE PVTVSWNSGALTSGVHTFPAVLQSSGLYSLSSVVTVP SSSLGTKTYTCNVDHKPSNTKVDKRVESKYGPPCPPC PAPEFLGGPSVFLFPPKPKDTLMISRTPEVTCVVVDV SQEDPEVQFNWYVDGVEVHNAKTKPREEQFNSTYRVV SVLTVLHQDWLNGKEYKCKVSNKGLPSSIEKTISKAK GQPREPQVYTLPPSQEEMTKNQVSLTCLVKGFYPSDI AVEWESNGQPENNYKTTPPVLDSDGSFFLYSRLTVDK SRWQEGNVFSCSVMHEALHNHYTQKSLSLSLG |
| 21 | AGEN2046w heavy chain IgG1 | QVQLVESGGGVVQPGRSLRLSCAASGFTFSSYGMHWV RQAPGKGLEWVAVIWYDGSNKYYADSVKGRFTISRDN SKNTLYLQMNSLRAEDTAVYYCASNVDYWGQGTLVTV SSASTKGPSVFPLAPSSKSTSGGTAALGCLVKDYFPE PVTVSWNSGALTSGVHTFPAVLQSSGLYSLSSVVTVP SSSLGTQTYICNVNHKPSNTKVDKRVEPKSCDKTHTC PPCPAPELLGGPSVFLFPPKPKDTLMISRTPEVTCVV VDVSHEDPEVKFNWYVDGVEVHNAKTKPREEQYNSTY RVVSVLTVLHQDWLNGKEYKCKVSNKALPAPIEKTIS KAKGQPREPQVYTLPPSREEMTKNQVSLTCLVKGFYP SDIAVEWESNGQPENNYKTTPPVLDSDGSFFLYSKLT VDKSRWQQGNVFSCSVMHEALHNHYTQKSLSLSPGK |
| 54 | AGEN2046w heavy chain IgG1 (without C-terminal lysine) | QVQLVESGGGVVQPGRSLRLSCAASGFTFSSYGMHWV RQAPGKGLEWVAVIWYDGSNKYYADSVKGRFTISRDN SKNTLYLQMNSLRAEDTAVYYCASNVDYWGQGTLVTV SSASTKGPSVFPLAPSSKSTSGGTAALGCLVKDYFPE PVTVSWNSGALTSGVHTFPAVLQSSGLYSLSSVVTVP SSSLGTQTYICNVNHKPSNTKVDKRVEPKSCDKTHTC PPCPAPELLGGPSVFLFPPKPKDTLMISRTPEVTCVV VDVSHEDPEVKFNWYVDGVEVHNAKTKPREEQYNSTY RVVSVLTVLHQDWLNGKEYKCKVSNKALPAPIEKTIS KAKGQPREPQVYTLPPSREEMTKNQVSLTCLVKGFYP SDIAVEWESNGQPENNYKTTPPVLDSDGSFFLYSKLT VDKSRWQQGNVFSCSVMHEALHNHYTQKSLSLSPG |
| 22 | AGEN2047w heavy chain IgG1 | QVQLVESGGGVVQPGRSLRLSCAASGFTFSSYGMHWV RQAPGKGLEWVAVIWYDGSNKYYADSVKGRFTISRDN SKNTLYLQMNSLRAEDTAVYYCASNGDHWGQGTLVTV SSASTKGPSVFPLAPSSKSTSGGTAALGCLVKDYFPE PVTVSWNSGALTSGVHTFPAVLQSSGLYSLSSVVTVP SSSLGTQTYICNVNHKPSNTKVDKRVEPKSCDKTHTC PPCPAPELLGGPSVFLFPPKPKDTLMISRTPEVTCVV VDVSHEDPEVKFNWYVDGVEVHNAKTKPREEQYNSTY |

TABLE 1-continued

Sequences of variable regions, CDRs, and FRs of exemplary anti-PD-1 antibodies

| SEQ ID NO: | Description | Amino acid Sequence |
|---|---|---|
| | | RVVSVLTVLHQDWLNGKEYKCKVSNKALPAPIEKTIS<br>KAKGQPREPQVYTLPPSREEMTKNQVSLTCLVKGFYP<br>SDIAVEWESNGQPENNYKTTPPVLDSDGSFFLYSKLT<br>VDKSRWQQGNVFSCSVMHEALHNHYTQKSLSLSPGK |
| 55 | AGEN2047w heavy chain IgG1 (without C-terminal lysine) | QVQLVESGGGVVQPGRSLRLSCAASGFTFSSYGMHWV<br>RQAPGKGLEWVAVIWYDGSNKYYADSVKGRFTISRDN<br>SKNTLYLQMNSLRAEDTAVYYCASNGDHWGQGTLVTV<br>SSASTKGPSVFPLAPSSKSTSGGTAALGCLVKDYFPE<br>PVTVSWNSGALTSGVHTFPAVLQSSGLYSLSSVVTVP<br>SSSLGTQTYICNVNHKPSNTKVDKRVEPKSCDKTHTC<br>PPCPAPELLGGPSVFLFPPKPKDTLMISRTPEVTCVV<br>VDVSHEDPEVKFNWYVDGVEVHNAKTKPREEQYNSTY<br>RVVSVLTVLHQDWLNGKEYKCKVSNKALPAPIEKTIS<br>KAKGQPREPQVYTLPPSREEMTKNQVSLTCLVKGFYP<br>SDIAVEWESNGQPENNYKTTPPVLDSDGSFFLYSKLT<br>VDKSRWQQGNVFSCSVMHEALHNHYTQKSLSLSPG |
| 23 | AGEN2047w heavy chain IgG1 N297A | QVQLVESGGGVVQPGRSLRLSCAASGFTFSSYGMHWV<br>RQAPGKGLEWVAVIWYDGSNKYYADSVKGRFTISRDN<br>SKNTLYLQMNSLRAEDTAVYYCASNGDHWGQGTLVTV<br>SSASTKGPSVFPLAPSSKSTSGGTAALGCLVKDYFPE<br>PVTVSWNSGALTSGVHTFPAVLQSSGLYSLSSVVTVP<br>SSSLGTQTYICNVNHKPSNTKVDKRVEPKSCDKTHTC<br>PPCPAPELLGGPSVFLFPPKPKDTLMISRTPEVTCVV<br>VDVSHEDPEVKFNWYVDGVEVHNAKTKPREEQYASTY<br>RVVSVLTVLHQDWLNGKEYKCKVSNKALPAPIEKTIS<br>KAKGQPREPQVYTLPPSREEMTKNQVSLTCLVKGFYP<br>SDIAVEWESNGQPENNYKTTPPVLDSDGSFFLYSKLT<br>VDKSRWQQGNVFSCSVMHEALHNHYTQKSLSLSPGK |
| 56 | AGEN2047w heavy chain IgG1 N297A (without C-terminal lysine) | QVQLVESGGGVVQPGRSLRLSCAASGFTFSSYGMHWV<br>RQAPGKGLEWVAVIWYDGSNKYYADSVKGRFTISRDN<br>SKNTLYLQMNSLRAEDTAVYYCASNGDHWGQGTLVTV<br>SSASTKGPSVFPLAPSSKSTSGGTAALGCLVKDYFPE<br>PVTVSWNSGALTSGVHTFPAVLQSSGLYSLSSVVTVP<br>SSSLGTQTYICNVNHKPSNTKVDKRVEPKSCDKTHTC<br>PPCPAPELLGGPSVFLFPPKPKDTLMISRTPEVTCVV<br>VDVSHEDPEVKFNWYVDGVEVHNAKTKPREEQYASTY<br>RVVSVLTVLHQDWLNGKEYKCKVSNKALPAPIEKTIS<br>KAKGQPREPQVYTLPPSREEMTKNQVSLTCLVKGFYP<br>SDIAVEWESNGQPENNYKTTPPVLDSDGSFFLYSKLT<br>VDKSRWQQGNVFSCSVMHEALHNHYTQKSLSLSPG |
| 24 | AGEN2047w heavy chain IgG1 S267E/L328F | QVQLVESGGGVVQPGRSLRLSCAASGFTFSSYGMHWV<br>RQAPGKGLEWVAVIWYDGSNKYYADSVKGRFTISRDN<br>SKNTLYLQMNSLRAEDTAVYYCASNGDHWGQGTLVTV<br>SSASTKGPSVFPLAPSSKSTSGGTAALGCLVKDYFPE<br>PVTVSWNSGALTSGVHTFPAVLQSSGLYSLSSVVTVP<br>SSSLGTQTYICNVNHKPSNTKVDKRVEPKSCDKTHTC<br>PPCPAPELLGGPSVFLFPPKPKDTLMISRTPEVTCVV<br>VDVEHEDPEVKFNWYVDGVEVHNAKTKPREEQYNSTY<br>RVVSVLTVLHQDWLNGKEYKCKVSNKAFPAPIEKTIS<br>KAKGQPREPQVYTLPPSREEMTKNQVSLTCLVKGFYP<br>SDIAVEWESNGQPENNYKTTPPVLDSDGSFFLYSKLT<br>VDKSRWQQGNVFSCSVMHEALHNHYTQKSLSLSPGK |
| 57 | AGEN2047w heavy chain IgG1 S267E/L328F (without C-terminal lysine) | QVQLVESGGGVVQPGRSLRLSCAASGFTFSSYGMHWV<br>RQAPGKGLEWVAVIWYDGSNKYYADSVKGRFTISRDN<br>SKNTLYLQMNSLRAEDTAVYYCASNGDHWGQGTLVTV<br>SSASTKGPSVFPLAPSSKSTSGGTAALGCLVKDYFPE<br>PVTVSWNSGALTSGVHTFPAVLQSSGLYSLSSVVTVP<br>SSSLGTQTYICNVNHKPSNTKVDKRVEPKSCDKTHTC<br>PPCPAPELLGGPSVFLFPPKPKDTLMISRTPEVTCVV<br>VDVEHEDPEVKFNWYVDGVEVHNAKTKPREEQYNSTY<br>RVVSVLTVLHQDWLNGKEYKCKVSNKAFPAPIEKTIS<br>KAKGQPREPQVYTLPPSREEMTKNQVSLTCLVKGFYP<br>SDIAVEWESNGQPENNYKTTPPVLDSDGSFFLYSKLT<br>VDKSRWQQGNVFSCSVMHEALHNHYTQKSLSLSPG |
| 25 | AGEN2047w heavy chain IgG1 S239D/A330L/I332E | QVQLVESGGGVVQPGRSLRLSCAASGFTFSSYGMHWV<br>RQAPGKGLEWVAVIWYDGSNKYYADSVKGRFTISRDN<br>SKNTLYLQMNSLRAEDTAVYYCASNGDHWGQGTLVTV<br>SSASTKGPSVFPLAPSSKSTSGGTAALGCLVKDYFPE<br>PVTVSWNSGALTSGVHTFPAVLQSSGLYSLSSVVTVP |

TABLE 1-continued

Sequences of variable regions, CDRs, and FRs of exemplary anti-PD-1 antibodies

| SEQ ID NO: | Description | Amino acid Sequence |
|---|---|---|
| | | SSSLGTQTYICNVNHKPSNTKVDKRVEPKSCDKTHTC PPCPAPELLGGPDVFLFPPKPKDTLMISRTPEVTCVV VDVSHEDPEVKFNWYVDGVEVHNAKTKPREEQYNSTY RVVSVLTVLHQDWLNGKEYKCKVSNKALPLPEEKTIS KAKGQPREPQVYTLPPSREEMTKNQVSLTCLVKGFYP SDIAVEWESNGQPENNYKTTPPVLDSDGSFFLYSKLT VDKSRWQQGNVFSCSVMHEALHNHYTQKSLSLSPGK |
| 58 | AGEN2047w heavy chain IgG1 S239D/A330L/I332E (without C-terminal lysine) | QVQLVESGGGVVQPGRSLRLSCAASGFTFSSYGMHWV RQAPGKGLEWVAVIWYDGSNKYYADSVKGRFTISRDN SKNTLYLQMNSLRAEDTAVYYCASNGDHWGQGTLVTV SSASTKGPSVFPLAPSSKSTSGGTAALGCLVKDYFPE PVTVSWNSGALTSGVHTFPAVLQSSGLYSLSSVVTVP SSSLGTQTYICNVNHKPSNTKVDKRVEPKSCDKTHTC PPCPAPELLGGPDVFLFPPKPKDTLMISRTPEVTCVV VDVSHEDPEVKFNWYVDGVEVHNAKTKPREEQYNSTY RVVSVLTVLHQDWLNGKEYKCKVSNKALPLPEEKTIS KAKGQPREPQVYTLPPSREEMTKNQVSLTCLVKGFYP SDIAVEWESNGQPENNYKTTPPVLDSDGSFFLYSKLT VDKSRWQQGNVFSCSVMHEALHNHYTQKSLSLSPG |
| 26 | AGEN2001w VH (BADD426-2614) | QVQLVESGGGVVQPGRSLRLSCAASGFTFSSYGMHWV RQAPGKGLEWVAVIWYDGSNKYYADSVKGRFTISRDN SKNTLYLQMNSLRAEDTAVYYCATNGDYWGQGTLVTV SS |
| 27 | AGEN2002w VH (BADD426-2615) | QVQLVESGGGVVQPGRSLRLSCAASGFTFSSYGMHWV RQAPGKGLEWVAVIWYDGSNKYYADSVKGRFTISRDN SKNTLYLQMNSLRAEDTAVYYCASNGDYWGQGTLVTV SS |
| 28 | EP11_p11_B03 (BADD438-2743) | QVQLVESGGGVVQPGRSLRLSCAASGFTFSSYGMHWV RQAPGKGLEWVAVIWYDGSNEYYADSVKGRFTISRDN SKNTLYLQMNSLRAEDTAVYYCASNGDHWGQGTLVTV SS |
| 29 | EP11_p11_B05 (BADD438-2745) | QVQLVESGGGMVQPGRSLRLSCAASGFTFSSYGMHWV RQAPGKGLEWVAVIWFDGSNKYYADSVKGRFTISRDN SKNTLYLQMNSLRAEDTAVYYCASNGDHWGQGTLVTV SS |
| 30 | EP11_p11_C02 (BADD438-2746) | QVQLVESGGGVVQPGRSLRLSCAASGFTFSSYGMHWV RQAPGKGLEWVAVIWYDGSNKYYADSVKGRFTISRDN SKNTLYLQMNSLRAEDTAVYYCASNGDHWGHGTLVTV SS |
| 31 | EP11_p11_C03 (BADD438-2747) | QVQLVESGGGVVQPGRSLRLSCAASGFTFSSYGMHWV RQAPGKGLEWVAVIWYDGSNKYYADSVMGRFTISRDN SKNTLYLQMNSLRAEDTAVYYCASNGDHWGQGTLVTV SS |
| 32 | CDRH2 consensus | VIWX$_1$DGSNX$_2$YYADSVX$_3$G<br>X$_1$ is Y or F;<br>X$_2$ is K or E; and<br>X$_3$ is K or M |
| 33 | CDRH3 consensus | NX$_1$DX$_2$<br>X1 is G or V; and<br>X2 is H or Y |
| 34 | CDRH2 | VIWYDGSNEYYADSVKG |
| 35 | CDRH2 | VIWFDGSNKYYADSVKG |
| 36 | CDRH2 | VIWYDGSNKYYADSVMG |
| 37 | CDRH3 | NGDY |
| 38 | VH FR1 | QVQLVESGGGVVQPGRSLRLSCAASGFTFS |
| 39 | VH FR1 | QVQLVESGGGMVQPGRSLRLSCAASGFTFS |
| 40 | VH FR2 | WVRQAPGKGLEWVA |
| 41 | VH FR3 | RFTISRDNSKNTLYLQMNSLRAEDTAVYYCAS |

US 10,450,373 B2

TABLE 1-continued

Sequences of variable regions, CDRs, and FRs of exemplary anti-PD-1 antibodies

| SEQ ID NO: | Description | Amino acid Sequence |
|---|---|---|
| 42 | VH FR3 | RFTISRDNSKNTLYLQMNSLRAEDTAVYYCAT |
| 43 | VH FR4 | WGQGTLVTVSS |
| 44 | VH FR4 | WGHGTLVTVSS |
| 45 | VL FR1 | EIVMTQSPATLSVSPGERATLSC |
| 46 | VL FR2 | WYQQKPGQAPRLLTY |
| 47 | VL FR3 | GIPARFSGSGSGTEFTLTISSLQSEDFAVYYC |
| 48 | VL FR4 | FGQGTKVEIK |
| 49 | VH consensus sequence | QVQLVESGGGX$_1$VQPGRSLRLSCAASGFTFSSYGMHW VRQAPGKGLEWVAVIWX$_2$DGSNX$_3$YYADSVX$_4$GRFTIS RDNSKNTLYLQMNSLRAEDTAVYYCAX$_5$NX$_6$DX$_7$WGX$_8$ GTLVTVSS<br>X$_1$ is V or M,<br>X$_2$ is Y or F,<br>X$_3$ is K or E,<br>X$_4$ is K or M,<br>X$_5$ is S or T,<br>X$_6$ is G or V,<br>X$_7$ is H or Y, and<br>X$_8$ is Q or H |
| 50 | IGHV3-33*01 germline sequence | QVQLVESGGGVVQPGRSLRLSCAASGFTFSSYGMHW RQAPGKGLEWVAVIWYDGSNKYYADSVKGRFTISRDN SKNTLYLQMNSLRAEDTAVYYCAR |
| 51 | IGKV3-15*01 germline sequence | EIVMTQSPATLSVSPGERATLSCRASQSVSSNLAWYQ QKPGQAPRLLIYGASTRATGIPARFSGSGSGTEFTLT ISSLQSEDFAVYYCQQYNNWP |
| 59 | Human IgG1 G1m3 allotype (without C-terminal lysine) | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKRVEPKSCDKTHTCPP CPAPELLGGPSVFLFPPKPKDTLMISRTPEVTCVVVD VSHEDPEVKFNWYVDGVEVHNAKTKPREEQYNSTYRV VSVLTVLHQDWLNGKEYKCKVSNKALPAPIEKTISKA KGQPREPQVYTLPPSREEMTKNQVSLTCLVKGFYPSD IAVEWESNGQPENNYKTTPPVLDSDGSFFLYSKLTVD KSRWQQGNVFSCSVMHEALHNHYTQKSLSLSPG |
| 60 | Human IgG1 G1m3 allotype | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKRVEPKSCDKTHTCPP CPAPELLGGPSVFLFPPKPKDTLMISRTPEVTCVVVD VSHEDPEVKFNWYVDGVEVHNAKTKPREEQYNSTYRV VSVLTVLHQDWLNGKEYKCKVSNKALPAPIEKTISKA KGQPREPQVYTLPPSREEMTKNQVSLTCLVKGFYPSD IAVEWESNGQPENNYKTTPPVLDSDGSFFLYSKLTVD KSRWQQGNVFSCSVMHEALHNHYTQKSLSLSPGK |
| 61 | IgG1 N297A (without C-terminal lysine) | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKRVEPKSCDKTHTCPP CPAPELLGGPSVFLFPPKPKDTLMISRTPEVTCVVVD VSHEDPEVKFNWYVDGVEVHNAKTKPREEQYASTYRV VSVLTVLHQDWLNGKEYKCKVSNKALPAPIEKTISKA KGQPREPQVYTLPPSREEMTKNQVSLTCLVKGFYPSD IAVEWESNGQPENNYKTTPPVLDSDGSFFLYSKLTVD KSRWQQGNVFSCSVMHEALHNHYTQKSLSLSPG |
| 62 | IgG1 N297A | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKRVEPKSCDKTHTCPP CPAPELLGGPSVFLFPPKPKDTLMISRTPEVTCVVVD VSHEDPEVKFNWYVDGVEVHNAKTKPREEQYASTYRV VSVLTVLHQDWLNGKEYKCKVSNKALPAPIEKTISKA KGQPREPQVYTLPPSREEMTKNQVSLTCLVKGFYPSD IAVEWESNGQPENNYKTTPPVLDSDGSFFLYSKLTVD KSRWQQGNVFSCSVMHEALHNHYTQKSLSLSPGK |

TABLE 1-continued

Sequences of variable regions, CDRs, and FRs of exemplary anti-PD-1 antibodies

| SEQ ID NO: | Description | Amino acid Sequence |
|---|---|---|
| 63 | IgG4 S228P (without C-terminal lysine) | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG |
| 64 | IgG4 S228P | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 65 | Human kappa light chain constant region IGKC*01 Km3 allotype | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 2

Heavy chain CDR sequences of exemplary anti-PD-1 antibodies[1]

| Antibody | CDRH1 (SEQ ID NO:) | CDRH2 (SEQ ID NO:) | CDRH3 (SEQ ID NO:) |
|---|---|---|---|
| AGEN2033w | SYGMH (1) | VIWYDGSNKYYADSVKG (2) | NVDY (3) |
| AGEN2034w | SYGMH (1) | VIWYDGSNKYYADSVKG (2) | NGDH (7) |
| AGEN2001w | SYGMH (1) | VIWYDGSNKYYADSVKG (2) | NGDY (37) |
| AGEN2002w | SYGMH (1) | VIWYDGSNKYYADSVKG (2) | NGDY (37) |
| EP11_p11_B03 | SYGMH (1) | VIWYDGSNEYYADSVKG (34) | NGDH (7) |
| EP11_p11_B05 | SYGMH (1) | VIWFDGSNKYYADSVKG (35) | NGDH (7) |
| EP11_p11_C02 | SYGMH (1) | VIWYDGSNKYYADSVKG (2) | NGDH (7) |
| EP11_p11_C03 | SYGMH (1) | VIWYDGSNKYYADSVMG (36) | NGDH (7) |

[1]The VH CDRs in Table 2 are determined according to Kabat.

TABLE 3

Light chain CDR sequences of exemplary anti-PD-1 antibodies[2]

| Antibody | CDRL1 (SEQ ID NO:) | CDRL2 (SEQ ID NO:) | CDRL3 (SEQ ID NO:) |
|---|---|---|---|
| AGEN2033w | RASQSVSSNLA (4) | GASTRAT (5) | QQYNNWPRT (6) |
| AGEN2034w | RASQSVSSNLA (4) | GASTRAT (5) | QQYNNWPRT (6) |
| AGEN2001w | RASQSVSSNLA (4) | GASTRAT (5) | QQYNNWPRT (6) |
| AGEN2002w | RASQSVSSNLA (4) | GASTRAT (5) | QQYNNWPRT (6) |
| EP11_p11_B03 | RASQSVSSNLA (4) | GASTRAT (5) | QQYNNWPRT (6) |
| EP11_p11_B05 | RASQSVSSNLA (4) | GASTRAT (5) | QQYNNWPRT (6) |

TABLE 3-continued

Light chain CDR sequences of exemplary anti-PD-1 antibodies[2]

| Antibody | CDRL1 (SEQ ID NO:) | CDRL2 (SEQ ID NO:) | CDRL3 (SEQ ID NO:) |
|---|---|---|---|
| EP11_p11_C02 | RASQSVSSNLA (4) | GASTRAT (5) | QQYNNWPRT (6) |
| EP11_p11_C03 | RASQSVSSNLA (4) | GASTRAT (5) | QQYNNWPRT (6) |

[2]The VL CDRs in Table 3 are determined according to Kabat.

TABLE 4

VH framework (FR) sequences of exemplary anti-PD-1 antibodies[3]

| Antibody | VH FR1 (SEQ ID NO:) | VH FR2 (SEQ ID NO:) | VH FR3 (SEQ ID NO:) | VH FR4 (SEQ ID NO:) |
|---|---|---|---|---|
| AGEN2033w | QVQLVESGGGVVQPGRSLRLSCAASGFTFS (38) | WVRQAPGKGLEWVA (40) | RFTISRDNSKNTLYLQMNSLRAEDTAVYYCAS (41) | WGQGTLVTVSS (43) |
| AGEN2034w | QVQLVESGGGVVQPGRSLRLSCAASGFTFS (38) | WVRQAPGKGLEWVA (40) | RFTISRDNSKNTLYLQMNSLRAEDTAVYYCAS (41) | WGQGTLVTVSS (43) |
| AGEN2001w | QVQLVESGGGVVQPGRSLRLSCAASGFTFS (38) | WVRQAPGKGLEWVA (40) | RFTISRDNSKNTLYLQMNSLRAEDTAVYYCAT (42) | WGQGTLVTVSS (43) |
| AGEN2002w | QVQLVESGGGVVQPGRSLRLSCAASGFTFS (38) | WVRQAPGKGLEWVA (40) | RFTISRDNSKNTLYLQMNSLRAEDTAVYYCAS (41) | WGQGTLVTVSS (43) |
| EP11_p11_B03 | QVQLVESGGGVVQPGRSLRLSCAASGFTFS (38) | WVRQAPGKGLEWVA (40) | RFTISRDNSKNTLYLQMNSLRAEDTAVYYCAS (41) | WGQGTLVTVSS (43) |
| EP11_p11_B05 | QVQLVESGGGMVQPGRSLRLSCAASGFTFS (39) | WVRQAPGKGLEWVA (40) | RFTISRDNSKNTLYLQMNSLRAEDTAVYYCAS (41) | WGQGTLVTVSS (43) |
| EP11_p11_C02 | QVQLVESGGGVVQPGRSLRLSCAASGFTFS (38) | WVRQAPGKGLEWVA (40) | RFTISRDNSKNTLYLQMNSLRAEDTAVYYCAS (41) | WGHGTLVTVSS (44) |
| EP11_p11_C03 | QVQLVESGGGVVQPGRSLRLSCAASGFTFS (38) | WVRQAPGKGLEWVA (40) | RFTISRDNSKNTLYLQMNSLRAEDTAVYYCAS (41) | WGQGTLVTVSS (43) |

[3]The VH framework regions described in Table 4 are determined based upon the boundaries of the Kabat numbering system for CDRs. In other words, the VH CDRs are determined by Kabat and the framework regions are the amino acid residues surrounding the CDRs in the variable region in the format FR1, CDRH1, FR2, CDRH2, FR3, CDRH3, and FR4.

TABLE 5

VL framework (FR) sequences of exemplary anti-PD-1 antibodies[4]

| Antibody | VL FR1 (SEQ ID NO:) | VL FR2 (SEQ ID NO:) | VL FR3 (SEQ ID NO:) | VL FR4 (SEQ ID NO:) |
|---|---|---|---|---|
| AGEN2033w | EIVMTQSPATLSVSPGERATLSC (45) | WYQQKPGQAPRLLIY (46) | GIPARFSGSGSGTEFTLTISSLQSEDFAVYYC (47) | FGQGTKVEIK (48) |
| AGEN2034w | EIVMTQSPATLSVSPGERATLSC (45) | WYQQKPGQAPRLLIY (46) | GIPARFSGSGSGTEFTLTISSLQSEDFAVYYC (47) | FGQGTKVEIK (48) |
| AGEN2001w | EIVMTQSPATLSVSPGERATLSC (45) | WYQQKPGQAPRLLIY (46) | GIPARFSGSGSGTEFTLTISSLQSEDFAVYYC (47) | FGQGTKVEIK (48) |
| AGEN2002w | EIVMTQSPATLSVSPGERATLSC (45) | WYQQKPGQAPRLLIY (46) | GIPARFSGSGSGTEFTLTISSLQSEDFAVYYC (47) | FGQGTKVEIK (48) |
| EP11_p11_B03 | EIVMTQSPATLSVSPGERATLSC (45) | WYQQKPGQAPRLLIY (46) | GIPARFSGSGSGTEFTLTISSLQSEDFAVYYC (47) | FGQGTKVEIK (48) |
| EP11_p11_B05 | EIVMTQSPATLSVSPGERATLSC (45) | WYQQKPGQAPRLLIY (46) | GIPARFSGSGSGTEFTLTISSLQSEDFAVYYC (47) | FGQGTKVEIK (48) |

TABLE 5-continued

VL framework (FR) sequences of exemplary anti-PD-1 antibodies[4]

| Antibody | VL FR1 (SEQ ID NO:) | VL FR2 (SEQ ID NO:) | VL FR3 (SEQ ID NO:) | VL FR4 (SEQ ID NO:) |
|---|---|---|---|---|
| EP11_pl1_C02 | EIVMTQSPATLSVS PGERATLSC (45) | WYQQKPGQAPRLLIY (46) | GIPARFSGSGSGTEFTLT ISSLQSEDFAVYYC (47) | FGQGTKVEIK (48) |
| EP11_pl1_C03 | EIVMTQSPATLSVS PGERATLSC (45) | WYQQKPGQAPRLLIY (46) | GIPARFSGSGSGTEFTLT ISSLQSEDFAVYYC (47) | FGQGTKVEIK (48) |

[4]The VL framework regions described in Table 5 are determined based upon the boundaries of the Kabat numbering system for CDRs. In other words, the VL CDRs are determined by Kabat and the framework regions are the amino acid residues surrounding the CDRs in the variable region in the format FR1, CDRL1, FR2, CDRL2, FR3, CDRL3, and FR4.

TABLE 6

VH and VL sequences of exemplary anti-PD-1 antibodies

| Antibody | Heavy chain variable region | SEQ ID NO: | Light chain variable region | SEQ ID NO: |
|---|---|---|---|---|
| AGEN2033w | BADD438-2742 | 15 | 3738 | 16 |
| AGEN2034w | BADD438-2744 | 17 | 3738 | 16 |
| AGEN2001w | BADD426-2614 | 26 | 3738 | 16 |
| AGEN2002w | BADD426-2615 | 27 | 3738 | 16 |
| EP11_pl1_B03 | BADD438-2743 | 28 | 3738 | 16 |
| EP11_pl1_B05 | BADD438-2745 | 29 | 3738 | 16 |
| EP11_pl1_C02 | BADD438-2746 | 30 | 3738 | 16 |
| EP11_pl1_C03 | BADD438-2747 | 31 | 3738 | 16 |

TABLE 7

Exemplary sequences of PD-1

| SEQ ID NO: | Description | Amino acid Sequence |
|---|---|---|
| 74 | Exemplary mature PD-1 sequence | PGWFLDSPDRPWNPPTFSPALLVVTEGDNATFTCSFSNTS ESFVLNWYRMSPSNQTDKLAAFPEDRSQPGQDCRFRVTQL PNGRDFHMSVVRARRNDSGTYLCGAISLAPKAQIKESLRA ELRVTERRAEVPTAHPSPSPRPAGQFQTLVVGVVGGLLGS LVLLVWVLAVICSRAARGTIGARRTGQPLKEDPSAVPVFS VDYGELDFQWREKTPEPPVPCVPEQTEYATIVFPSGMGTS SPARRGSADGPRSAQPLRPEDGHCSWPL |
| 75 | PD-1 epitope (residues 107-122) | SLAPKAQIKESLRAEL |
| 76 | PD-1 epitope (residues 5-22) | LDSPDRPWNPPTFSPALL |
| 77 | PD-1 epitope (residues 6-15) | DSPDRPWNPP |
| 78 | PD-1 epitope (residues 130-138) | EVPTAHPSP |
| 79 | PD-1 epitope (residues 106-113) | ISLAPKAQ |

In certain embodiments, the instant disclosure provides an isolated antibody that specifically binds to human PD-1, comprising:
(a) CDRH1 comprises the amino acid sequence of SYGMH (SEQ ID NO: 1); and/or
(b) CDRH2 comprises the amino acid sequence of VIWX$_1$DGSNX$_2$YYADSVX$_3$G (SEQ ID NO: 32), wherein
X$_1$ is Y or F;
X$_2$ is K or E; and
X$_3$ is K or M; and/or
(c) CDRH3 comprises the amino acid sequence of NX$_1$DX$_2$ (SEQ ID NO: 33), wherein
X$_1$ is G or V; and
X$_2$ is H or Y; and/or
(d) CDRL1 comprises the amino acid sequence of RASQS-VSSNLA (SEQ ID NO: 4); and/or
(e) CDRL2 comprises the amino acid sequence of GAS-TRAT (SEQ ID NO: 5); and/or
(f) CDRL3 comprises the amino acid sequence of QQYN-NWPRT (SEQ ID NO: 6).

In certain embodiments, the antibody comprises one, two, or all three of the VH CDRs above. In certain embodiments, the antibody comprises the CDRH1 of one of the antibodies in Table 2. In certain embodiments, the antibody comprises the CDRH2 of one of the antibodies in Table 2. In certain embodiments, the antibody comprises the CDRH3 of one of the antibodies in Table 2. In certain embodiments, the antibody comprises one, two, or all three of VH CDRs of one of the antibodies in Table 2 (e.g., the VH CDRs in one row of Table 2, for example, all of the VH CDRs from AGEN2033w or AGEN2034w). In certain embodiments, the antibody comprises the VH frameworks described herein. In certain embodiments, the antibody comprises the VH framework regions of an antibody set forth in Table 4 (e.g., one, two, three, or four of the framework regions in one row of Table 4).

In certain embodiments, the antibody comprises one, two, or all three of the VL CDRs above. In certain embodiments, the antibody comprises the CDRL1 of one of the antibodies in Table 3. In certain embodiments, the antibody comprises the CDRL2 of one of the antibodies in Table 3. In certain embodiments, the antibody comprises the CDRL3 of one of the antibodies in Table 3. In certain embodiments, the antibody comprises one, two, or all three of the VL CDRs of one of the antibodies in Table 3 (e.g., the VL CDRs in one row of Table 3, for example, all of the VL CDRs from AGEN2033w or AGEN2034w). In certain embodiments, the antibody comprises the VL framework regions described herein. In certain embodiments, the antibody comprises the VL framework regions (FRs) of an antibody set forth in Table 5 (e.g., one, two, three, or four of the framework regions in one row of Table 5).

In certain embodiments, the instant disclosure provides an isolated antibody that specifically binds to human PD-1, comprising a heavy chain variable region comprising complementarity determining regions CDRH1, CDRH2 and CDRH3 and a light chain variable region comprising complementarity determining regions CDRL1, CDRL2 and CDRL3, wherein:
(a) CDRH1 comprises the amino acid sequence of SYGMH (SEQ ID NO: 1);
(b) CDRH2 comprises the amino acid sequence of VIWX$_1$DGSNX$_2$YYADSVX$_3$G (SEQ ID NO: 32), wherein
X$_1$ is Y or F;
X$_2$ is K or E; and
X$_3$ is K or M;
(c) CDRH3 comprises the amino acid sequence of NX$_1$DX$_2$ (SEQ ID NO: 33), wherein
X$_1$ is G or V; and
X$_2$ is H or Y;
(d) CDRL1 comprises the amino acid sequence of RASQSVSSNLA (SEQ ID NO: 4);
(e) CDRL2 comprises the amino acid sequence of GASTRAT (SEQ ID NO: 5); and
(f) CDRL3 comprises the amino acid sequence of QQYNNWPRT (SEQ ID NO: 6).

In certain embodiments, the CDRH2 comprises an amino acid sequence selected from the group consisting of SEQ ID NOs: 2 and 34-36. In certain embodiments, the CDRH3 comprises an amino acid sequence selected from the group consisting of SEQ ID NOs: 3, 7, and 37.

In certain embodiments, the instant disclosure provides an isolated antibody that specifically binds to human PD-1, comprising a heavy chain variable region comprising complementarity determining regions CDRH1, CDRH2 and CDRH3, wherein the CDRH1, CDRH2 and CDRH3 comprise the CDRH1, CDRH2 and CDRH3 amino acid sequences, respectively, set forth in SEQ ID NOs: 1, 2, and 3; 1, 2, and 7; 1, 2, and 37; 1, 34, and 7; 1, 35, and 7; or 1, 36, and 7.

In certain embodiments, the instant disclosure provides an isolated antibody that specifically binds to human PD-1, comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2 and CDRL3 comprise the CDRH1, CDRH2, CDRH3, CDRL1, CDRL2 and CDRL3 amino acid sequences, respectively, set forth in SEQ ID NOs: 1, 2, 3, 4, 5, and 6; 1, 2, 7, 4, 5, and 6; 1, 2, 37, 4, 5, and 6; 1, 34, 7, 4, 5, and 6; 1, 35, 7, 4, 5, and 6; or 1, 36, 7, 4, 5, and 6, respectively.

In certain embodiments, the instant disclosure provides an isolated antibody that specifically binds to human PD-1, comprising:
(a) a CDRH1 comprising the amino acid sequence of SYGMH (SEQ ID NO: 1); and/or
(b) a CDRH2 comprising the amino acid sequence of VIWYDGSNKYYADSVKG (SEQ ID NO: 2); and/or
(c) a CDRH3 comprising the amino acid sequence of NVDY (SEQ ID NO: 3) or NGDH (SEQ ID NO: 7); and/or
(d) a CDRL1 comprising the amino acid sequence of RASQSVSSNLA (SEQ ID NO: 4); and/or
(e) a CDRL2 comprising the amino acid sequence of GASTRAT (SEQ ID NO: 5); and/or
(f) a CDRL3 comprising the amino acid sequence of QQYNNWPRT (SEQ ID NO: 6).

In certain embodiments, the antibody comprises one, two, or all three of the VH CDRs set forth in SEQ ID NOs: 1, 2, and 3. In certain embodiments, the antibody comprises one, two, or all three of the VH CDRs set forth in SEQ ID NOs: 1, 2, and 7. In certain embodiments, the antibody comprises one, two, or all three of the VL CDRs set forth in SEQ ID NOs: 4, 5, and 6.

In certain embodiments, the instant disclosure provides an isolated antibody that specifically binds to human PD-1, comprising a heavy chain variable region comprising complementarity determining regions CDRH1, CDRH2 and CDRH3, wherein the CDRH1, CDRH2 and CDRH3 comprise the CDRH1, CDRH2 and CDRH3 amino acid sequences set forth in SEQ ID NOs: 1, 2, and 3, respectively.

In certain embodiments, the instant disclosure provides an isolated antibody that specifically binds to human PD-1, comprising a heavy chain variable region comprising complementarity determining regions CDRH1, CDRH2 and CDRH3, wherein the CDRH1, CDRH2 and CDRH3 comprise the CDRH1, CDRH2 and CDRH3 amino acid sequences set forth in SEQ ID NOs: 1, 2, and 7, respectively.

In certain embodiments, the instant disclosure provides an isolated antibody that specifically binds to human PD-1, comprising a light chain variable region comprising complementarity determining regions CDRL1, CDRL2 and CDRL3, wherein the CDRL1, CDRL2 and CDRL3 comprise the CDRL1, CDRL2 and CDRL3 amino acid sequences set forth in SEQ ID NOs: 4, 5, and 6, respectively.

In certain embodiments, the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 1, 2, 3, 4, 5, and 6, respectively.

In certain embodiments, the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 1, 2, 7, 4, 5, and 6, respectively.

In certain embodiments, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226, all of which are herein incorporated by reference in their entireties). Typically, when using the Kabat numbering convention, the Chothia CDRH1 loop is present at heavy chain amino acids 26 to 32, 33, or 34, the Chothia CDRH2 loop is present at heavy chain amino acids 52 to 56, and the Chothia CDRH3 loop is present at heavy chain amino acids 95 to 102, while the Chothia CDRL1 loop is present at light chain amino acids 24 to 34, the Chothia CDRL2 loop is present at light chain amino acids 50 to 56, and the Chothia CDRL3 loop is present at light chain amino acids 89 to 97. The end of the Chothia CDRH1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain embodiments, the instant disclosure provides an isolated antibody that specifically binds to human PD-1, the antibody comprising the Chothia VL CDRs of a VL of an antibody disclosed in Table 6 herein (e.g., AGEN2033w or AGEN2034w). In certain embodiments, the instant disclosure provides an isolated antibody that specifically binds to human PD-1, the antibody comprising the Chothia VH CDRs of an antibody disclosed in Table 6 herein (e.g., AGEN2033w or AGEN2034w). In certain embodiments, the instant disclosure provides an isolated antibody that specifically binds to human PD-1, the antibody comprising the Chothia VH CDRs and Chothia VL CDRs of an antibody disclosed in Table 6 herein (e.g., AGEN2033w or AGEN2034w). In certain embodiments, antibodies that specifically bind to human PD-1 comprise one or more CDRs, in which the Chothia and Kabat CDRs have the same amino acid sequence. In certain embodiments, the instant disclosure provides an isolated antibody that specifically binds to human PD-1 and comprises combinations of Kabat CDRs and Chothia CDRs.

In certain embodiments, the CDRs of an antibody can be determined according to the IMGT numbering system as described in Lefranc M-P, (1999) The Immunologist 7: 132-136 and Lefranc M-P et al., (1999) Nucleic Acids Res 27: 209-212, each of which is herein incorporated by reference in its entirety. According to the IMGT numbering scheme, CDRH1 is at positions 26 to 35, CDRH2 is at positions 51 to 57, CDRH3 is at positions 93 to 102, CDRL1 is at positions 27 to 32, CDRL2 is at positions 50 to 52, and CDRL3 is at positions 89 to 97. In a particular embodiment, the instant disclosure provides antibodies that specifically bind to human PD-1 and comprise CDRs of an antibody disclosed in Table 6 herein (e.g., AGEN2033w or AGEN2034w) as determined by the IMGT numbering system, for example, as described in Lefranc M-P (1999) supra and Lefranc M-P et al., (1999) supra.

In certain embodiments, the CDRs of an antibody can be determined according to MacCallum R M et al., (1996) J Mol Biol 262: 732-745, herein incorporated by reference in its entirety. See also, e.g., Martin A. "Protein Sequence and Structure Analysis of Antibody Variable Domains," in *Antibody Engineering*, Kontermann and Dithel, eds., Chapter 31, pp. 422-439, Springer-Verlag, Berlin (2001), herein incorporated by reference in its entirety. In a particular embodiment, the instant disclosure provides antibodies that specifically bind to human PD-1 and comprise CDRs of an antibody disclosed in Table 6 herein (e.g., AGEN2033w or AGEN2034w) as determined by the method in MacCallum R M et al., (1996) supra.

In certain embodiments, the CDRs of an antibody can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.), herein incorporated by reference in its entirety. In a particular embodiment, the instant disclosure provides antibodies that specifically bind to human PD-1 and comprise CDRs of an antibody disclosed in Table 6 herein (e.g., AGEN2033w or AGEN2034w) as determined by the AbM numbering scheme.

Accordingly, in certain embodiments, the instant disclosure provides an isolated antibody that specifically binds to human PD-1, wherein the antibody comprises a heavy chain variable region comprising the CDRH1, CDRH2, and CDRH3 region amino acid sequences set forth in SEQ ID NO: 15, and the CDRL1, CDRL2, and CDRL3 region amino acid sequences set forth in SEQ ID NO: 16, wherein each CDR is defined in accordance with the Kabat definition, the Chothia definition, the combination of the Kabat definition and the Chothia definition, the IMGT numbering system, the AbM definition, or the contact definition of CDR.

Accordingly, in certain embodiments, the instant disclosure provides an isolated antibody that specifically binds to human PD-1, wherein the antibody comprises a heavy chain variable region comprising the CDRH1, CDRH2, and CDRH3 region amino acid sequences set forth in SEQ ID NO: 17, and the CDRL1, CDRL2, and CDRL3 region amino acid sequences set forth in SEQ ID NO: 16, wherein each CDR is defined in accordance with the Kabat definition, the Chothia definition, the combination of the Kabat definition and the Chothia definition, the IMGT numbering system, the AbM definition, or the contact definition of CDR.

In certain embodiments, the instant disclosure provides an isolated antibody that specifically binds to human PD-1, the antibody comprising a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 8, 9, 10, 11, 12, and 13, respectively.

In certain embodiments, the instant disclosure provides an isolated antibody that specifically binds to human PD-1, the antibody comprising a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 8, 9, 14, 11, 12, and 13, respectively.

In certain embodiments, the instant disclosure provides an isolated antibody that specifically binds to human PD-1, comprising a heavy chain variable region comprising the amino acid sequence of SEQ ID NO: 49.

In certain embodiments, the instant disclosure provides an isolated antibody that specifically binds to human PD-1, comprising a heavy chain variable region having an amino acid sequence derived from a human IGHV3-33 germline sequence. One or more regions selected from framework 1, framework 2, framework 3, CDRH1, and CDRH2 (e.g., two, three, four or five of these regions) can be derived from a human IGHV3-33 germline sequence. In one embodiment, framework 1, framework 2, framework 3, CDRH1, and CDRH2 are all derived from a human IGHV3-33 germline sequence. In certain embodiments, the instant disclosure provides an isolated antibody that specifically binds to human PD-1, comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to an amino acid sequence selected from the group consisting of SEQ ID NOs: 15, 17, and 26-31. In certain embodiments, the antibody comprises a heavy chain variable region having an amino acid sequence selected from the group consisting of SEQ ID NOs: 15, 17, and 26-31. In certain embodiments, the antibody comprises a heavy chain variable region having the amino acid sequence set forth in SEQ ID NO: 15. In certain embodiments, the antibody comprises a heavy chain variable region having the amino acid sequence set forth in SEQ ID NO: 17. In certain embodiments, the antibody comprises a heavy chain variable region having the amino acid sequence set forth in SEQ ID NO: 26. In certain embodiments, the antibody comprises a heavy chain variable region having the amino acid sequence set forth in SEQ ID NO: 27. In certain embodiments, the antibody comprises a heavy chain variable region having the amino acid sequence set forth in SEQ ID NO: 28. In certain embodiments, the antibody comprises a heavy chain variable region having the amino acid sequence set forth in SEQ ID NO: 29. In certain embodiments, the antibody comprises a heavy chain variable region having the amino acid sequence set forth in SEQ ID NO: 30. In certain embodiments, the antibody comprises a heavy chain variable region having the amino acid sequence set forth in SEQ ID NO: 31. In certain embodiments, the antibody comprises a heavy chain having the amino acid sequence set forth in SEQ ID NO: 18. In certain embodiments, the antibody comprises a heavy chain having the amino acid sequence set forth in SEQ ID NO: 21. In certain embodiments, the antibody comprises a heavy chain having the amino acid sequence set forth in SEQ ID NO: 20. In certain embodiments, the antibody comprises a heavy chain having the amino acid sequence set forth in SEQ ID NO: 22. In certain embodiments, the antibody comprises a heavy chain having the amino acid sequence set forth in SEQ ID NO: 23. In certain embodiments, the antibody comprises a heavy chain having the amino acid sequence set forth in SEQ ID NO: 24. In certain embodiments, the antibody comprises a heavy chain having the amino acid sequence set forth in SEQ ID NO: 25. In certain embodiments, the antibody comprises a heavy chain having the amino acid sequence set forth in SEQ ID NO: 52. In certain embodiments, the antibody comprises a heavy chain having the amino acid sequence set forth in SEQ ID NO: 53. In certain embodiments, the antibody comprises a heavy chain having the amino acid sequence set forth in SEQ ID NO: 54. In certain embodiments, the antibody comprises a heavy chain having the amino acid sequence set forth in SEQ ID NO: 55. In certain embodiments, the antibody comprises a heavy chain having the amino acid sequence set forth in SEQ ID NO: 56. In certain embodiments, the antibody comprises a heavy chain having the amino acid sequence set forth in SEQ ID NO: 57. In certain embodiments, the antibody comprises a heavy chain having the amino acid sequence set forth in SEQ ID NO: 58.

In certain embodiments, the instant disclosure provides an isolated antibody that specifically binds to human PD-1, comprising a light chain variable region having an amino acid sequence derived from a human IGKV3-15 germline sequence. One or more regions selected from framework 1, framework 2, framework 3, CDRL1, and CDRL2 (e.g., two, three, four or five of these regions) can be derived from a human IGKV3-15 germline sequence. In one embodiment, framework 1, framework 2, framework 3, CDRL1, and CDRL2 are all derived from a human IGKV3-15 germline sequence. In certain embodiments, the instant disclosure provides an isolated antibody that specifically binds to human PD-1, comprising a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 16. In certain embodiments, the antibody comprises a light chain variable region having the amino acid sequence set forth in SEQ ID NO: 16. In certain embodiments, the antibody comprises a light chain having the amino acid sequence set forth in SEQ ID NO: 19.

In certain embodiments, the instant disclosure provides an isolated antibody that specifically binds to human PD-1, comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 15 or SEQ ID NO: 17, and a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 16. In certain embodiments, the antibody comprises a heavy chain variable region having an amino acid sequence selected from the group consisting of SEQ ID NO: 15, 17, and 26-31, and a light chain variable region having the amino acid sequence set forth in SEQ ID NO: 16.

In certain embodiments, the antibody comprises the heavy chain variable region and light chain variable region amino acid sequences set forth in SEQ ID NOs: 15 and 16; 17 and 16; 26 and 16; 27 and 16; 28 and 16; 29 and 16; 30 and 16; or 31 and 16, respectively. In certain embodiments, the antibody comprises a heavy chain variable region having the amino acid sequence set forth in SEQ ID NO: 15, and a light chain variable region having the amino acid sequence set forth in SEQ ID NO: 16. In certain embodiments, the antibody comprises a heavy chain variable region having the amino acid sequence set forth in SEQ ID NO: 17, and a light chain variable region having the amino acid sequence set forth in SEQ ID NO: 16. In certain embodiments, the antibody comprises a heavy chain variable region having the amino acid sequence set forth in SEQ ID NO: 26, and a light chain variable region having the amino acid sequence set forth in SEQ ID NO: 16. In certain embodiments, the antibody comprises a heavy chain variable region having the amino acid sequence set forth in SEQ ID NO: 27, and a light chain variable region having the amino acid sequence set forth in SEQ ID NO: 16. In certain embodiments, the antibody comprises a heavy chain variable region having the amino acid sequence set forth in SEQ ID NO: 28, and a light chain variable region having the amino acid sequence set forth in SEQ ID NO: 16. In certain embodiments, the antibody comprises a heavy chain variable region having the amino acid sequence set forth in SEQ ID NO: 29, and a light chain variable region having the amino acid sequence set forth in SEQ ID NO: 16. In certain embodiments, the antibody comprises a heavy chain variable region having the amino acid sequence set forth in SEQ ID NO: 30, and a light chain variable region having the amino acid sequence set forth in SEQ ID NO: 16. In certain embodiments, the antibody comprises a heavy chain variable region having the amino acid sequence set forth in SEQ ID NO: 31, and a light chain variable region having the amino acid sequence set forth in SEQ ID NO: 16. In certain embodiments, the antibody comprises a heavy chain comprising the amino acid sequence of SEQ ID NO: 18; and a light chain comprising the amino acid sequence of SEQ ID NO: 19. In certain embodiments, the antibody comprises a heavy chain comprising the amino acid sequence of SEQ ID NO: 21; and a light chain comprising the amino acid sequence of SEQ ID NO: 19. In certain embodiments, the antibody comprises a heavy chain comprising the amino acid sequence of SEQ ID NO: 20; and a light chain comprising the amino acid sequence of SEQ ID NO: 19. In certain embodiments, the antibody comprises a heavy chain comprising the amino acid sequence of SEQ ID NO: 22; and a light chain comprising the amino acid sequence of SEQ ID NO: 19. In certain embodiments, the antibody comprises a heavy chain comprising the amino acid sequence of SEQ ID NO: 23; and a light chain comprising the amino acid sequence of SEQ ID NO: 19. In certain embodiments, the antibody comprises a heavy chain comprising the amino acid sequence of SEQ ID NO: 24; and a light chain comprising the amino acid sequence of SEQ ID NO: 19. In certain embodiments, the antibody comprises a heavy chain comprising the amino acid sequence of SEQ ID NO: 25; and a light chain comprising the amino acid sequence of SEQ ID NO: 19. In certain embodiments, the antibody comprises a heavy chain comprising the amino acid sequence of SEQ ID NO: 52; and a light chain comprising the amino acid sequence of SEQ ID NO: 19. In certain embodiments, the antibody comprises a heavy chain comprising the amino acid sequence of SEQ ID NO: 53; and a light chain comprising the amino acid sequence of SEQ ID NO: 19. In certain embodiments, the antibody comprises a heavy chain comprising the amino acid sequence of SEQ ID NO: 54; and a light chain comprising the amino acid sequence of SEQ ID NO: 19. In certain embodiments, the antibody comprises a heavy chain comprising the amino acid sequence of SEQ ID NO: 55; and a light chain comprising the amino acid sequence of SEQ ID NO: 19. In certain embodiments, the antibody comprises a heavy chain comprising the amino acid sequence of SEQ ID NO: 56; and a light chain comprising the amino acid sequence of SEQ ID NO: 19. In certain embodiments, the antibody comprises a heavy chain comprising the amino acid sequence of SEQ ID NO: 57; and a light chain comprising the amino acid sequence of SEQ ID NO: 19. In certain embodiments, the antibody comprises a heavy chain comprising the amino acid sequence of SEQ ID NO: 58; and a light chain comprising the amino acid sequence of SEQ ID NO: 19.

In certain embodiments, the instant disclosure provides an isolated antibody that cross-competes for binding to human PD-1 with an antibody comprising the heavy and light chain variable region amino acid sequences set forth in SEQ ID NOs: 15 and 16, respectively.

In certain embodiments, the instant disclosure provides an isolated antibody that binds to the same epitope on human PD-1 as an antibody comprising the heavy and light chain variable region amino acid sequences set forth in SEQ ID NOs: 15 and 16, respectively.

In certain embodiments, the instant disclosure provides an isolated antibody that cross-competes for binding to human PD-1 with an antibody comprising the heavy and light chain variable region amino acid sequences set forth in SEQ ID NOs: 17 and 16, respectively.

In certain embodiments, the instant disclosure provides an isolated antibody that binds to the same epitope on human PD-1 as an antibody comprising the heavy and light chain variable region amino acid sequences set forth in SEQ ID NOs: 17 and 16, respectively.

In certain embodiments, the instant disclosure provides an isolated antibody that cross-competes for binding to human PD-1 with an antibody comprising the heavy and light chain variable region amino acid sequences set forth in SEQ ID NOs: 26 and 16, respectively.

In certain embodiments, the instant disclosure provides an isolated antibody that binds to the same epitope on human PD-1 as an antibody comprising the heavy and light chain variable region amino acid sequences set forth in SEQ ID NOs: 26 and 16, respectively.

In certain embodiments, the instant disclosure provides an isolated antibody that cross-competes for binding to human PD-1 with an antibody comprising the heavy and light chain variable region amino acid sequences set forth in SEQ ID NOs: 27 and 16, respectively.

In certain embodiments, the instant disclosure provides an isolated antibody that binds to the same epitope on human PD-1 as an antibody comprising the heavy and light chain variable region amino acid sequences set forth in SEQ ID NOs: 27 and 16, respectively.

In certain embodiments, the instant disclosure provides an isolated antibody that cross-competes for binding to human PD-1 with an antibody comprising the heavy and light chain variable region amino acid sequences set forth in SEQ ID NOs: 28 and 16, respectively.

In certain embodiments, the instant disclosure provides an isolated antibody that binds to the same epitope on human PD-1 as an antibody comprising the heavy and light chain variable region amino acid sequences set forth in SEQ ID NOs: 28 and 16, respectively.

In certain embodiments, the instant disclosure provides an isolated antibody that cross-competes for binding to human PD-1 with an antibody comprising the heavy and light chain variable region amino acid sequences set forth in SEQ ID NOs: 29 and 16, respectively.

In certain embodiments, the instant disclosure provides an isolated antibody that binds to the same epitope on human PD-1 as an antibody comprising the heavy and light chain variable region amino acid sequences set forth in SEQ ID NOs: 29 and 16, respectively.

In certain embodiments, the instant disclosure provides an isolated antibody that cross-competes for binding to human PD-1 with an antibody comprising the heavy and light chain variable region amino acid sequences set forth in SEQ ID NOs: 30 and 16, respectively.

In certain embodiments, the instant disclosure provides an isolated antibody that binds to the same epitope on human PD-1 as an antibody comprising the heavy and light chain variable region amino acid sequences set forth in SEQ ID NOs: 30 and 16, respectively.

In certain embodiments, the instant disclosure provides an isolated antibody that cross-competes for binding to human PD-1 with an antibody comprising the heavy and light chain variable region amino acid sequences set forth in SEQ ID NOs: 31 and 16, respectively.

In certain embodiments, the instant disclosure provides an isolated antibody that binds to the same epitope on human PD-1 as an antibody comprising the heavy and light chain variable region amino acid sequences set forth in SEQ ID NOs: 31 and 16, respectively.

Any Ig constant region can be used in the antibodies disclosed herein. In certain embodiments, the Ig region is a human $IgG_1$, $IgG_2$, $IgG_3$, $IgG_4$, $IgA_1$, and $IgA_2$ heavy chain constant region. In certain embodiments, the Ig region is a human $IgG_1$. In certain embodiments, the Ig region is a human $IgG_4$. In certain embodiments, the Ig (e.g., $IgG_1$) lacks the N-linked glycan moiety that is normally present at position N297 (according to the EU numbering system) in mature wild-type $IgG_1$ antibodies in vivo. The lack of N297 glycan results in a substantial loss of effector function.

Elimination of the N297 glycan can be achieved using any methods known in the art. For example, in certain embodiments, the elimination of the N297 glycan is achieved by mutation of the N297 residue to remove the glycosylation site. Accordingly, in certain embodiments, the antibodies disclosed herein comprise a heavy chain constant region (e.g., a human $IgG_1$ heavy chain constant region) comprising an N297A mutation, according to the EU numbering system. In certain embodiments, the antibodies disclosed herein comprise a heavy chain constant region (e.g., an $IgG_1$ heavy chain constant region) comprising an N297Q mutation, according to the EU numbering system. In certain embodiments, the antibodies disclosed herein comprise an $IgG_1$ heavy chain constant region (e.g., a human $IgG_1$ heavy chain constant region) comprising a D265A mutation, according to the EU numbering system. In certain embodiments, the antibodies disclosed herein comprise an $IgG_4$ heavy chain constant region (e.g., a human $IgG_4$ heavy chain constant region) comprising an S228P mutation, according to the EU numbering system.

In certain embodiments, the instant disclosure provides an isolated antibody that specifically binds to human PD-1, the antibody comprising a heavy chain constant region comprising the amino acid sequence of SEQ ID NO: 59, 60, 61, 62, 63, or 64. In certain embodiments, the instant disclosure provides an isolated antibody that specifically binds to human PD-1, the antibody comprising a heavy chain constant region comprising the amino acid sequence of SEQ ID NO: 59. In certain embodiments, the instant disclosure provides an isolated antibody that specifically binds to human PD-1, the antibody comprising a heavy chain constant region comprising the amino acid sequence of SEQ ID NO: 60. In certain embodiments, the instant disclosure provides an isolated antibody that specifically binds to human PD-1, the antibody comprising a heavy chain constant region comprising the amino acid sequence of SEQ ID NO: 61. In certain embodiments, the instant disclosure provides an isolated antibody that specifically binds to human PD-1, the antibody comprising a heavy chain constant region comprising the amino acid sequence of SEQ ID NO: 62. In certain embodiments, the instant disclosure provides an isolated antibody that specifically binds to human PD-1, the antibody comprising a heavy chain constant region comprising the amino acid sequence of SEQ ID NO: 63. In certain embodiments, the instant disclosure provides an isolated antibody that specifically binds to human PD-1, the antibody comprising a heavy chain constant region comprising the amino acid sequence of SEQ ID NO: 64. In certain embodiments, the instant disclosure provides an isolated antibody that specifically binds to human PD-1, the antibody comprising a light chain constant region comprising the amino acid sequence of SEQ ID NO: 65.

In certain embodiments, the IgG regions of the antibodies described herein have an increased affinity for CD32B (also known as FcγRIIB or FCGR2B), e.g., as compared with an antibody with a wild-type Fc region, e.g., an $IgG_1$ Fc. In certain embodiments, antibodies described herein have a selectively increased affinity for CD32B (FcγRIIB) over both CD32A (FcγRIIA) and CD16 (FcγRIIIA) Sequence alterations that result in increased affinity for CD32B are known in the art, for example, in Mimoto et al., *Protein Engineering, Design & Selection* 10: 589-598 (2013), Chu et al., *Molecular Immunology* 45: 3926-3933 (2008), and Strohl, *Current Opinion in Biology* 20: 685-691 (2009), each of which is herein incorporated by reference in its entirety. In certain embodiments, the antibody comprises a heavy chain constant region, e.g., an $IgG_1$ constant region, or fragment thereof comprising a mutation selected from the group consisting of: G236D, P238D, S239D, S267E, L328F, and L328E, and combinations thereof, numbered according to the EU numbering system. In certain embodiments, the antibody comprises a heavy chain constant region, e.g., an $IgG_1$ constant region, or fragment thereof comprising S267E and L328F substitutions, numbered according to the EU numbering system. In certain embodiments, the antibody comprises a heavy chain constant region, e.g., an $IgG_1$ constant region, or fragment thereof comprising P238D and L328E substitutions, numbered according to the EU numbering system. In certain embodiments, the antibody comprises a heavy chain constant region, e.g., an $IgG_1$ constant region, or fragment thereof comprising a P238D substitution and substitution selected from the group consisting of E233D, G237D, H268D, P271G, A330R, and combinations thereof, numbered according to the EU numbering system. In certain embodiments, the antibody comprises a heavy chain constant region, e.g., an $IgG_1$ constant region, or fragment thereof comprising P238D, E233D, G237D, H268D, P271G, and A330R substitutions, numbered according to the EU numbering system. In certain embodiments, the antibody comprises a heavy chain constant region, e.g., an $IgG_1$ constant region, or fragment thereof comprising G236D and S267E, numbered according to the EU numbering system. In certain embodiments, the antibody comprises a heavy chain constant region, e.g., an $IgG_1$ constant region, or fragment thereof comprising S239D and S267E, numbered according to the EU numbering system. In certain embodiments, the antibody comprises a heavy chain constant region, e.g., an $IgG_1$ constant region, or fragment thereof comprising V262E, S267E, and L328F, numbered according to the EU numbering system. In certain embodiments, the antibody comprises a heavy chain constant region, e.g., an $IgG_1$ constant region, or fragment thereof comprising V264E, S267E, and L328F, numbered according to the EU numbering system.

In certain embodiments, one, two, or more mutations (e.g., amino acid substitutions) are introduced into the Fc region of an antibody described herein (e.g., CH2 domain (residues 231-340 of human $IgG_1$) and/or CH3 domain (residues 341-447 of human $IgG_1$) and/or the hinge region, numbered according to the EU numbering system, to alter one or more functional properties of the antibody, such as serum half-life, complement fixation, Fc receptor binding and/or antigen-dependent cellular cytotoxicity.

In certain embodiments, one, two, or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425, herein incorporated by reference in its entirety. The number of cysteine residues in the hinge region of the CH1 domain may be altered to, e.g., facilitate assembly of the light and heavy chains, or to alter (e.g., increase or decrease) the stability of the antibody.

In a specific embodiment, one, two, or more amino acid mutations (e.g., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745, all of which are herein incorporated by reference in their entireties, for examples of mutations that will alter (e.g., decrease or increase) the half-life of an antibody in vivo. In some embodiments, one, two or more amino acid mutations (e.g., substitutions, insertions, or deletions) are introduced into an IgG constant domain, or FcRn-binding fragment thereof (preferably an Fc or hinge-Fc domain fragment) to decrease the half-life of the antibody in vivo. In other embodiments, one, two or more amino acid mutations (e.g., substitutions, insertions or deletions) are introduced into an IgG constant domain, or FcRn-binding fragment thereof (preferably an Fc or hinge-Fc domain fragment) to increase the half-life of the antibody in vivo. In a specific embodiment, the antibodies may have one or more amino acid mutations (e.g., substitutions) in the second constant (CH2) domain (residues 231-340 of human $IgG_1$) and/or the third constant (CH3) domain (residues 341-447 of human $IgG_1$), numbered according to the EU numbering system. In a specific embodiment, the constant region of the $IgG_1$ of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU numbering system. See U.S. Pat. No. 7,658,921, which is herein incorporated by reference in its entirety. This type of mutant IgG, referred to as "YTE mutant" has been shown to display fourfold increased half-life as compared to wild-type versions of the same antibody (see Dall'Acqua W F et al., (2006) J Biol Chem 281: 23514-24, which is herein incorporated by reference in its entirety). In certain embodiments, an antibody comprises an IgG constant domain comprising one, two, three or more amino acid substitutions of amino acid residues at positions 251-257, 285-290, 308-314, 385-389, and 428-436, numbered according to the EU numbering system.

In some embodiments, one, two, or more mutations (e.g., amino acid substitutions) are introduced into the Fc region of an antibody described herein (e.g., CH2 domain (residues 231-340 of human $IgG_1$) and/or CH3 domain (residues 341-447 of human $IgG_1$) and/or the hinge region, numbered according to the EU numbering system, to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, all of which are herein incorporated by reference in their entireties.

In a further embodiment, one, two, or more amino acid substitutions are introduced into an IgG constant domain Fc region to alter the effector function(s) of the antibody. For example, one or more amino acids selected from amino acid residues 234, 235, 236, 237, 297, 318, 320 and 322, numbered according to the EU numbering system, can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, each of which is herein incorporated by reference in its entirety. In some embodiments, the deletion or inactivation (through point mutations or other means) of a constant region domain may reduce Fc receptor binding of the circulating antibody thereby increasing tumor localization. See, e.g., U.S. Pat. Nos. 5,585,097 and 8,591,886, each of which is herein incorporated by reference in its entirety, for a description of mutations that delete or inactivate the constant domain and thereby increase tumor localization. In certain embodiments, one or more amino acid substitutions may be introduced into the Fc region of an antibody described herein to remove potential glycosylation sites on Fc region, which may reduce Fc receptor binding (see, e.g., Shields R L et al., (2001) J Biol Chem 276: 6591-604, which is herein incorporated by reference in its entirety). In various embodiments, one or more of the following mutations in the constant region of an antibody described herein may be made: an N297A substitution; an N297Q substitution; a L235A substitution and a L237A substitution; a L234A substitution and a L235A substitution; a E233P substitution; a L234V substitution; a L235A substitution; a C236 deletion; a P238A substitution; a D265A substitution; a A327Q substitution; or a P329A substitution, numbered according to the EU numbering system. In certain embodiments, a mutation selected from the group consisting of D265A, P329A, and a combination thereof, numbered according to the EU numbering system, may be made in the constant region of an antibody described herein.

In a specific embodiment, an antibody described herein comprises the constant domain of an $IgG_1$ with an N297Q or N297A amino acid substitution, numbered according to the EU numbering system. In one embodiment, an antibody described herein comprises the constant domain of an $IgG_1$ with a mutation selected from the group consisting of D265A, P329A, and a combination thereof, numbered according to the EU numbering system. In another embodiment, an antibody described herein comprises the constant domain of an $IgG_1$ with a mutation selected from the group consisting of L234A, L235A, and a combination thereof, numbered according to the EU numbering system. In certain embodiments, amino acid residues in the constant region of an antibody described herein in the positions corresponding to positions L234, L235, and D265 in a human $IgG_1$ heavy chain, numbered according to the EU numbering system, are not L, L, and D, respectively. This approach is described in detail in International Publication No. WO 14/108483, which is herein incorporated by reference in its entirety. In a particular embodiment, the amino acids corresponding to positions L234, L235, and D265 in a human $IgG_1$ heavy chain are F, E, and A; or A, A, and A, respectively, numbered according to the EU numbering system.

In certain embodiments, one or more amino acids selected from amino acid residues 329, 331, and 322 in the constant region of an antibody described herein, numbered according to the EU numbering system, can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al), which is herein incorporated by reference in its entirety. In some embodiments, one or more amino acid residues within amino acid positions 231 to 238 in the N-terminal region of the CH2 domain of an antibody described herein are altered to thereby alter the ability of the antibody to fix complement, numbered according to the EU numbering system. This approach is described further in International Publication No. WO 94/29351, which is herein incorporated by reference in its entirety. In certain embodiments, the Fc region of an antibody described herein is modified to increase the ability of the antibody to mediate antibody dependent cellular cytotoxicity (ADCC) and/or to increase the affinity of the antibody for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU numbering system. This approach is described further in International Publication No. WO 00/42072, which is herein incorporated by reference in its entirety.

In certain embodiments, an antibody described herein comprises the constant region of an IgG$_4$ antibody and the serine at amino acid residue 228 of the heavy chain, numbered according to the EU numbering system, is substituted for proline. In certain embodiments, the instant disclosure provides an isolated antibody that specifically binds to human PD-1, the antibody comprising a heavy chain constant region comprising the amino acid sequence of SEQ ID NO: 63. In certain embodiments, the instant disclosure provides an isolated antibody that specifically binds to human PD-1, the antibody comprising a heavy chain constant region comprising the amino acid sequence of SEQ ID NO: 64.

In certain embodiments, any of the constant region mutations or modifications described herein can be introduced into one or both heavy chain constant regions of an antibody described herein having two heavy chain constant regions.

In certain embodiments, the instant disclosure provides an isolated antibody that specifically binds to human PD-1 and functions as an antagonist.

In certain embodiments, the instant disclosure provides an isolated antibody that specifically binds to human PD-1 and decreases PD-1 activity by at least 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to PD-1 activity without any antibody or with an unrelated antibody (e.g., an antibody that does not specifically bind to human PD-1). In certain embodiments, the instant disclosure provides an isolated antibody that specifically binds to human PD-1 and decreases PD-1 activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein and/or known to one of skill in the art, relative to PD-1 activity without any antibody or with an unrelated antibody (e.g., an antibody that does not specifically bind to human PD-1). Non-limiting examples of PD-1 activity can include PD-1 signaling, PD-1 binding to PD-1 ligand (e.g., PD-L1 or PD-L2), inhibition of cytokine production (e.g., IL-2 or IFNγ), and inhibition of T cell proliferation. In certain embodiments, the instant disclosure provides an isolated antibody that specifically binds to human PD-1 and deactivates, reduces, or inhibits a PD-1 activity. In specific embodiments, a decrease in a PD-1 activity is assessed as described in the Examples, infra.

In specific embodiments, the instant disclosure provides an isolated antibody that specifically binds to human PD-1 and reduces PD-1 binding to its ligand (e.g., PD-L1 or PD-L2) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to PD-1 binding to its ligand (e.g., PD-L1 or PD-L2) without any antibody or with an unrelated antibody (e.g., an antibody that does not specifically bind to human PD-1). In specific embodiments, the instant disclosure provides an isolated antibody that specifically binds to human PD-1 and reduces PD-1 binding to its ligand (e.g., PD-L1 or PD-L2) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to PD-1 binding to its ligand (e.g., PD-L1 or PD-L2) without any antibody or with an unrelated antibody (e.g., an antibody that does not specifically bind to human PD-1).

In specific embodiments, the instant disclosure provides an isolated antibody that specifically binds to human PD-1 and increases cytokine production (e.g., IL-2 or IFNγ) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to cytokine production without any antibody or with an unrelated antibody (e.g., an antibody that does not specifically bind to human PD-1). In specific embodiments, the instant disclosure provides an isolated antibody that specifically binds to human PD-1 and increases cytokine production (e.g., IL-2 or IFNγ) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to cytokine production without any antibody or with an unrelated antibody (e.g., an antibody that does not specifically bind to human PD-1).

In specific embodiments, the instant disclosure provides an isolated antibody that specifically binds to human PD-1 and either alone or in combination with an anti-CTLA-4 antibody (e.g., ipilimumab or tremelimumab), an anti-TIGIT antibody, an anti-CD137 antibody (e.g., urelumab or utomilumab), or an anti-OX40 antibody (e.g., pogalizumab or tavolixizumab) increases IL-2 production in human peripheral blood mononuclear cells (PBMCs) in response to Staphylococcus Enterotoxin A (SEA) stimulation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to IL-2 production without any antibody or with an unrelated antibody (e.g., an antibody that does not specifically bind to human PD-1).

In certain embodiments, human peripheral blood mononuclear cells (PBMCs) stimulated with Staphylococcus Enterotoxin A (SEA) in the presence of an antibody described herein, which specifically binds to human PD-1, either alone or in combination with an anti-CTLA-4 antibody (e.g., ipilimumab or tremelimumab), an anti-TIGIT antibody, an anti-CD137 antibody (e.g., urelumab or utomilumab), or an anti-OX40 antibody (e.g., pogalizumab or tavolixizumab), have increased IL-2 production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold relative to PBMCs only stimulated with SEA without any antibody or with an unrelated antibody (e.g., an antibody that does not specifically bind to human PD-1), as assessed by methods described herein (see the Examples, infra) or known to one of skill in the art.

In specific embodiments, the instant disclosure provides an isolated antibody that specifically binds to human PD-1 and increases IFNγ production of a co-culture of human T cells and allogenic dendritic cells by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to IFNγ production of a co-culture of human T cells and allogenic dendritic cells without any antibody or with an unrelated antibody (e.g., an antibody that does not specifically bind to human PD-1).

In certain embodiments, a co-culture of human T cells and allogenic dendritic cells in the presence of an antibody described herein, which specifically binds to human PD-1, has increased IFNγ production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold relative to a co-culture of human T cells and allogenic dendritic cells without any antibody or with an unrelated antibody (e.g., an antibody that does not specifically bind to human PD-1), as assessed by methods described herein (see the Examples, infra) or known to one of skill in the art.

In specific embodiments, the instant disclosure provides an isolated antibody that specifically binds to human PD-1 and increases T cell proliferation by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to T cell proliferation without any antibody or with an unrelated antibody (e.g., an antibody that does not specifically bind to human PD-1). In specific embodiments, the instant disclosure provides an isolated antibody that specifically binds to human PD-1 and increases T cell proliferation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to T cell proliferation without any antibody or with an unrelated antibody (e.g., an antibody that does not specifically bind to human PD-1).

In specific embodiments, the instant disclosure provides an isolated antibody that specifically binds to human PD-1 and increases proliferation of anti-CD3-antibody-stimulated CD4+ or CD8+ T cells co-cultured with ovarian cancer ascites fluid by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to proliferation of anti-CD3-antibody-stimulated CD4+ or CD8+ T cells co-cultured with ovarian cancer ascites fluid without any antibody or with an unrelated antibody (e.g., an antibody that does not specifically bind to human PD-1).

In specific embodiments, the instant disclosure provides an isolated antibody that specifically binds to human PD-1 and increases NFAT signaling in PD-1-expressing NFAT-luciferase reporter cells co-cultured with PD-L1-expressing target cells by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to NFAT signaling in PD-1-expressing NFAT-luciferase reporter cells co-cultured with PD-L1-expressing target cells without any antibody or with an unrelated antibody (e.g., an antibody that does not specifically bind to human PD-1).

5.3 Pharmaceutical Compositions

Provided herein are compositions comprising an anti-PD-1 antibody described herein having the desired degree of purity in a physiologically acceptable carrier, excipient or stabilizer (Remington's Pharmaceutical Sciences (1990) Mack Publishing Co., Easton, Pa.). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In a specific embodiment, pharmaceutical compositions comprise an anti-PD-1 antibody described herein, and optionally one or more additional prophylactic or therapeutic agents, in a pharmaceutically acceptable carrier. In a specific embodiment, pharmaceutical compositions comprise an effective amount of an antibody described herein, and optionally one or more additional prophylactic or therapeutic agents, in a pharmaceutically acceptable carrier. In some embodiments, the antibody is the only active ingredient included in the pharmaceutical composition. Pharmaceutical compositions described herein can be useful in inhibiting PD-1 activity and treating a condition, such as cancer or an infectious disease. In a preferred embodiment, the present invention relates to a pharmaceutical composition of the present invention comprising an anti-PD-1 antibody of the present invention for use as a medicament. In another preferred embodiment, the present invention relates to a pharmaceutical composition of the present invention for use in a method for the treatment of cancer or an infectious disease. In another preferred embodiment, the present invention relates to the use of an anti-PD-1 antibody of the present invention for preparing a pharmaceutical composition for treating cancer or an infectious disease.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition may be formulated for any route of administration to a subject. Specific examples of routes of administration include intranasal, oral, pulmonary, transdermal, intradermal, and parenteral. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An anti-PD-1 antibody described herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma and are incorporated by reference in their entireties). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

An anti-PD-1 antibody described herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957, all of which are herein incorporated by reference in their entireties.

In certain embodiments, a pharmaceutical composition comprising an antibody described herein is a lyophilized powder, which can be reconstituted for administration as solutions, emulsions and other mixtures. It may also be reconstituted and formulated as solids or gels. The lyophilized powder is prepared by dissolving an antibody described herein, or a pharmaceutically acceptable derivative thereof, in a suitable solvent. In some embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature. Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The anti-PD-1 antibodies described herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874, all of which are herein incorporated by reference in their entireties. In a specific embodiment, an antibody described herein is targeted to a tumor.

The compositions to be used for in vivo administration can be sterile. This is readily accomplished by filtration through, e.g., sterile filtration membranes.

5.4 Methods of Use and Uses

In another aspect, the instant disclosure provides a method of treating a subject using the anti-PD-1 antibodies disclosed herein. Any disease or disorder in a subject that would benefit from inhibition of PD-1 function can be treated using the anti-PD-1 antibodies disclosed herein. The anti-PD-1 antibodies disclosed herein are particularly useful for inhibiting immune system tolerance to tumors, and accordingly can be used as an immunotherapy for subjects with cancer. For example, in certain embodiments, the instant disclosure provides a method of increasing T cell activation in response to an antigen in a subject, the method comprising administering to the subject an effective amount of an anti-PD-1 antibody or pharmaceutical composition thereof, as disclosed herein. In certain embodiments, the instant disclosure provides a method of treating cancer in a subject, the method comprising administering to the subject an effective amount of the antibody or pharmaceutical composition, as disclosed herein. Cancers that can be treated with the anti-PD-1 antibodies or pharmaceutical compositions disclosed herein include, without limitation, melanoma, head and neck cancer (e.g., head and neck squamous cancer), lung cancer (e.g., non-small cell lung cancer and small cell lung cancer), breast cancer (e.g., herceptin resistant breast cancer and trastuzumab-DM1 (T-DM1) resistant breast cancer), prostate cancer, glioblastoma multiforme, colorectal cancer, sarcoma, bladder cancer, cervical cancer, HPV-associated cancers, cancers of the vagina, cancers of the vulva, cancers of the penis, cancers of the anus, cancers of the rectum, cancers of the oropharynx, multiple myeloma, renal cell carcinoma, ovarian cancer, hepatocellular cancer, endometrial cancer, pancreatic cancer, lymphoma, and leukemia (e.g., elderly leukemia, acute myeloid leukemia (AML), and elderly AML). Therefore, the present invention relates in one embodiment to an antibody and/or pharmaceutical composition of the present invention for use as a medicament. In a preferred embodiment, the present invention relates to the use of an antibody and/or pharmaceutical composition of the present invention for preparing a medicine for use in a method of treating cancer in a subject, and/or for use for inhibiting immune system tolerance to tumors and/or for use in immunotherapy for subjects with cancer, and/or for use in a method of increasing T cell activation in response to an antigen in a subject. In a preferred embodiment, the cancer is selected from the group consisting of melanoma, head and neck cancer (e.g., head and neck squamous cancer), lung cancer (e.g., non-small cell lung cancer and small cell lung cancer), breast cancer (e.g., herceptin resistant breast cancer and trastuzumab-DM1 (T-DM1) resistant breast cancer), prostate cancer, glioblastoma multiforme, colorectal cancer, sarcoma, bladder cancer, cervical cancer, HPV-associated cancers, cancers of the vagina, cancers of the vulva, cancers of the penis, cancers of the anus, cancers of the rectum, cancers of the oropharynx, multiple myeloma, renal cell carcinoma, ovarian cancer, hepatocellular cancer, endometrial cancer, pancreatic cancer, lymphoma, and leukemia (e.g., elderly leukemia, acute myeloid leukemia (AML), and elderly AML).

Additional cancers that can be treated with the anti-PD-1 antibodies or pharmaceutical compositions disclosed herein include, without limitation, melanoma (e.g., metastatic malignant melanoma and cutaneous or intraocular malignant melanoma), renal cancer (e.g., clear cell carcinoma), prostate cancer (e.g., hormone refractory prostate adenocarcinoma), breast cancer, colon cancer, lung cancer (e.g., non-small cell lung cancer), bone cancer, pancreatic cancer, skin cancer, cancer of the head or neck, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, glioma, pituitary adenoma, Kaposi's sarcoma, epidermoid cancer, squamous cell cancer, T-cell lymphoma, environmentally induced cancers including those induced by asbestos, esophageal cancer, liver cancer, refractory or recurrent malignancies, metastatic cancers, cancers that express PD-L1, and combinations of said cancers.

In certain embodiments, the instant disclosure provides a method of preventing or treating an infectious disease in a subject, the method comprising administering to the subject an effective amount of an anti-PD-1 antibody or pharmaceutical composition thereof, as disclosed herein. In one embodiment, provided herein are methods for preventing and/or treating an infection (e.g., a viral infection, a bacterial infection, a fungal infection, a protozoal infection, or a parasitic infection). The infection prevented and/or treated in accordance with the methods can be caused by an infectious agent identified herein. In a specific embodiment, an anti-PD-1 antibody described herein or a composition thereof is the only active agent administered to a subject. In some embodiments, an anti-PD-1 antibody described herein or a composition thereof is used in combination with anti-infective interventions (e.g., antivirals, antibacterials, antifungals, or anti-helminthics) for the treatment of infectious diseases. Therefore, in a preferred embodiment, the present invention relates to an antibody, the use of such antibody for preparing pharmaceutical compositions, and/or pharmaceutical compositions of the present invention for use in a method of preventing and/or treating an infectious disease, more preferably wherein the antibody or pharmaceutical composition is the only active agent administered to a subject, or wherein the antibody or pharmaceutical composition is used in combination with anti-infective interventions.

Infectious diseases that can be treated and/or prevented by anti-PD-1 antibodies or pharmaceutical compositions disclosed herein are caused by infectious agents including but not limited to bacteria, parasites, fungi, protozae, and viruses. In a specific embodiment, the infectious disease treated and/or prevented by anti-PD-1 antibodies or pharmaceutical compositions disclosed herein is caused by a virus. Viral diseases or viral infections that can be prevented and/or treated in accordance with the methods described herein include, but are not limited to, those caused by hepatitis type A, hepatitis type B, hepatitis type C, influenza (e.g., influenza A or influenza B), varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral meningitis, encephalitis, dengue or small pox.

Bacterial infections that can be prevented and/or treated include infections caused by *Escherichia coli, Klebsiella pneumoniae, Staphylococcus aureus, Enterococcus faecalis, Proteus vulgaris, Staphylococcus viridans*, and *Pseudomonas aeruginosa*. Bacterial diseases caused by bacteria (e.g., *Escherichia coli, Klebsiella pneumoniae, Staphylococcus aureus, Enterococcus faecalis, Proteus vulgaris, Staphylococcus viridans*, and *Pseudomonas aeruginosa*) that can be prevented and/or treated in accordance with the methods described herein include, but are not limited to, *Mycobacteria rickettsia, Mycoplasma, Neisseria, S. pneumonia, Borrelia burgdorferi* (Lyme disease), *Bacillus antracis* (anthrax), tetanus, *Streptococcus, Staphylococcus, mycobacterium*, pertissus, cholera, plague, diptheria, *chlamydia, S. aureus* and *legionella*.

Protozoal diseases or protozoal infections caused by protozoa that can be prevented and/or treated in accordance with the methods described herein include, but are not limited to, leishmania, coccidiosis, *trypanosoma schistosoma* or malaria. Parasitic diseases or parasitic infections caused by parasites that can be prevented and/or treated in accordance with the methods described herein include, but are not limited to, *chlamydia* and *rickettsia*.

Fungal diseases or fungal infections that can be prevented and/or treated in accordance with the methods described herein include, but are not limited to, those caused by *Candida* infections, zygomycosis, *Candida* mastitis, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, *Aspergillus niger* infection, *Fusarium keratitis*, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, *Cryptococcus neoformans* infection, fungal peritonitis, *Curvularia geniculata* infection, staphylococcal endophthalmitis, sporotrichosis, and dermatophytosis.

In certain embodiments, these methods further comprise administering an additional therapeutic agent to the subject. In certain embodiments, the additional therapeutic agent is a chemotherapeutic, a radiotherapeutic, or a checkpoint targeting agent. In certain embodiments, the checkpoint targeting agent is selected from the group consisting of an antagonist anti-CTLA-4 antibody, an antagonist anti-PD-L1 antibody, an antagonist anti-PD-L2 antibody, an antagonist anti-PD-1 antibody, an antagonist anti-TIM-3 antibody, an antagonist anti-LAG-3 antibody, an antagonist anti-CEACAM1 antibody, an antagonist anti-TIGIT antibody, an agonist anti-CD137 antibody, an agonist anti-ICOS antibody, an agonist anti-GITR antibody, and an agonist anti-OX40 antibody. In certain embodiments, an anti-PD-1 antibody disclosed herein is administered to a subject in combination with an antagonist anti-CTLA-4 antibody and an agonist anti-ICOS antibody. In certain embodiments, an anti-PD-1 antibody disclosed herein is administered to a subject in combination with an antagonist anti-CTLA-4 antibody. In certain embodiments, the instant disclosure provides a method of treating cancer in a subject, the method comprising administering to the subject an anti-PD-1 antibody or pharmaceutical composition thereof, as disclosed herein, in combination with an antagonist anti-CTLA-4 antibody or pharmaceutical composition thereof, wherein the cancer is selected from the group consisting of lung cancer (e.g., non-small cell lung cancer (NSCLC), e.g., first-line NSCLC), melanoma (e.g., first-line melanoma), and head and neck cancer (e.g., squamous cell carcinoma of the head and neck (SCCHN), e.g., first-line SCCHN).

In a preferred embodiment, the present invention relates to an antibody, the use of such antibody for preparing pharmaceutical compositions and/or pharmaceutical composition of the present invention for use in a method of the present invention, wherein the method further comprises administering an additional therapeutic agent to the subject. In another preferred embodiment, the present invention relates to (a) an antibody and/or pharmaceutical composition of the present invention and (b) an additional therapeutic agent for use as a medicament. In another preferred embodiment, the present invention relates to (a) an antibody and/or pharmaceutical composition of the present invention, and (b) an additional therapeutic agent for use in a method for the treatment of cancer. In a further embodiment, the present invention relates to a pharmaceutical composition, kit or kit-of-parts comprising (a) an antibody and/or pharmaceutical composition of the present invention and (b) an additional therapeutic agent. In one more preferred embodiment, the additional therapeutic agent is a chemotherapeutic, a radiotherapeutic, or a checkpoint targeting agent.

In certain embodiments, an anti-CTLA-4 antibody is used in methods disclosed herein. In certain embodiments, the anti-CTLA-4 antibody is Ipilimumab developed by Bristol-Myers Squibb. In certain embodiments, the anti-CTLA-4 antibody is Tremelimumab developed by Pfizer and Medimmune. In certain embodiments, the anti-CTLA-4 antibody is a Probody targeting CTLA-4 developed by CytomX and Bristol-Myers Squibb.

Non-limiting examples of anti-CTLA-4 antibodies that may be used in treatment methods disclosed herein are disclosed in the following patents and patent applications, all of which are herein incorporated by reference in their entireties: U.S. Pat. Nos. 6,984,720; 7,411,057; 7,034,121; 8,697,845; 8,518,404; U.S. Publication No. US 2009/0123477 A1; U.S. Publication No. US 2014/0105914 A1; U.S. Publication No. US 2013/0267688 A1; U.S. Publication No. US 2016/0145355 A1; PCT Publication No. WO 2014/207064 A1; and PCT Publication No. WO 2016/015675 A1.

In certain embodiments, an anti-PD-1 antibody disclosed herein is administered to a subject in combination with a compound that targets an immunomodulatory enzyme(s) such as IDO (indoleamine-(2,3)-dioxygenase) and/or TDO (tryptophan 2,3-dioxygenase). Therefore, in another more preferred embodiment, the additional therapeutic agent is a compound that targets an immunomodulatory enzyme(s), even more preferably an inhibitor of indoleamine-(2,3)- dioxygenase (IDO). In certain embodiments, such compound is selected from the group consisting of epacadostat (Incyte Corp; see, e.g., WO 2010/005958 which is incorporated by reference herein in its entirety), F001287 (Flexus Biosciences/Bristol-Myers Squibb), indoximod (NewLink Genetics), and NLG919 (NewLink Genetics). In one embodiment, the compound is epacadostat. In another embodiment, the compound is F001287. In another embodiment, the compound is indoximod. In another embodiment, the compound is NLG919.

In certain embodiments, an anti-PD-1 antibody disclosed herein is administered to a subject in combination with a vaccine. The vaccine can be, e.g., a peptide vaccine, a DNA vaccine, or an RNA vaccine. In certain embodiments, the vaccine is a heat shock protein based tumor vaccine or a heat shock protein based pathogen vaccine. In a specific embodiment, an anti-PD-1 antibody disclosed herein is administered to a subject in combination with a heat shock protein based tumor-vaccine. Heat shock proteins (HSPs) are a family of highly conserved proteins found ubiquitously across all species. Their expression can be powerfully induced to much higher levels as a result of heat shock or other forms of stress, including exposure to toxins, oxidative stress or glucose deprivation. Five families have been classified according to molecular weight: HSP-110, -90, -70, -60 and -28. HSPs deliver immunogenic peptides through the cross-presentation pathway in antigen presenting cells (APCs) such as macrophages and dendritic cells (DCs), leading to T cell activation. HSPs function as chaperone carriers of tumor-associated antigenic peptides forming complexes able to induce tumor-specific immunity. Upon release from dying tumor cells, the HSP-antigen complexes are taken up by antigen-presenting cells (APCs) wherein the antigens are processed into peptides that bind MHC class I and class II molecules leading to the activation of anti-tumor CD8+ and CD4+ T cells. The immunity elicited by HSP complexes derived from tumor preparations is specifically directed against the unique antigenic peptide repertoire expressed by the cancer of each subject. Therefore, in a further preferred embodiment, the present invention relates to (a) an antibody and/or pharmaceutical composition of the present invention and (b) a vaccine for use as a medicament, in particular for use in a method for the treatment of cancer. In another preferred embodiment, the present invention relates to a pharmaceutical composition, kit or kit-of-parts comprising (a) an antibody and/or pharmaceutical composition of the present invention and (b) a vaccine. In a further preferred embodiment, the vaccine is a heat shock protein based tumor vaccine or a heat shock protein based pathogen vaccine, more preferably a heat shock protein based tumor vaccine.

A heat shock protein peptide complex (HSPPC) is a protein peptide complex consisting of a heat shock protein non-covalently complexed with antigenic peptides. HSPPCs elicit both innate and adaptive immune responses. In a specific embodiment, the antigenic peptide(s) displays antigenicity for the cancer being treated. HSPPCs are efficiently seized by APCs via membrane receptors (mainly CD91) or by binding to Toll-like receptors. HSPPC internalization results in functional maturation of the APCs with chemokine and cytokine production leading to activation of natural killer cells (NK), monocytes and Th1 and Th-2-mediated immune responses. In certain embodiments, HSPPCs used in methods disclosed herein comprise one or more heat shock proteins from the hsp60, hsp70, or hsp90 family of stress proteins complexed with antigenic peptides. In certain embodiments, HSPPCs comprise hsc70, hsp70, hsp90, hsp110, grp170, gp96, calreticulin, or combinations of two or more thereof.

In a specific embodiment, the heat shock protein peptide complex (HSPPC) comprises recombinant heat shock proteins (e.g., hsp70 or hsc70) or a peptide-binding domain thereof complexed with recombinant antigenic peptides. Recombinant heat shock proteins can be produced by recombinant DNA technology, for example, using human hsc70 sequence as described in Dworniczak and Mirault, Nucleic Acids Res. 15:5181-5197 (1987) and GenBank accession no. P11142 and/or Y00371, each of which is incorporated herein by reference in its entirety. In certain embodiments, Hsp70 sequences are as described in Hunt and Morimoto Proc. Natl. Acad. Sci. U.S.A. 82 (19), 6455-6459 (1985) and GenBank accession no. P0DMV8 and/or M11717, each of which is incorporated herein by reference in its entirety. Antigenic peptides can also be prepared by recombinant DNA methods known in the art.

In certain embodiments, the antigenic peptides comprise a modified amino acid. In certain embodiments, the modified amino acid comprises a post-translational modification. In certain embodiments, the modified amino acid comprises a mimetic of a post-translational modification. In certain embodiments, the modified amino acid is a Tyr, Ser, Thr, Arg, Lys, or His that has been phosphorylated on a side chain hydroxyl or amine. In certain embodiments, the modified amino acid is a mimetic of a Tyr, Ser, Thr, Arg, Lys, or His amino acid that has been phosphorylated on a side chain hydroxyl or amine.

In a specific embodiment, an anti-PD-1 antibody disclosed herein is administered to a subject in combination with a heat shock protein peptide complex (HSPPC), e.g., heat shock protein peptide complex-96 (HSPPC-96), to treat cancer. HSPPC-96 comprises a 96 kDa heat shock protein (Hsp), gp96, complexed to antigenic peptides. HSPPC-96 is a cancer immunotherapy manufactured from a subject's tumor and contains the cancer's antigenic "fingerprint." In certain embodiments, this fingerprint contains unique antigens that are present only in that particular subject's specific cancer cells and injection of the vaccine is intended to stimulate the subject's immune system to recognize and attack any cells with the specific cancer fingerprint. Therefore, in another preferred embodiment, the present invention relates to an antibody and/or pharmaceutical composition of the present invention in combination with a heat shock protein peptide complex (HSPPC) for use as a medicament and/or for use in a method for the treatment of cancer.

In certain embodiments, the HSPPC, e.g., HSPPC-96, is produced from the tumor tissue of a subject. In a specific embodiment, the HSPPC (e.g., HSPPC-96) is produced from a tumor of the type of cancer or metastasis thereof being treated. In another specific embodiment, the HSPPC (e.g., HSPPC-96) is autologous to the subject being treated. In certain embodiments, the tumor tissue is non-necrotic tumor tissue. In certain embodiments, at least 1 gram (e.g., at least 1, at least 2, at least 3, at least 4, at least 5, at least 6, at least 7, at least 8, at least 9, or at least 10 grams) of non-necrotic tumor tissue is used to produce a vaccine regimen. In certain embodiments, after surgical resection, non-necrotic tumor tissue is frozen prior to use in vaccine preparation. In some embodiments, the HSPPC, e.g., HSPPC-96, is isolated from the tumor tissue by purification techniques, filtered and prepared for an injectable vaccine. In certain embodiments, a subject is administered 6-12 doses of the HSPPC, e.g., HSPCC-96. In such embodiments, the HSPPC, e.g., HSPPC-96, doses may be administered weekly for the first 4 doses and then biweekly for the 2-8 additional doses.

Further examples of HSPPCs that may be used in accordance with the methods described herein are disclosed in the following patents and patent applications, U.S. Pat. Nos. 6,391,306, 6,383,492, 6,403,095, 6,410,026, 6,436,404, 6,447,780, 6,447,781 and 6,610,659, all of which are herein incorporated by reference in their entireties.

In certain embodiments, an anti-PD-1 antibody disclosed herein is administered to a subject in combination with an adjuvant. Various adjuvants can be used depending on the treatment context. Non-limiting examples of appropriate adjuvants include, but not limited to, Complete Freund's Adjuvant (CFA), Incomplete Freund's Adjuvant (IFA), montanide ISA (incomplete Seppic adjuvant), the Ribi adjuvant system (RAS), Titer Max, muramyl peptides, Syntex Adjuvant Formulation (SAF), alum (aluminum hydroxide and/or aluminum phosphate), aluminum salt adjuvants, Gerbu® adjuvants, nitrocellulose absorbed antigen, encapsulated or entrapped antigen, 3 De-O-acylated monophosphoryl lipid A (3 D-MPL), immunostimulatory oligonucleotides, toll-like receptor (TLR) ligands, mannan-binding lectin (MBL) ligands, STING agonists, immuno-stimulating complexes such as saponins, Quil A, QS-21, QS-7, ISCOMATRIX, and others. Other adjuvants include CpG oligonucleotides and double stranded RNA molecules, such as poly(A) and poly(U). Combinations of the above adjuvants may also be used. See, e.g., U.S. Pat. Nos. 6,645,495; 7,029,678; and 7,858,589, all of which are incorporated herein by reference in their entireties. In one embodiment, the adjuvant used herein is QS-21 STIMULON.

In certain embodiments, an anti-PD-1 antibody disclosed herein is administered to a subject in combination with an additional therapeutic agent comprising a TCR. In certain embodiments, the additional therapeutic agent is a soluble TCR. In certain embodiments, the additional therapeutic agent is a cell expressing a TCR. Therefore, in another preferred embodiment, the present invention relates to an antibody and/or pharmaceutical composition of the present invention in combination with an additional therapeutic agent comprising a TCR for use as a medicament and/or for use in a method for the treatment of cancer.

In certain embodiments, an anti-PD-1 antibody disclosed herein is administered to a subject in combination with a cell expressing a chimeric antigen receptor (CAR). In certain embodiments, the cell is a T cell.

In certain embodiments, an anti-PD-1 antibody disclosed herein is administered to a subject in combination with a TCR mimic antibody. In certain embodiments, the TCR mimic antibody is an antibody that specifically binds to a peptide-MHC complex. For non-limiting examples of TCR mimic antibodies, see, e.g., U.S. Pat. No. 9,074,000 and U.S. Publication Nos. US 2009/0304679 A1 and US 2014/0134191 A1, all of which are incorporated herein by reference in their entireties.

The anti-PD-1 antibody and the additional therapeutic agent (e.g., chemotherapeutic, radiotherapeutic, checkpoint targeting agent, IDO inhibitor, vaccine, adjuvant, a soluble TCR, a cell expressing a TCR, a cell expressing a chimeric antigen receptor, and/or a TCR mimic antibody) can be administered separately, sequentially or concurrently as separate dosage forms. In one embodiment, an anti-PD-1 antibody is administered parenterally, and an IDO inhibitor is administered orally.

An antibody or pharmaceutical composition described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival, intra-arterial, and subcutaneous routes. Pulmonary administration can also be employed, e.g., by use of an inhaler or nebulizer, and formulation with an aerosolizing agent for use as a spray. In certain embodiments, the antibody or pharmaceutical composition described herein is delivered subcutaneously or intravenously. In certain embodiments, the antibody or pharmaceutical composition described herein is delivered intra-arterially. In certain embodiments, the antibody or pharmaceutical composition described herein is delivered intratumorally. In certain embodiments, the antibody or pharmaceutical composition described herein is delivered to a tumor draining lymph node.

The amount of an antibody or composition which will be effective in the treatment and/or prevention of a condition will depend on the nature of the disease, and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human but non-human mammals including transgenic mammals can also be treated. Treatment dosages are optimally titrated to optimize safety and efficacy.

An anti-PD-1 antibody described herein can also be used to assay PD-1 protein levels in a biological sample using classical immunohistological methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In) and technetium ($^{99}$Tc); luminescent labels, such as luminol; and fluorescent labels, such as fluorescein and rhodamine, and biotin. Such labels can be used to label an antibody described herein. Alternatively, a second antibody that recognizes an anti-PD-1 antibody described herein can be labeled and used in combination with an anti-PD-1 antibody to detect PD-1 protein levels. Therefore, in one embodiment, the present invention relates to the use of an antibody of the present invention for in vitro detection of human PD-1 protein in a biological sample. In a further embodiment, the present invention relates to the use of an anti-PD-1 antibody of the invention, for assaying and/or detecting human PD-1 protein levels in a biological sample in vitro, preferably wherein the anti-PD-1 antibody is conjugated to a radionuclide or detectable label, and/or carries a label described herein, and/or wherein an immunohistological method is used.

Assaying for the expression level of PD-1 protein is intended to include qualitatively or quantitatively measuring or estimating the level of PD-1 protein in a first biological sample either directly (e.g., by determining or estimating absolute protein level) or relatively (e.g., by comparing to the disease associated protein level in a second biological sample). PD-1 polypeptide expression level in the first biological sample can be measured or estimated and compared to a standard PD-1 protein level, the standard being taken from a second biological sample obtained from an individual not having the disorder or being determined by averaging levels from a population of individuals not having the disorder. As will be appreciated in the art, once the "standard" PD-1 polypeptide level is known, it can be used repeatedly as a standard for comparison. Therefore, in a further embodiment, the present invention relates to an in vitro method for assaying and/or detecting PD-1 protein levels, in particular human PD-1 protein levels, in a biological sample, comprising qualitatively or quantitatively measuring or estimating the level of PD-1 protein, in particular of human PD-1 protein, in a biological sample, by an immunohistological method.

As used herein, the term "biological sample" refers to any biological sample obtained from a subject, cell line, tissue, or other source of cells potentially expressing PD-1. Methods for obtaining tissue biopsies and body fluids from animals (e.g., humans) are well known in the art. Biological samples include peripheral mononuclear blood cells.

An anti-PD-1 antibody described herein can be used for prognostic, diagnostic, monitoring and screening applications, including in vitro and in vivo applications well known and standard to the skilled artisan and based on the present description. Prognostic, diagnostic, monitoring and screening assays and kits for in vitro assessment and evaluation of immune system status and/or immune response may be utilized to predict, diagnose and monitor to evaluate patient samples including those known to have or suspected of having an immune system-dysfunction or with regard to an anticipated or desired immune system response, antigen response or vaccine response. The assessment and evaluation of immune system status and/or immune response is also useful in determining the suitability of a patient for a clinical trial of a drug or for the administration of a particular chemotherapeutic agent, a radiotherapeutic agent, or an antibody, including combinations thereof, versus a different agent or antibody. This type of prognostic and diagnostic monitoring and assessment is already in practice utilizing antibodies against the HER2 protein in breast cancer (HercepTest™, Dako) where the assay is also used to evaluate patients for antibody therapy using Herceptin®. In vivo applications include directed cell therapy and immune system modulation and radio imaging of immune responses. Therefore, in one embodiment, the present invention relates to an anti-PD-1 antibody, the use of such antibody for preparing a pharmaceutical composition and/or pharmaceutical compositions of the present invention for use as a diagnostic. In a preferred embodiment, the present invention relates to an anti-PD-1 antibody, the use of such antibody for preparing a pharmaceutical composition and/or pharmaceutical compositions of the present invention for use in a method for the prediction, diagnosis and/or monitoring of a subject having or suspected to have an immune system-dysfunction and/or with regard to an anticipated or desired immune system response, antigen response or vaccine response. In another embodiment, the present invention relates to the use of anti-PD-1 antibody of the invention, for predicting, diagnosing and/or monitoring of a subject having or suspected to have an immune system-dysfunction and/or with regard to an anticipated or desired immune system response, antigen response or vaccine response by assaying and/or detecting human PD-1 protein levels in a biological sample of the subject in vitro.

In one embodiment, an anti-PD-1 antibody can be used in immunohistochemistry of biopsy samples. Preferably, the method is an in vitro method. In another embodiment, an anti-PD-1 antibody can be used to detect levels of PD-1, or levels of cells which contain PD-1 on their membrane surface, which levels can then be linked to certain disease symptoms. Anti-PD-1 antibodies described herein may carry a detectable or functional label and/or may be conjugated to a radionuclide or detectable label. When fluorescence labels are used, currently available microscopy and fluorescence-activated cell sorter analysis (FACS) or combination of both methods procedures known in the art may be utilized to identify and to quantitate the specific binding members. Anti-PD-1 antibodies described herein may carry or may be conjugated to a fluorescence label. Exemplary fluorescence labels include, for example, reactive and conjugated probes, e.g., Aminocoumarin, Fluorescein and Texas red, Alexa Fluor dyes, Cy dyes and DyLight dyes. An anti-PD-1 antibody may carry or may be conjugated to a radioactive label or radionuclide, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{37}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. When radioactive labels are used, currently available counting procedures known in the art may be utilized to identify and quantitate the specific binding of anti-PD-1 antibody to PD-1 (e.g., human PD-1). In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an anti-PD-1 antibody under conditions that allow for the formation of a complex between the antibody and PD-1. Any complexes formed between the antibody and PD-1 are detected and compared in the sample and the control. In light of the specific binding of the antibodies described herein for PD-1, the antibodies can be used to specifically detect PD-1 expression on the surface of cells. The antibodies described herein can also be used to purify PD-1 via immunoaffinity purification. Also included herein is an assay system which may be prepared in the form of a test kit, kit or kit-of-parts for the quantitative analysis of the extent of the presence of, for instance, PD-1 or PD-1/PD-1 ligand complexes. The system, test kit, kit or kit-of-parts may comprise a labeled component, e.g., a labeled antibody, and one or more additional immunochemical reagents.

5.5 Polynucleotides, Vectors and Methods of Producing Anti-PD-1 Antibodies

In another aspect, provided herein are polynucleotides comprising a nucleotide sequence encoding an antibody described herein or a fragment thereof (e.g., a light chain variable region and/or heavy chain variable region) that specifically binds to a PD-1 (e.g., human PD-1) antigen, and vectors, e.g., vectors comprising such polynucleotides for recombinant expression in host cells (e.g., *E. coli* and mammalian cells). Provided herein are polynucleotides comprising nucleotide sequences encoding a heavy and/or light chain of any of the antibodies provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an antibody described herein is isolated or purified.

In particular aspects, provided herein are polynucleotides comprising nucleotide sequences encoding antibodies, which specifically bind to a PD-1 polypeptide (e.g., human PD-1) and comprises an amino acid sequence as described herein, as well as antibodies which compete with such antibodies for binding to a PD-1 polypeptide (e.g., in a dose-dependent manner), or which binds to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding a light chain comprising the VL FRs and CDRs of antibodies described herein (see, e.g., Tables 3 and 5) or nucleotide sequences encoding a heavy chain comprising the VH FRs and CDRs of antibodies described herein (see, e.g., Tables 2 and 4).

Also provided herein are polynucleotides encoding an anti-PD-1 antibody that are optimized, e.g., by codon/RNA optimization, replacement with heterologous signal sequences, and elimination of mRNA instability elements. Methods to generate optimized nucleic acids encoding an anti-PD-1 antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly, all of which are herein incorporated by reference in their entireties. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid. Such methods can increase expression of an anti-PD-1 antibody or fragment thereof by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an anti-PD-1 antibody encoded by polynucleotides that have not been optimized.

In certain embodiments, an optimized polynucleotide sequence encoding an anti-PD-1 antibody described herein or a fragment thereof (e.g., VL domain and/or VH domain) can hybridize to an antisense (e.g., complementary) polynucleotide of an unoptimized polynucleotide sequence encoding an anti-PD-1 antibody described herein or a fragment thereof (e.g., VL domain and/or VH domain). In specific embodiments, an optimized nucleotide sequence encoding an anti-PD-1 antibody described herein or a fragment hybridizes under high stringency conditions to antisense polynucleotide of an unoptimized polynucleotide sequence encoding an anti-PD-1 antibody described herein or a fragment thereof. In a specific embodiment, an optimized nucleotide sequence encoding an anti-PD-1 antibody described herein or a fragment thereof hybridizes under high stringency, intermediate or lower stringency hybridization conditions to an antisense polynucleotide of an unoptimized nucleotide sequence encoding an anti-PD-1 antibody described herein or a fragment thereof. Information regarding hybridization conditions has been described, see, e.g., U.S. Patent Application Publication No. US 2005/0048549 (e.g., paragraphs 72-73), which is incorporated herein by reference in its entirety.

The polynucleotides can be obtained, and the nucleotide sequence of the polynucleotides determined, by any method known in the art. Nucleotide sequences encoding antibodies described herein, e.g., antibodies described in Tables 1-6, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17: 242-6, which is herein incorporated by reference in its entirety), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-PD-1 antibodies described herein can be readily isolated and sequenced using conventional procedures (e.g., by using oligonucleotide probes that are capable of binding specifically to genes encoding the heavy and light chains of the anti-PD-1 antibodies). Hybridoma cells can serve as a source of such DNA. Once isolated, the DNA can be placed into expression vectors, which are then transfected into host cells such as *E. coli* cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-PD-1 antibodies in the recombinant host cells.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable region, constant domains, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH domain and/or VL domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3, which is herein incorporated by reference in its entirety.

In certain aspects, provided herein are cells (e.g., host cells) expressing (e.g., recombinantly) antibodies described herein which specifically bind to PD-1 (e.g., human PD-1) and related polynucleotides and expression vectors. Provided herein are vectors (e.g., expression vectors) comprising polynucleotides comprising nucleotide sequences encoding anti-PD-1 antibodies or a fragment for recombinant expression in host cells, preferably in mammalian cells. Also provided herein are host cells comprising such vectors for recombinantly expressing anti-PD-1 antibodies described herein (e.g., human or humanized antibody). In a particular aspect, provided herein are methods for producing an antibody described herein, comprising expressing such antibody from a host cell.

Recombinant expression of an antibody described herein (e.g., a full-length antibody, heavy and/or light chain of an antibody, or a single chain antibody described herein) that specifically binds to PD-1 (e.g., human PD-1) involves construction of an expression vector containing a polynucleotide that encodes the antibody. Once a polynucleotide encoding an antibody molecule, heavy and/or light chain of an antibody, or a fragment thereof (e.g., heavy and/or light chain variable regions) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable region of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464, which are herein incorporated by reference in their entireties) and variable regions of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein or a fragment thereof. Thus, provided herein are host cells containing a polynucleotide encoding an antibody described herein or fragments thereof, or a heavy or light chain thereof, or fragment thereof, or a single chain antibody described herein, operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein, or a fragment thereof. In specific embodiments, a host cell contains two different vectors, a first vector comprising a polynucleotide encoding a heavy chain or a heavy chain variable region of an antibody described herein, or a fragment thereof, and a second vector comprising a polynucleotide encoding a light chain or a light chain variable region of an antibody described herein, or a fragment thereof. In other embodiments, a first host cell comprises a first vector comprising a polynucleotide encoding a heavy chain or a heavy chain variable region of an antibody described herein, or a fragment thereof, and a second host cell comprises a second vector comprising a polynucleotide encoding a light chain or a light chain variable region of an antibody described herein. In specific embodiments, a heavy chain/heavy chain variable region expressed by a first cell associated with a light chain/light chain variable region of a second cell to form an anti-PD-1 antibody described herein. In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-PD-1 antibody described herein, and a second vector comprising a polynucleotide encoding a heavy chain/heavy chain variable region of an anti-PD-1 antibody described herein.

A variety of host-expression vector systems can be utilized to express antibody molecules described herein (see, e.g., U.S. Pat. No. 5,807,715, which is herein incorporated by reference in its entirety). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein are CHO cells, for example CHO cells from the CHO GS System™ (Lonza). In a particular embodiment, cells for expressing antibodies described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking M K & Hofstetter H (1986) Gene 45: 101-5; and Cockett M I et al., (1990) Biotechnology 8(7): 662-7, each of which is herein incorporated by reference in its entirety). In certain embodiments, antibodies described herein are produced by CHO cells or NS0 cells. In a specific embodiment, the expression of nucleotide sequences encoding antibodies described herein which specifically bind PD-1 (e.g., human PD-1) is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2: 1791-1794), in which the antibody coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol Chem 24: 5503-5509); and the like, all of which are herein incorporated by reference in their entireties. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region El or E3) will result in a recombinant virus that is viable and capable of expressing the antibody molecule in infected hosts (e.g., see Logan J & Shenk T (1984) PNAS 81(12): 3655-9, which is herein incorporated by reference in its entirety). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol. 153: 516-544, which is herein incorporated by reference in its entirety).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, anti-PD-1 antibodies described herein are produced in mammalian cells, such as CHO cells.

In a specific embodiment, the antibodies described herein have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content.

For long-term, high-yield production of recombinant proteins, stable expression cells can be generated. For example, cell lines which stably express an anti-PD-1 antibody described herein can be engineered. In specific embodiments, a cell provided herein stably expresses a light chain/ light chain variable region and a heavy chain/heavy chain variable region which associate to form an antibody described herein.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-PD-1 antibody described herein or a fragment thereof. Such engineered cell lines can be particularly useful in screening and evaluation of compositions that interact directly or indirectly with the antibody molecule.

A number of selection systems can be used, including but not limited to the herpes simplex virus thymidine kinase (Wigler M et al., (1977) Cell 11(1): 223-32), hypoxanthineguanine phosphoribosyltransferase (Szybalska E H & Szybalski W (1962) PNAS 48(12): 2026-2034) and adenine phosphoribosyltransferase (Lowy I et al., (1980) Cell 22(3): 817-23) genes in tk-, hgprt- or aprt-cells, respectively, all of which are herein incorporated by reference in their entireties. Also, antimetabolite resistance can be used as the basis of selection for the following genes: dhfr, which confers resistance to methotrexate (Wigler M et al., (1980) PNAS 77(6): 3567-70; O'Hare K et al., (1981) PNAS 78: 1527-31); gpt, which confers resistance to mycophenolic acid (Mulligan R C & Berg P (1981) PNAS 78(4): 2072-6); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Felgner P L (1993) Trends Biotechnol 11(5): 211-5); and hygro, which confers resistance to hygromycin (Santerre R F et al., (1984) Gene 30(1-3): 147-56), all of which are herein incorporated by reference in their entireties. Methods commonly known in the art of recombinant DNA technology can be routinely applied to select the desired recombinant clone and such methods are described, for example, in Ausubel F M et al., (eds.), Current Protocols in Molecular Biology, John Wiley & Sons, N Y (1993); Kriegler M, Gene Transfer and Expression, A Laboratory Manual, Stockton Press, N Y (1990); and in Chapters 12 and 13, Dracopoli N C et al., (eds.), Current Protocols in Human Genetics, John Wiley & Sons, N Y (1994); Colbère-Garapin F et al., (1981) J Mol Biol 150: 1-14, which are incorporated by reference herein in their entireties.

The expression levels of an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987), which is herein incorporated by reference in its entirety). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse G F et al., (1983) Mol Cell Biol 3: 257-66, which is herein incorporated by reference in its entirety).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N J (1986) Nature 322: 562-565; and Köhler G (1980) PNAS 77: 2197-2199, each of which is herein incorporated by reference in its entirety). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

Antibodies or fragments thereof that specifically bind to PD-1 (e.g., human PD-1) can be produced by any method known in the art for the synthesis of antibodies, for example, by chemical synthesis or by recombinant expression techniques. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press, all of which are herein incorporated by reference in their entireties.

In a specific embodiment, an antibody described herein is an antibody (e.g., recombinant antibody) prepared, expressed, created or isolated by any means that involves creation, e.g., via synthesis, genetic engineering of DNA sequences. In certain embodiments, such antibody comprises sequences (e.g., DNA sequences or amino acid sequences) that do not naturally exist within the antibody germline repertoire of an animal or mammal (e.g., human) in vivo.

In one aspect, provided herein is a method of making an antibody which specifically binds to PD-1 (e.g., human PD-1) comprising culturing a cell or host cell described herein. Preferably, the method is performed in vitro. In a certain aspect, provided herein is a method of making an antibody which specifically binds to PD-1 (e.g., human PD-1) comprising expressing (e.g., recombinantly expressing) the antibody using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York, which is herein incorporated by reference in its entirety).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981), each of which is herein incorporated by reference in its entirety. The term "monoclonal antibody" as used herein is not limited to antibodies produced through hybridoma technology. For example, monoclonal antibodies can be produced recombinantly from host cells exogenously expressing an antibody described herein or a fragment thereof, for example, light chain and/or heavy chain of such antibody.

In specific embodiments, a "monoclonal antibody," as used herein, is an antibody produced by a single cell (e.g., hybridoma or host cell producing a recombinant antibody), wherein the antibody specifically binds to PD-1 (e.g., human PD-1) as determined, e.g., by ELISA or other antigen-binding or competitive binding assay known in the art or in the examples provided herein. In particular embodiments, a monoclonal antibody can be a chimeric antibody or a humanized antibody. In certain embodiments, a monoclonal antibody is a monovalent antibody or multivalent (e.g., bivalent) antibody. In particular embodiments, a monoclonal antibody is a monospecific or multispecific antibody (e.g., bispecific antibody). Monoclonal antibodies described herein can, for example, be made by the hybridoma method as described in Kohler G & Milstein C (1975) Nature 256: 495, which is herein incorporated by reference in its entirety, or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., PD-1 (e.g., human PD-1)) used for immunization. Alternatively, lymphocytes may be immunized in vitro. Lymphocytes then are fused with myeloma cells using a suitable fusing agent, such as polyethylene glycol, to form a hybridoma cell (Goding J W (Ed), Monoclonal Antibodies: Principles and Practice, pp. 59-103 (Academic Press, 1986), herein incorporated by reference in its entirety). Additionally, a RIMMS (repetitive immunization multiple sites) technique can be used to immunize an animal (Kilpatrick K E et al., (1997) Hybridoma 16:381-9, herein incorporated by reference in its entirety).

In some embodiments, mice (or other animals, such as rats, monkeys, donkeys, pigs, sheep, hamster, or dogs) can be immunized with an antigen (e.g., PD-1 (e.g., human PD-1)) and once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the American Type Culture Collection (ATCC®) (Manassas, Va.), to form hybridomas. Hybridomas are selected and cloned by limited dilution. In certain embodiments, lymph nodes of the immunized mice are harvested and fused with NS0 myeloma cells.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as NS0 cell line or those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor D (1984) J Immunol 133: 3001-5; Brodeur et al., Monoclonal Antibody Production Techniques and Applications, pp. 51-63 (Marcel Dekker, Inc., New York, 1987), each of which is herein incorporated by reference in its entirety).

Culture medium in which hybridoma cells are growing is assayed for production of monoclonal antibodies directed against PD-1 (e.g., human PD-1). The binding specificity of monoclonal antibodies produced by hybridoma cells is determined by methods known in the art, for example, immunoprecipitation or by an in vitro binding assay, such as radioimmunoassay (MA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding J W (Ed), Monoclonal Antibodies: Principles and Practice, supra). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein include antibody fragments which recognize specific PD-1 (e.g., human PD-1) and can be generated by any technique known to those of skill in the art. For example, Fab and $F(ab')_2$ fragments described herein can be produced by proteolytic cleavage of immunoglobulin molecules, using enzymes such as papain (to produce Fab fragments) or pepsin (to produce $F(ab')_2$ fragments). A Fab fragment corresponds to one of the two identical arms of an antibody molecule and contains the complete light chain paired with the VH and CH1 domains of the heavy chain. A $F(ab')_2$ fragment contains the two antigen-binding arms of an antibody molecule linked by disulfide bonds in the hinge region.

Further, the antibodies described herein can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in E. coli and the E. coli is infected with helper phage. Phage used in these methods are typically filamentous phage including fd and M13, and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108, all of which are herein incorporated by reference in their entireties.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce antibody fragments such as Fab, Fab' and F(ab')$_2$ fragments can also be employed using methods known in the art such as those disclosed in PCT publication No. WO 92/22324; Mullinax R L et al., (1992) BioTechniques 12(6): 864-9; Sawai H et al., (1995) Am J Reprod Immunol 34: 26-34; and Better M et al., (1988) Science 240: 1041-1043, all of which are herein incorporated by reference in their entireties.

In certain embodiments, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221; Gillies S D et al., (1989) J Immunol Methods 125: 191-202; and U.S. Pat. Nos. 5,807,715, 4,816,567, 4,816,397, and 6,331,415, all of which are herein incorporated by reference in their entireties.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including IgG$_1$, IgG$_2$, IgG$_3$ and IgG$_4$. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. No. 6,407,213, 5,766,886, International Publication No. WO 93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22; Sandhu J S (1994) Gene 150(2): 409-10 and Pedersen J T et al., (1994) J Mol Biol 235(3): 959-73, all of which are herein incorporated by reference in their entireties. See also U.S. Application Publication No. US 2005/0042664 A1 (Feb. 24, 2005), which is incorporated by reference herein in its entirety.

Methods for making multispecific (e.g., bispecific antibodies) have been described, see, for example, U.S. Pat. Nos. 7,951,917; 7,183,076; 8,227,577; 5,837,242; 5,989,830; 5,869,620; 6,132,992 and 8,586,713, all of which are herein incorporated by reference in their entireties.

Single domain antibodies, for example, antibodies lacking the light chains, can be produced by methods well known in the art. See Riechmann L & Muyldermans S (1999) J Immunol 231: 25-38; Nuttall S D et al., (2000) Curr Pharm Biotechnol 1(3): 253-263; Muyldermans S, (2001) J Biotechnol 74(4): 277-302; U.S. Pat. No. 6,005,079; and International Publication Nos. WO 94/04678, WO 94/25591 and WO 01/44301, all of which are herein incorporated by reference in their entireties.

Further, antibodies that specifically bind to a PD-1 antigen can, in turn, be utilized to generate anti-idiotype antibodies that "mimic" an antigen using techniques well known to those skilled in the art. See, e.g., Greenspan N S & Bona C A (1989) FASEB J 7(5): 437-444; and Nissinoff A (1991) J Immunol 147(8): 2429-2438, each of which is herein incorporated by reference in its entirety.

In particular embodiments, an antibody described herein, which binds to the same epitope of PD-1 (e.g., human PD-1) as an anti-PD-1 antibody described herein, is a human antibody. In particular embodiments, an antibody described herein, which competitively blocks (e.g., in a dose-dependent manner) any one of the antibodies described herein, from binding to PD-1 (e.g., human PD-1), is a human antibody. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the J$_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., PD-1). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg N & Huszar D (1995) Int Rev Immunol 13:65-93, herein incorporated by reference in its entirety. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569,825, 5,661,016, 5,545,806, 5,814,318 and 5,939,598, all of which are herein incorporated by reference in their entireties. Examples of mice capable of producing human antibodies include the Xenomouse™ (Abgenix, Inc.; U.S. Pat. Nos. 6,075,181 and 6,150,184), the HuAb-Mouse™ (Mederex, Inc./Gen Pharm; U.S. Pat. Nos. 5,545,806 and 5,569,825), the Trans Chromo Mouse™ (Kirin) and the KM Mouse™ (Medarex/Kirin), all of which are herein incorporated by reference in their entireties.

Human antibodies which specifically bind to PD-1 (e.g., human PD-1) can be made by a variety of methods known in the art including phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741, all of which are herein incorporated by reference in their entireties.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that specifically bind to a target antigen (e.g., PD-1 (e.g., human PD-1)). Such methods are known and are described in the art, see, e.g., Shinmoto H et al., (2004) Cytotechnology 46: 19-23; Naganawa Y et al., (2005) Human Antibodies 14: 27-31, each of which is herein incorporated by reference in its entirety.

5.6 Kits

Also provided, are kits comprising one or more antibodies described herein, or pharmaceutical composition or conjugates thereof. In a specific embodiment, provided herein is a pharmaceutical pack or kit comprising one or more containers filled with one or more of the ingredients of the pharmaceutical compositions described herein, such as one or more antibodies provided herein. In some embodiments, the kits contain a pharmaceutical composition described herein and any prophylactic or therapeutic agent, such as those described herein. In certain embodiments, the kits may contain a T cell mitogen, such as, e.g., phytohaemagglutinin (PHA) and/or phorbol myristate acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided, are kits that can be used in the above methods. In one embodiment, a kit comprises an antibody described herein, preferably a purified antibody, in one or more containers. In a specific embodiment, kits described herein contain a substantially isolated PD-1 antigen (e.g., human PD-1) as a control. In another specific embodiment, the kits described herein further comprise a control antibody which does not react with a PD-1 antigen. In another specific embodiment, kits described herein contain one or more elements for detecting the binding of an antibody to a PD-1 antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized PD-1 antigen. The PD-1 antigen provided in the kit can also be attached to a solid support. In a more specific embodiment, the detecting means of the above described kit includes a solid support to which a PD-1 antigen is attached. Such a kit can also include a non-attached reporter-labeled anti-human antibody or anti-mouse/rat antibody. In this embodiment, binding of the antibody to the PD-1 antigen can be detected by binding of the said reporter-labeled antibody. In one embodiment, the present invention relates to the use of a kit of the present invention for in vitro assaying and/or detecting PD-1 antigen (e.g., human PD-1) in a biological sample.

6. EXAMPLES

The examples in this Section (i.e., Section 6) are offered by way of illustration, and not by way of limitation.

6.1 Example 1: Characterization of Anti-PD-1 Antibodies

This example describes the characterization of antibodies that specifically bind to human PD-1, in particular, antibodies designated AGEN2033w, AGEN2034w, AGEN2046w, and AGEN2047w. AGEN2033w and AGEN2046w share the same heavy chain variable region amino acid sequence (SEQ ID NO: 15) and the same light chain variable region amino acid sequence (SEQ ID NO: 16). AGEN2034w and AGEN2047w share the same heavy chain variable region amino acid sequence (SEQ ID NO: 17) and the same light chain variable region amino acid sequence (SEQ ID NO: 16). AGEN2033w and AGEN2034w are human IgG$_4$ antibodies containing an S228P mutation (i.e., substitution of serine with proline at position 228 relative to the wild type IgG$_4$ constant region) according to the EU numbering system, whereas AGEN2046w and AGEN2047w are human IgG$_1$ antibodies. In addition, three Fc mutants of AGEN2047w were also characterized: an N297A mutant, an S267E/L328F double mutant, and an S239D/A330L/I332E triple mutant, numbered according to the EU numbering system.

6.1.1 Antibody Binding to PD-1 Expressed by Activated T Cells

The anti-PD-1 antibodies AGEN2046w, AGEN2047w, and AGEN2034w were examined for binding to activated peripheral blood mononuclear cells (PBMCs) by flow cytometry. Cryopreserved human PBMCs prepared from unpurified buffy coats (Research Blood Components, Catalog number (Cat#) 002) or cryopreserved cynomolgus PBMCs (Worldwide Primates Inc., customer order) were plated at 10$^5$ cells/well in RPMI1640 medium supplemented with Normocin™ (InvivoGen, Cat# ant-nr-1) and 10% heat-inactivated FBS (Gibco, Cat#16140063) in 96-well NUN-CLON delta surface plates (NUNC™). The cells were cultured in the presence of 100 ng/ml of Staphylococcus Enterotoxin A (SEA; for human PBMCs) (Toxin Technologies, Cat# at101red) or Staphylococcus Enterotoxin B (SEB; for cynomolgus PBMCs) (Toxin Technology, Cat# bt202red) for 5 days at 37° C., 5% $CO_2$, and 97% humidity. The cells were then washed once with sample buffer (PBS+ 2% FBS+0.09% sodium azide) and incubated in the dark on ice with 100 µl of serially diluted antibodies or isotype controls (10, 1, 0.1, 0.01, 0.001, and 0.0001 µg/ml of AGEN2046w, AGEN2047w, or human $IgG_1$ isotype control (LifeTein LLC, Cat# LT12031); or 25, 5, 1, 0.2, 0.04, 0.008, 0.0016, 0.00032, and 0.000064 µg/ml of AGEN2034w or human $IgG_4$ isotype control (LifeTein LLC, Cat# LT12034)). After 45 minutes, the cells were washed twice with sample buffer and then incubated with LIVE/DEAD® Fixable Near-IR Dead Cell Stain (Life Technologies, Cat# L10119), CD4-BV421 (Biolegend, Cat#317434), and goat $F(ab')_2$ anti-human IgG+A+M, R-PE (Life Technologies, Cat# AHI1707) for 30 minutes. The cells were washed twice with sample buffer and then resuspended in sample buffer and analyzed with a FACS Fortessa cytometer (Becton Dickinson). CD4+ T cells were gated and the mean fluorescence intensity (MFI) was recorded.

The anti-PD-1 antibodies AGEN2046w and AGEN2047w bound to activated human CD4+ T cells (FIG. 1A). AGEN2034w bound to activated human and cynomolgus CD4+ T cells (FIGS. 1B and 1C).

The binding of AGEN2034w to activated primary human T cells was measured again in a similar assay. Briefly, human PBMCs were cultured in the presence of 100 ng/ml of the SEA peptide for 5 days and then stained with serially diluted (50, 10, 2, 0.4, 0.080, 0.016, 0.0032, 0.00064, 0.000128, 0.0000256, 0.00000512, and 0.000001024 µg/ml) AGEN2034w or a human $IgG_4$ isotype control. Cells were analyzed with a FACS Fortessa cytometer (Becton Dickinson). CD4+ T cells were gated and the mean fluorescence intensity (MFI) of AGEN2034w-positive cells was determined.

Figure 1D:
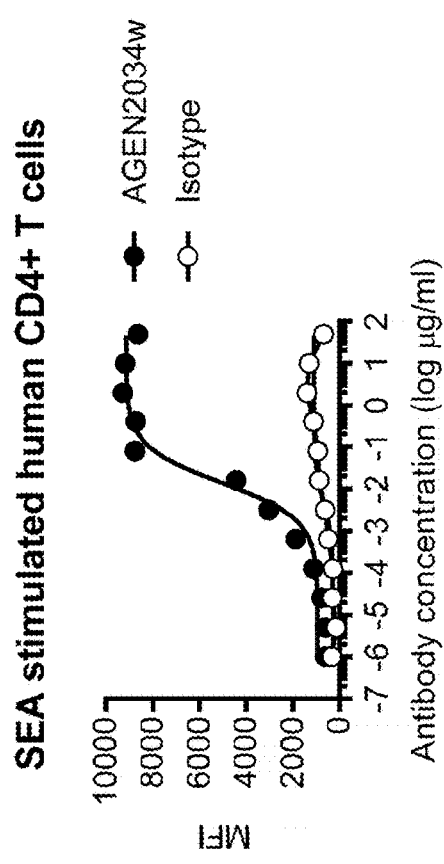

As shown in FIG. 1D, AGEN2034w bound to activated primary human CD4+ T cells.

6.1.2 PD-1 Antibody Selectivity Assay

The selectivity of AGEN2034w for PD-1 was assessed against homologous proteins using suspension array technology.

Based on their amino acid sequence homology with PD-1, Ig superfamily proteins roundabout homolog 2 (ROBO2), B7 homolog 7 (B7-H7), and signal regulatory protein gamma (SIRPγ) were selected for evaluation of binding by AGEN0234w using a suspension array assay. ROBO2, B7-H7 and SIRPγ were identified as homologs of PD-1 by protein alignment applying Basic Local Alignment Search Tool (BLAST; NCBI). The sequence homology of human PD-1 to its homologs was as follows: human PD-1 versus (vs) human ROBO2: 27.9%; human PD-1 vs human SIRPγ (SIRPG_HUMAN): 24.8%; and human PD-1 vs human B7-H7: 22.6%.

Recombinant proteins, human ROBO2-Fc chimera (R&D systems, Cat#3147-RB-050), human B7-H7-Fc chimera (R&D systems, Cat#8084-B7-050), human SIRPγ-His chimera (Sino Biologicals, Cat#11828-H08H), and human PD-1-Fc chimera (R&D systems, Cat#1086-PD) were coupled to Luminex® microspheres (Luminex Corp, Cat# LC10005-01, LC10022-01, LC10046-01, LC10048-01, and LC10059-01) using N-hydroxysuccinimide (NHS) ester chemistry and incubated with a dose titration (7.5, 2.5, 0.833, 0.277, 0.0926, 0.0.0309, 0.0103, 0.0034, 0.0011, 0.0004, 0.0001, and 0.00004 µg/ml) of AGEN2034w. An anti-human IgG antibody labeled with phycoerythrin (PE) was then added to detect AGEN2034w. Binding was assessed by a Luminex® 200 detection system.

The antibody AGEN2034w showed specific binding to human PD-1, and no significant binding to ROBO2, B7-H7, or SIRPγ was observed at tested concentrations (FIG. 2).

6.1.3 Ligand Blocking Activity Determined by Suspension Array Technology

To determine whether anti-PD-1 antibodies block binding of ligands PD-L1 and PD-L2, a ranking assay setup was performed using suspension array technology. 1200 Luminex® beads in 5 µl assay buffer (Luminex Corp, Cat#48 LC10014-48) were added to each well of 96-well half area plates (Corning, Inc., Cat#3884). The beads were coupled with PD-1 antigen PD-1-Fc chimera (R&D systems, Cat#1086-PD) via amine coupling with COOH bead surface. The coupling reaction was performed using 50 µg/ml of PD-1 antigen and $1 \times 10^7$ Luminex beads per ml. Standard NHS ester chemistry was used to form carbodiimide bonds between the primary amine groups of the antigen and the carboxyl groups on the bead surface (Luminex Xmap cookbook chapter 3).

Antigen coupling for proteins is a simple two-step carbodiimide procedure during which microsphere carboxyl groups are first activated with EDC (1-Ethyl-3-[3-dimethylaminopropyl]carbodiimide hydrochloride) reagent in the presence of Sulfo-NHS (N-hydroxysulfosuccinimide) to form a sulfo-NHS-ester intermediate. The reactive intermediate is then replaced by reaction with the primary amine of the target molecule (antibody, protein or peptide) to form a covalent amide bond. The coupled beads were incubated with different concentrations of anti-PD-1 antibodies in triplicates (final concentrations from 7.5 µg/ml to 0.01 µg/ml per well) for 1 hour at 20° C. and 650 rpm. The antibodies tested were AGEN2033w, AGEN2034w, AGEN2046w, and AGEN2047w, an $IgG_1$ isotype control, and an $IgG_4$ isotype control. Subsequently, 30 µl of R-PE labeled PD-L1-Fc (R&D Systems, Cat#156-B7) or PD-L2-Fc (R&D Systems, Cat#1224-PL) at a concentration of 1 nM was added to each well, giving a total well volume of 60 µl (1200 beads per well and a final concentration of 0.5 nM of labeled PD-L1 or PD-L2). The labeling of the ligand was conducted using R-PE labeling kits (AbDSerotec, LYNX Rapid RPE Antibody Conjugation Kit, Cat# LNK023RPE) according to the manufacturer's protocol. Plates were analyzed using a Luminex® 200 system (Millipore). 100 beads were counted per well in 50 µl sample volume. Ligand blocking potential was calculated using the MFI values of the non-competed signal (100% binding) of the ligand only control. A PE detectable signal indicated ligand binding to the antigen.

All of the anti-PD-1 antibodies tested inhibited binding of PD-L1 and PD-L2 to PD-1 (FIGS. 3A-3D).

The measurement of the ligand blocking activity of AGEN2034w was repeated in a similar assay. Briefly, recombinant PD-1-Fc chimera (R&D systems, Cat#1086-PD) was coupled to Luminex® microspheres (Luminex Corp, Cat# LC10048-01) using N-hydroxysuccinimide (NHS) ester chemistry. The PD-1-coupled beads were incubated with a dose titration ($4.0 \times 10^{-5}$–7.5 µg/ml) of AGEN2034w or an isotype control antibody, followed by incubation of fluorescently labeled PD-L1-Fc (R&D Systems, Cat#156-B7) or PD-L2-Fc (R&D Systems, Cat#1224-PL). Subsequently, binding of PD-L1 or PD-L2 to the PD-1-coupled beads was assessed using a Luminex® 200 detection system and the median fluorescent intensity (MFI) was recorded.

The antibody AGEN2034w effectively blocked engagement of PD-1 with its ligands, PD-L1 (FIG. 3E) and PD-L2 (FIG. 3F).

6.1.4 Effect of Anti-PD-1 Antibodies on Human PBMCs Following Staphylococcus Enterotoxin A (SEA) Stimulation The functional activity of anti-PD-1 antibodies on primary human T cells was assessed following SEA stimulation. Cryopreserved human PBMCs prepared from unpurified buffy coats (Research Blood Components, Cat#002) were plated at $10^5$ cells/well in RPMI1640 medium supplemented with Normocin™ (InvivoGen, Cat# ant-nr-1) and 10% heat-inactivated FBS (Gibco, Cat#16140063) in 96-well NUNCLON delta surface plates (NUNC™). The cells were cultured in the presence of a fixed concentration (10 μg/ml) or dose-range amounts of antibodies (50, 10, 2, 0.4, 0.08, 0.016, and 0.0032 μg/ml) and a fixed amount of SEA (100 ng/ml, Toxin Technology, Cat# at101red) for 5 days at 37° C., 5% $CO_2$, and 97% humidity. The antibodies tested were AGEN2033w, AGEN2034w, AGEN2046w, AGEN2047w, and an $IgG_1$ isotype control. Supernatant was collected and stored at −80° C. until analysis. The titers of IL-2 were measured by electrochemiluminescence (MSD).

As shown in FIGS. 4A and 4B, the anti-PD-1 antibodies AGEN2033w, AGEN2034w, AGEN2046w, and AGEN2047w increased IL-2 production of PBMCs relative to isotype control in the presence of SEA stimulation.

Further, the antagonistic activity of AGEN2034w was examined either alone or in combination with anti-CTLA-4, anti-TIGIT, anti-CD137, or anti-OX40 antibodies in the primary PBMC assay described above. Briefly, cryopreserved human PBMCs prepared from unpurified buffy coats (Research Blood Components, Cat #002) were cultured with the SEA superantigen (Toxin Technology, Cat# at101red) (100 ng/ml in FIGS. 4C, 4D, and 4F; 200 ng/ml in FIG. 4E) and AGEN2034w (10 μg/ml in FIGS. 4C and 4E; 5 μg/ml in FIG. 4D; a dose range of 12, 6, 3, 0.3, 0.03, 0.003, 0.0003, and 0.0001 μg/ml in FIG. 4F) or an isotype control antibody in the presence or absence of 5 μg/ml of anti-CTLA-4 antibody Ipilimumab (Myoderm) (FIG. 4C), 10 μg/ml of anti-TIGIT antibody pab2197 or pab2196 (FIG. 4D), 5 μg/ml of anti-CD137 antibody pab2225 (FIG. 4E), or a dose range (12, 6, 3, 0.3, 0.03, 0.003, 0.0003, and 0.0001 μg/ml) of anti-OX40 antibody pab1928 for 5 days. Supernatants were collected and titers of IL-2 were measured using AlphaLISA (Perkin Elmer, Cat# AL221C). Anti-TIGIT antibodies pab2197 and pab2196 were generated based on the variable region sequences of antibodies 10A7 and 1F4, respectively, provided in U.S. Application Publication No. US2013/0251720 (herein incorporated by reference in its entirety). Anti-CD137 antibody pab2225 was generated based on the variable region sequences of antibody 20H4 provided in U.S. Pat. No. 8,137,667 (herein incorporated by reference in its entirety). Anti-OX40 antibody pab1928 was generated based on the variable region sequences of antibody Hu106-122 provided in U.S. Patent Publication No. US 2013/0280275 (herein incorporated by reference in its entirety). The sequences of the anti-TIGIT, anti-CD137, and anti-OX40 antibodies are listed in Table 8.

TABLE 8

Sequences of anti-TIGIT, anti-CD137, and anti-OX40 antibodies

| SEQ ID NO: | Description | Amino acid sequence |
| --- | --- | --- |
| 66 | pab2197 heavy chain | EVQLVESGGGLTQPGKSLKLSCEASGFTFSSFTMHWVRQSPGKGLE WVAPIRSGSGIVFYADAVRGRFTISRDNAKNLLFLQMNDLKSEDTA MYYCARRPLGHNTFDSWGQGTLVTVSSASTKGPSVFPLAPSSKSTS GGTAALGCLVKDYFPEPVTVSWNSGALTSGVHTFPAVLQSSGLYSL SSVVTVPSSSLGTQTYICNVNHKPSNTKVDKRVEPKSCDKTHTCPP CPAPELLGGPSVFLFPPKPKDTLMISRTPEVTCVVVDVSHEDPEVK FNWYVDGVEVHNAKTKPREEQYNSTYRVVSVLTVLHQDWLNGKEYK CKVSNKALPAPIEKTISKAKGQPREPQVYTLPPSREEMTKNQVSLT CLVKGFYPSDIAVEWESNGQPENNYKTTPPVLDSDGSFFLYSKLTV DKSRWQQGNVFSCSVMHEALHNHYTQKSLSLSPG |
| 67 | pab2197 light chain | DIVMTQSPSSLAVSPGEKVTMTCKSSQSLYYSGVKENLLAWYQQKP GQSPKLLIYYASIRFTGVPDRFTGSGSGTDYTLTITSVQAEDMGQY FCQQGINNPLTFGDGTKLEIKRTVAAPSVFIFPPSDEQLKSGTASV VCLLNNFYPREAKVQWKVDNALQSGNSQESVTEQDSKDSTYSLSST LTLSKADYEKHKVYACEVTHQGLSSPVTKSFNRGEC |
| 68 | pab2196 heavy chain | EVQLQQSGPELVKPGTSMKISCKASGYSFTGHLMNWVKQSHGKNLE WIGLIIPYNGGTSYNQKFKGKATLTVDKSSSTAYMELLSLTSDDSA VYFCSRGLRGFYAMDYWGQGTSVTVSSASTKGPSVFPLAPSSKSTS GGTAALGCLVKDYFPEPVTVSWNSGALTSGVHTFPAVLQSSGLYSL SSVVTVPSSSLGTQTYICNVNHKPSNTKVDKRVEPKSCDKTHTCPP CPAPELLGGPSVFLFPPKPKDTLMISRTPEVTCVVVDVSHEDPEVK FNWYVDGVEVHNAKTKPREEQYNSTYRVVSVLTVLHQDWLNGKEYK CKVSNKALPAPIEKTISKAKGQPREPQVYTLPPSREEMTKNQVSLT CLVKGFYPSDIAVEWESNGQPENNYKTTPPVLDSDGSFFLYSKLTV DKSRWQQGNVFSCSVMHEALHNHYTQKSLSLSPG |
| 69 | pab2196 light chain | DVVLTQTPLSLSVSFGDQVSISCRSSQSLVNSYGNTFLSWYLHKPG QSPQLLIFGISNRFSGVPDRFSGSGSGTDFTLKISTIKPEDLGMYY CLQGTHQPPTFGPGTKLEVKRTVAAPSVFIFPPSDEQLKSGTASVV CLLNNFYPREAKVQWKVDNALQSGNSQESVTEQDSKDSTYSLSSTL TLSKADYEKHKVYACEVTHQGLSSPVTKSFNRGEC |
| 70 | pab2225 heavy chain | QVQLQQWGAGLLKPSETLSLTCAVYGGSFSGYYWSWIRQSPEKGLE WIGEINHGGYVTYNPSLESRVTISVDTSKNQFSLKLSSVTAADTAV YYCARDYGPGNYDWYFDLWGRGTLVTVSSASTKGPSVFPLAPSSKS TSGGTAALGCLVKDYFPEPVTVSWNSGALTSGVHTFPAVLQSSGLY SLSSVVTVPSSSLGTQTYICNVNHKPSNTKVDKRVEPKSCDKTHTC |

TABLE 8-continued

Sequences of anti-TIGIT, anti-CD137, and anti-OX40 antibodies

| SEQ ID NO: | Description | Amino acid sequence |
|---|---|---|
| | | PPCPAPELLGGPSVFLFPPKPKDTLMISRTPEVTCVVVDVSHEDPE VKFNWYVDGVEVHNAKTKPREEQYNSTYRVVSVLTVLHQDWLNGKE YKCKVSNKALPAPIEKTISKAKGQPREPQVYTLPPSREEMTKNQVS LTCLVKGFYPSDIAVEWESNGQPENNYKTTPPVLDSDGSFFLYSKL TVDKSRWQQGNVFSCSVMHEALHNHYTQKSLSLSPG |
| 71 | pab2225 light chain | EIVLTQSPATLSLSPGERATLSCRASQSVSSYLAWYQQKPGQAPRL LIYDASNRATGIPARFSGSGSGTDFTLTISSLEPEDFAVYYCQQRS NWPPALTFGGGTKVEIKRTVAAPSVFIFPPSDEQLKSGTASVVCLL NNFYPREAKVQWKVDNALQSGNSQESVTEQDSKDSTYSLSSTLTLS KADYEKHKVYACEVTHQGLSSPVTKSFNRGEC |
| 72 | pab1928 heavy chain | QVQLVQSGSELKKPGASVKVSCKASGYTFTDYSMHWVRQAPGQGLK WMGWINTETGEPTYADDFKGRFVFSLDTSVSTAYLQISSLKAEDTA VYYCANPYYDYVSYYAMDYWGQGTTVTVSSASTKGPSVFPLAPSSK STSGGTAALGCLVKDYFPEPVTVSWNSGALTSGVHTFPAVLQSSGL YSLSSVVTVPSSSLGTQTYICNVNHKPSNTKVDKRVEPKSCDKTHT CPPCPAPELLGGPSVFLFPPKPKDTLMISRTPEVTCVVVDVSHEDP EVKFNWYVDGVEVHNAKTKPREEQYNSTYRVVSVLTVLHQDWLNGK EYKCKVSNKALPAPIEKTISKAKGQPREPQVYTLPPSREEMTKNQV SLTCLVKGFYPSDIAVEWESNGQPENNYKTTPPVLDSDGSFFLYSK LTVDKSRWQQGNVFSCSVMHEALHNHYTQKSLSLSPG |
| 73 | pab 1928 light chain | DIQMTQSPSSLSASVGDRVTITCKASQDVSTAVAWYQQKPGKAPKL LIYSASYLYTGVPSRFSGSGSGTDFTFTISSLQPEDIATYYCQQHY STPRTFGQGTKLEIKRSVAAPSVFIFPPSDEQLKSGTASVVCLLNN FYPREAKVQWKVDNALQSGNSQESVTEQDSKDSTYSLSSTLTLSKA DYEKHKVYACEVTHQGLSSPVTKSFNRGEC |

The anti-PD-1 antibody AGEN2034w, either alone or in combination with anti-CTLA-4 antibody Ipilimumab (FIG. 4C), anti-TIGIT antibody pab2197 or pab2196 (FIG. 4D), anti-CD137 antibody pab2225 (FIG. 4E), or anti-OX40 antibody pab1928 (FIG. 4F), enhanced IL-2 production in human PBMCs in the presence of the SEA superantigen.

6.1.5 Effect of Fc Gamma Receptor Binding on the Antagonistic Activity of Anti-PD-1 Antibodies In this example, the effect of FcγR binding on the antagonistic activity of anti-PD-1 antibodies was examined.

First, the antagonistic activity of an anti-PD-1 reference antibody was examined in the presence or absence of FcγR blockers. Cryopreserved human PBMCs prepared from unpurified buffy coats (Research Blood Components, Cat#002) were plated at $10^5$ cells/well in RPMI1640 medium supplemented with Normocin™ (InvivoGen, Cat# ant-nr-1) and 10% heat-inactivated FBS (Gibco, Cat#16140063) in 96-well NUNCLON delta surface plates (NUNC™). The cells were cultured with 100 ng/ml of SEA peptide (Toxin Technology, Cat# at101red) and 10 μg/ml of an anti-PD-1 reference antibody or isotype control in the presence or absence of a fixed concentration of an Fc receptor blocking cocktail containing anti-CD16 antibody (1 μg/ml, R&D systems, Cat# AF1330) and irrelevant IgG$_1$ (25 μg/ml, LifeTein, Cat# LT12031) for 5 days at 37° C., 5% $CO_2$, and 97% humidity. Supernatant was collected and stored at −80° C. until analysis. The titers of IL-2 were measured by electrochemiluminescence (MSD).

FcγR blockade using an anti-CD16 antibody enhanced the ability of the anti-PD-1 reference antibody to induce IL-2 secretion in this primary human PBMC assay (FIG. 5A).

A similar study was conducted to examine the impact of FcγR blockade on the antagonistic activity of AGEN2034w. Briefly, human PBMCs were cultured with 100 ng/ml of SEA peptide (Toxin Technology, Cat# at101red), 10 μg/ml of AGEN2034w or an isotype control antibody (HEL IgG$_1$, LifeTein, Cat# LT12031), and 20 μg/ml of an anti-CD16 antibody (Biolegend, Cat#302013), an anti-CD32 antibody (eBioscience, Cat#16-0329-81) which binds to both CD32A and CD32B, an anti-CD64 antibody (Biolegend, Cat#305016), or an isotype control (Biolegend, Cat#400543) for 5 days at 37° C., 5% $CO_2$, and 97% humidity. Supernatants were collected and stored at −80° C. until analysis. The titers of IL-2 were measured by electrochemiluminescence (MSD).

Consistent with the result in FIG. 5A, FcγR blockade using an anti-CD16 antibody, anti-CD32 antibody, or anti-CD64 antibody, increased IL-2 secretion induced by AGEN2034w in this human PBMC assay (FIG. 5B).

Next, three IgG$_1$ Fc mutants of AGEN2047w (an N297A mutant, an S267E/L328F double mutant, and an S239D/A330L/I332E triple mutant, numbered according to the EU numbering system) were generated and compared against AGEN2047w, which comprises a wild type IgG$_1$ constant region, in the human PBMC SEA assay described above. Briefly, cryopreserved human PBMCs were incubated with 100 ng/ml of SEA and 10 μg/ml of anti-PD-1 antibodies AGEN2047w, AGEN2047w-N297A, AGEN2047w-S267E/L328F, AGEN2047w-S239D/A330L/I332E, or isotype control antibodies with respective wild type or mutant Fc regions.

As shown in FIG. 5C, the N297A mutant with diminished FcγR binding further enhanced IL-2 secretion. In contrast, the S267E/L328F double mutant and the S239D/A330L/I332E triple mutant, both of which have enhanced FcγR binding, induced less IL-2 production than that of wild type AGEN2047w.

6.1.6 Effect of Anti-PD-1 Antibody in Mixed Lymphocyte Reaction

Next, the anti-PD-1 antibody AGEN2034w was examined in a mixed lymphocyte reaction. Dendritic cells were derived from isolated CD14+ cells (Stemcell Technologies, Cat#18058) obtained from cryopreserved HLA-A2+ human PBMCs and differentiated first in the presence of 500 U/ml IL-4 (Peprotech, Cat#200-04-20UG) and 1000 U/ml GM-CSF (Peprotech, Cat#300-03-20UG) for 24 hours, and then in the presence of 1000 U/ml TNFα (Peprotech, Cat#300-01A-50UG), 10 ng/ml IL-10 (Peprotech, Cat#200-01B-10UG), 10 ng/ml IL-6 (Peprotech, Cat#200-06-20UG), and 1 μM PGE2 (Sigma, Cat# P0409-5MG) for additional 24 hours. 50,000 pan T cells purified from an allogeneic HLA-A2-human PBMC donor by MACS column purification (Miltenyi Biotec, Cat#130-096-535) were co-cultured with 10,000 dendritic cells in the absence of any antibody or in the presence of 10 μg/ml human IgG$_4$ isotype control antibody (Biolegend, Cat#403402) or 10 μg/ml AGEN2034w in RPMI (Corning, Cat#10-040-CM) containing 5% human AB sera (Corning, Cat#35-060-CI) and Penicillin/Streptomycin (Gibco, Cat#15140-122). Cultures were incubated for 5 days at 37° C. and 5% $CO_2$. Supernatant was assessed for steady-state concentrations of IFNγ using AlphaLISA (Perkin Elmer, Cat# AL217C).

As shown in FIG. 6, AGEN2034w induced IFNγ production in the co-culture of purified human T cells and in vitro-derived allogeneic dendritic cells.

6.1.7 Effect of Anti-PD-1 Antibody in an Ascites Fluid Suppression Assay

In this example, the anti-PD-1 antibody AGEN2034w was examined for its ability to relieve suppression of T cell proliferation induced by ovarian cancer ascites fluid. Briefly, primary human PBMCs were labeled with CFSE (Biolegend, Cat#423801) and then stimulated with 1 μg/ml anti-CD3 antibody (eBioscience, Cat#16-0037-85) and 50% volume/volume of ovarian cancer ascites fluid in the presence of increasing concentrations (0.00000102-50 μg/ml) of AGEN2034w or an IgG$_4$ isotype control antibody (Biolegend, Cat#317434) for 4 to 5 days. The cells were immunostained with anti-human CD4 antibody (Biolegend, Cat#317434) or anti-human CD8 antibody (Biolegend, Cat#344710) and LIVE-DEAD viability stain (Life Technologies, Cat# L10119). Proliferation of CD4+ or CD8+ T cells, as illustrated by CFSE dilution, was measured by flow cytometry using BD Fortessa (Becton Dickinson).

As shown in FIGS. 7A-7C, co-culture with ovarian cancer ascites fluid reduced proliferation of anti-CD3-antibody-stimulated T cells and this reduction could be partially relieved by the anti-PD-1 antibody AGEN2034w.

6.1.8 Effect of Anti-PD-1 Antibody in a Jurkat NFAT-Luciferase Reporter Assay

Further, a reporter assay was utilized to probe the antagonistic activity of AGEN2034w. Specifically, in this reporter assay, co-culture of PD-L1-expressing target cells and PD-1-expressing reporter cells inhibited expression of a NFAT-luciferase reporter gene in the reporter cells. Blockade of PD-1/PD-L1 interaction by an anti-PD-1 antibody could relieve the inhibitory signal, leading to luciferase expression.

Briefly, PD-L1+ CHOK1 target cells (Promega, Cat# CS187108) were co-cultured with GloResponse™ NFAT-luc2/PD-1 Jurkat reporter cells (Promega, Cat# CS187102) in the presence of increasing concentrations (0-50 μg/ml) of AGEN2034w or an isotype control antibody in RPMI-1640 medium (Corning, Cat#21-040-CV) supplemented with 2% heat-inactivated FBS (Gemini, Cat#100-106). After 6 hours of incubation, the efficacy of AGEN2034w to relieve suppression of the reporter gene induced by PD-L1 binding to PD-1 was determined by measuring luciferase using Bio-Glo™ Luciferase Assay System (Promega, Cat# G7941).

As shown in FIG. 8, the anti-PD-1 antibody AGEN2034w enhanced TCR signaling in a dose-dependent manner in this Jurkat NFAT-luciferase reporter assay.

6.2 Example 2: Characterization of Additional Anti-PD-1 Antibodies

In this example, the following six additional anti-PD-1 antibodies were characterized: AGEN2001w, AGEN2002w, EP11_pl1_B03, EP11_pl1_B05, EP11_pl1_C02, and EP11_pl1_C03. The variable heavy chain and variable light chain sequences of these antibodies are disclosed in Table 6.

6.2.1 Binding and Ligand Blocking Analysis of Anti-PD-1 Antibodies

The affinity of the six anti-PD-1 antibodies described above was analyzed by surface plasmon resonance. All six antibodies bound to recombinant human PD-1 (data not shown).

The ligand blocking activity of the six anti-PD-1 antibodies was examined using suspension array technology in an assay similar to the one described in Section 6.1.3. The coupled beads were incubated with different concentrations of anti-PD-1 antibodies in duplicates (final concentrations from 7.5 μg/ml to 0.01 μg/ml per well) for 1 hour at 20° C. and 650 rpm. R-PE labeled PD-L1-Fc (R&D Systems, Cat#156-B7) or PD-L2-Fc (R&D Systems, Cat#1224-PL) was then added. The anti-PD-1 antibodies tested were AGEN2001w, AGEN2002w, EP11_pl1_B03, EP11_pl1_B05, EP11_pl1_C02, and EP11_pl1_C03. As shown in FIGS. 9A-9F, all of the anti-PD-1 antibodies tested blocked binding of PD-1 to PD-L1 and PD-L2 in a dose-dependent manner.

6.2.2 Effect of Anti-PD-1 Antibody on Human PBMCs Following Staphylococcus Enterotoxin A (SEA) Stimulation The functional activity of the anti-PD-1 antibody AGEN2002w on human PBMCs was tested in an assay similar to the one described in Section 6.1.4. Briefly, cryopreserved human PBMCs prepared from unpurified buffy coats (Research Blood Components, Cat#002) were cultured in the presence of 10 μg/ml of the anti-PD-1 antibody AGEN2002w or an isotype control antibody (HEL IgG$_1$, LifeTein, Cat# LT12031) and 100 ng/ml of SEA peptide (Toxin Technologies, Cat# at101red) for 4 days at 37° C., 5% $CO_2$, and 97% humidity. Supernatant was collected and stored at −80° C. until analysis. The titers of IL-2 were measured by electrochemiluminescence (MSD).

As shown in FIG. 10, the anti-PD-1 antibody AGEN2002w increased IL-2 production of primary human PBMCs in the presence of SEA stimulation.

6.3 Example 3: Epitope Mapping of Anti-PD-1 Antibody

The epitope of anti-PD-1 antibody AGEN2034w was characterized using hydrogen-deuterium exchange (HDX) mass spectrometry and a Pepscan analysis.

6.3.1 Epitope Mapping of Anti-PD-1 Fab Using Hydrogen-Deuterium Exchange (HDX) Mass Spectrometry The interaction of a Fab fragment of AGEN2034w (AGEN2034w-Fab) with the extracellular domain of human PD-1 was studied by hydrogen-deuterium exchange (HDX) mass spectrometry.

Recombinant His-tagged human PD-1 was obtained from Sino Biological Inc (Cat#10377-H08H). When used, deglycosylated PD-1 was prepared from 300 μs of recombinant His-tagged human PD-1 protein incubated with 6 μl of PNGase F at 37° C. for 4 hours. Fab fragment of anti-PD-1 antibody was prepared from AGEN2034w by protease treatment.

For pepsin/protease XVIII digestion, 4.0 μg of native or deglycosylated human PD-1 in 125 μl control buffer (50 mM phosphate, 100 mM sodium chloride at pH 7.4) was denatured by adding 135 µl of 4 M guanidine hydrochloride, 0.85 M TCEP buffer (final pH is 2.5), and incubating the mixture for 3 minutes at 11° C. Then, the mixture was subjected to on-column pepsin/protease XVIII digestion using an in-house packed pepsin/protease XVIII column and the resultant peptides were analyzed using a UPLC-MS system comprised of a Waters Acquity UPLC coupled to a Q Exactive™ Hybrid Quadrupole-Orbitrap Mass Spectrometer (Thermo). The peptides were separated on a 50 mm×1 mm C8 column with a 19 min gradient from 2-27% solvent B (0.2% formic acid in acetonitrile). Peptide identification was done through searching MS/MS data against the human PD-1 sequence with Mascot. The mass tolerance for the precursor and product ions was 10 ppm and 0.05 Da, respectively.

10 µl human PD-1 (4.0 µg) or 10 µl human PD-1 and Fab mixture (4.0 µg: 4.0 µg) was incubated with 125 µl deuterium oxide labeling buffer (50 mM sodium phosphate, 100 mM sodium chloride at pD 7.4) for 0 second, 60 seconds, 600 seconds, and 3600 seconds at 11° C. Hydrogen/deuterium exchange was quenched by adding 135 µl of 4 M guanidine hydrochloride, 0.85 M TCEP buffer (final pH is 2.5). Subsequently, the quenched samples were subjected to on column pepsin/protease XVIII digestion and LC-MS analysis as described above. The mass spectra were recorded in MS only mode.

Raw MS data was processed using HDX WorkBench, software for the analysis of H/D exchange MS data (J. Am. Soc. Mass Spectrom. 2012, 23 (9), 1512-1521, incorporated herein by reference in its entirety). The deuterium levels were calculated using the average mass difference between the deuteriated peptide and its native form ($t_0$).

Sequence coverage of 85.4% was achieved for deglycosylated human PD-1 without His-tag. Most PD-1 peptides displayed identical or similar deuterium levels with and without the anti-human PD-1 Fab present. Several peptide segments, however, were found to have significantly decreased deuterium incorporation upon Fab binding. All the residues in this paragraph are numbered according to SEQ ID NO: 74. Deglycosylated human PD-1 showed strong reduction in deuterium uptake upon binding to anti-human PD-1 Fab at residues 107-122 (SLAPKAQIKESLRAEL) (SEQ ID NO: 75). In addition, a decrease in deuterium uptake was observed at residues 5-22 (LDSPDRPWNPPTFSPALL) (SEQ ID NO: 76) upon binding to anti-human PD-1 Fab.

6.3.2 Epitope Mapping of Anti-PD-1 Antibody Using a Pepscan Analysis

The binding of anti-PD-1 antibody AGEN2034w was measured against synthesized PD-1 peptide fragments prepared as a chip-bound peptide array. Analysis was performed by Pepscan Presto BV, Lelystad, the Netherlands. Briefly, to reconstruct epitopes of human PD-1, a library of peptides was synthesized. An amino functionalized polypropylene support was obtained by grafting with a proprietary hydrophilic polymer formulation, followed by reaction with t-butyloxycarbonyl-hexamethylenediamine (BocHMDA) using dicyclohexylcarbodiimide (DCC) with Nhydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS liquid handling stations (Perkin Elmer). Synthesis of structural mimics was conducted using Pepscan's proprietary Chemically Linked Peptides on Scaffolds (CLIPS) technology. CLIPS technology allows to structure peptides into single loops, double loops, triple loops, sheet-like folds, helix-like folds and combinations thereof. The binding of antibody to each of the synthesized peptides was tested in a PEPSCAN-based ELISA. The peptide arrays were incubated with primary antibody solution overnight at 4° C. After washing, the peptide arrays were incubated with a goat anti-human HRP conjugate (Southern Biotech, Cat#2010-05) for one hour at 25° C. After washing, the peroxidase substrate 2,2'-azino-di-3-ethylbenzthiazoline sulfonate (ABTS) and 20 µl/ml of 3% $H_2O_2$ were added. After one hour, the color development was measured and quantified with a charge coupled device (CCD)—camera and an image processing system.

The Pepscan study showed that the anti-PD-1 antibody AGEN2034w recognized stretches of human PD-1 including residues 6-15 (DSPDRPWNPP) (SEQ ID NO: 77), residues 130-138 (EVPTAHPSP) (SEQ ID NO: 78), and residues 106-113 (ISLAPKAQ) (SEQ ID NO: 79), numbered according to SEQ ID NO: 74.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

What is claimed:

1. An isolated antibody that specifically binds to human PD-1, comprising a heavy chain variable region comprising complementarity determining regions CDRH1, CDRH2, and CDRH3, wherein CDRH1, CDRH2, and CDRH3 comprise the amino acid sequences of SEQ ID NOs: 1, 2, and 7, respectively; and a light chain variable region comprising the amino acid sequence of SEQ ID NO: 16.

2. The isolated antibody of claim 1, wherein the amino acid sequence of the light chain variable region consists of the amino acid sequence of SEQ ID NO: 16.

3. The isolated antibody of claim 1, wherein the antibody comprises a light chain comprising the amino acid sequence of SEQ ID NO: 19.

4. The isolated antibody of claim 3, wherein the amino acid sequence of the light chain consists of the amino acid sequence of SEQ ID NO: 19.

5. An isolated antibody that specifically binds to human PD-1, comprising a heavy chain comprising the amino acid sequence of SEQ ID NO: 20; and a light chain variable region comprising complementarity determining regions CDRL1, CDRL2, and CDRL3, wherein CDRL1, CDRL2, and CDRL3 comprise the amino acid sequences of SEQ ID NOs: 4, 5, and 6, respectively.

6. The isolated antibody of claim 5, wherein the amino acid sequence of the heavy chain consists of the amino acid sequence of SEQ ID NO: 20.

7. An isolated antibody that specifically binds to human PD-1, comprising a heavy chain variable region comprising the amino acid sequence of SEQ ID NO: 17; and a light chain variable region comprising the amino acid sequence of SEQ ID NO: 16.

8. The isolated antibody of claim 7, wherein the amino acid sequence of the heavy chain variable region consists of the amino acid sequence of SEQ ID NO: 17; and the amino acid sequence of the light chain variable region consists of the amino acid sequence of SEQ ID NO: 16.

9. The isolated antibody of claim 7, wherein the antibody comprises a heavy chain comprising the amino acid sequence of SEQ ID NO: 53.

10. The isolated antibody of claim 9, wherein the amino acid sequence of the heavy chain consists of the amino acid sequence of SEQ ID NO: 53.

11. The isolated antibody of claim 7, wherein the antibody comprises a heavy chain comprising the amino acid sequence of SEQ ID NO: 20.

12. The isolated antibody of claim 11, wherein the amino acid sequence of the heavy chain consists of the amino acid sequence of SEQ ID NO: 20.

13. The isolated antibody of claim 7, wherein the antibody comprises a light chain comprising the amino acid sequence of SEQ ID NO: 19.

14. The isolated antibody of claim 13, wherein the antibody comprises a heavy chain comprising the amino acid sequence of SEQ ID NO: 23.

15. The isolated antibody of claim 13, wherein the amino acid sequence of the light chain consists of the amino acid sequence of SEQ ID NO: 19.

16. An isolated antibody that specifically binds to human PD-1, comprising a heavy chain and a light chain, wherein the heavy chain comprises the amino acid sequence of SEQ ID NO: 53; and the light chain comprises the amino acid sequence of SEQ ID NO: 19.

17. The isolated antibody of claim 16, wherein the amino acid sequence of the heavy chain consists of the amino acid sequence of SEQ ID NO: 53.

18. The isolated antibody of claim 16, wherein the heavy chain comprises the amino acid sequence of SEQ ID NO: 20.

19. The isolated antibody of claim 18, wherein the amino acid sequence of the heavy chain consists of the amino acid sequence of SEQ ID NO: 20.

20. The isolated antibody of claim 16, wherein the amino acid sequence of the light chain consists of the amino acid sequence of SEQ ID NO: 19.

21. The isolated antibody of claim 16, wherein the amino acid sequence of the heavy chain consists of the amino acid sequence of SEQ ID NO: 53, and the amino acid sequence of the light chain consists of the amino acid sequence of SEQ ID NO: 19.

22. The isolated antibody of claim 16, wherein the heavy chain comprises the amino acid sequence of SEQ ID NO: 20, and the amino acid sequence of the light chain consists of the amino acid sequence of SEQ ID NO: 19.

23. The isolated antibody of claim 22, wherein the amino acid sequence of the heavy chain consists of the amino acid sequence of SEQ ID NO: 20, and the amino acid sequence of the light chain consists of the amino acid sequence of SEQ ID NO: 19.

24. A pharmaceutical composition comprising the antibody of claim 1 and a pharmaceutically acceptable carrier or excipient.

25. A pharmaceutical composition comprising the antibody of claim 5 and a pharmaceutically acceptable carrier or excipient.

26. A pharmaceutical composition comprising the antibody of claim 7 and a pharmaceutically acceptable carrier or excipient.

27. A pharmaceutical composition comprising the antibody of claim 8 and a pharmaceutically acceptable carrier or excipient.

28. A pharmaceutical composition comprising the antibody of claim 16 and a pharmaceutically acceptable carrier or excipient.

29. A pharmaceutical composition comprising the antibody of claim 21 and a pharmaceutically acceptable carrier or excipient.

30. A pharmaceutical composition comprising the antibody of claim 23 and a pharmaceutically acceptable carrier or excipient.

* * * * *